United States Patent
Chu et al.

(10) Patent No.: US 11,090,273 B2
(45) Date of Patent: Aug. 17, 2021

(54) TAGGED POLY(ESTER AMIDE URETHANE)S, NANOPARTICLES FORMED FROM SAME, AND USES THEREOF

(71) Applicant: Cornell University, Ithaca, NY (US)

(72) Inventors: Chih-Chang Chu, Ithaca, NY (US); Mingyu He, Ithaca, NY (US); Ying Ji, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 16/334,820

(22) PCT Filed: Sep. 20, 2017

(86) PCT No.: PCT/US2017/052560
§ 371 (c)(1),
(2) Date: Mar. 20, 2019

(87) PCT Pub. No.: WO2018/057649
PCT Pub. Date: Mar. 29, 2018

(65) Prior Publication Data
US 2020/0129447 A1    Apr. 30, 2020

Related U.S. Application Data

(60) Provisional application No. 62/397,107, filed on Sep. 20, 2016.

(51) Int. Cl.
*A61K 9/51* (2006.01)
*A61K 31/704* (2006.01)
*C08G 18/83* (2006.01)

(52) U.S. Cl.
CPC .......... *A61K 9/5153* (2013.01); *A61K 31/704* (2013.01); *C08G 18/833* (2013.01)

(58) Field of Classification Search
CPC ... A61K 9/5153; A61K 31/704; C08G 18/833

USPC .......................................................... 514/34
See application file for complete search history.

(56) References Cited

U.S. PATENT DOCUMENTS

2008/0227018 A1* 9/2008 Awamura ............. G03G 9/0827
430/110.4
2016/0237212 A1* 8/2016 Becker ................... C08G 71/02

OTHER PUBLICATIONS

He, et al., "A new family of functional biodegradable arginine-based polyester urea urethanes: Synthesis, characterization and biodegradation," Polymer (54), 2013, all enclosed pages cited.
He, et al., "Self-Assembled Cationic Biodegradable Nanoparticles from pH-responsive Amino-Acid-Based Poly(Ester Urea Urethane)s and Their Application as a Drug Delivery Vehicle," Biomacromolecules 2016, all enclosed pages.

* cited by examiner

*Primary Examiner* — Shaojia A Jiang
*Assistant Examiner* — Michael C Henry
(74) *Attorney, Agent, or Firm* — Johnson, Marcou, Isaacs & Nix, LLC; Paul J. Roman, Jr.

(57) ABSTRACT

Provided are polymers (e.g., polymeric materials), nanoparticles comprising one or more of the polymers, and compositions. A polymer may be in the form of a nanoparticle. A polymer can be linear or branched. A polymer includes one or more poly(ester urea) segment, optionally, one or more poly(urethane) segment, optionally, one or more diol segment, optionally, one or more poly(ethylene glycol) segment, and, optionally, one or more terminal/end group. A polymer (e.g., a polymeric material) may include a branching moiety. For example, a composition includes one or more polymer. In an example, polymers and nanoparticles can be used to deliver a drug (e.g., gambogic acid) to an individual (e.g, who has been diagnosed with or is suspected of having cancer and/or a viral infection).

25 Claims, 42 Drawing Sheets

A

A

B

A

B

C (A) FITC labeled blank 6-Arg-4-Leu-4 A/L-2/1 NPs (B) 25 µg/mL 20wt% DOX loaded 6-Arg-4-Leu-4 A/L-2/1 NPs (C) 5 µg/mL free DOX

| Arg-Leu PEUU/Solvents | H₂O | DMF | DMSO | Ethanol | Methanol | Chloroform | THF | Ethyl acetate | Acetone |
|---|---|---|---|---|---|---|---|---|---|
| 6-Leu-4 | - | + | + | + | + | - | + | - | - |
| 6-Arg-4-Leu-4 A/L-1/4 | - | + | + | + | + | - | T | - | - |
| 6-Arg-4-Leu-4 A/L-1/2 | - | + | + | + | + | - | T | - | - |
| 6-Arg-4-Leu-4 A/L-1/1 | - | + | + | + | + | - | T | - | - |
| 6-Arg-4-Leu-4 A/L-2/1 | - | + | + | + | + | - | T | - | - |
| 6-Arg-4 | - | + | + | - | - | - | - | - | - |

+ Soluble defined as > 10 mg/mL at room temperature; - Insoluble; T, turbid suspension

Figure 24

TAGGED POLY(ESTER AMIDE URETHANE)S, NANOPARTICLES FORMED FROM SAME, AND USES THEREOF

CROSS REFERENCE TO RELATED APPLICATIONS

This application claims priority to U.S. Provisional Application No. 62/397,107, filed on Sep. 20, 2016, the disclosure of which is hereby incorporated by reference.

FIELD OF THE DISCLOSURE

The disclosure generally relates to polymers and nanoparticles for drug delivery. More particularly the disclosure generally relates to polymers comprising poly(ester amide)(s) and poly(ester urea)(s).

BACKGROUND OF THE DISCLOSURE

Polymer nanoparticles (NPs), polymer micelles, and polysomes have been investigated and applied as anticancer drug nanocarriers. For example, amphiphilic block copolymers, poly(D,L-lactide)-b-poly(ethylene glycol) (PLA-b-PEG), PEG-poly(L-lysine), and poly(acrylic acid)-b-polystyrene copolymers are able to self-assemble into spherical nanoparticles in water. The hydrophobic core of the self-assembled NPs usually serves as the reservoir for poorly water-soluble anticancer drugs, whereas the hydrophilic shell can stabilize and maintain the dispersion of the NPs in an aqueous medium, and sometimes also improve the barrier permeability. DOX is an anthracycy-line antibiotic and ranked among the most used cancerostatic drugs in current oncological chemotherapy. However, the administration of DOX via infusion is associated with significant drug leakage into the systemic circulation and nonspecific distribution to healthy tissues, which results in severe cytotoxicity side effects. Polymer NPs like gelatin sponge particles, poly (lactic-co-glycolic acid) (PLGA), PEGylated PLGA, and PEG-stearate NPs have been used as DOX carriers and have shown increased DOX accumulation in tumor tissue, higher anticancer activity, and lower systemic toxicity when compared to free DOX (i.e., without carriers) in preclinical animal models. Natural amino acids, i.e. glutamic acid (Glu), phenylalanine (Phe), arginine (Arg), and lysine (Lys), were utilized to develop amphiphilic polymers, which have merits such as biodegradability, good biocompatibility, and the physical and chemical characteristics of side-chain functional groups.

Two families of biodegradable amino-acid-based poly (ester amide) (AA-PEA) and poly(ester urea urethane) (AA-PEUU) biomaterials with good biocompatibility have been developed. Compared to conventional biodegradable aliphatic polyester biomaterials, e.g., poly(lactic acid) (PLA), poly-(caprolactone) (PCL), poly(glycolic acid) (PGA) and their copolymers, the amino acid side groups on these amino-acid-containing polymers (AA-PEA and AA-PEUU) provide useful pendant reactive sites, tunable hydrophilicity, anionic/cationic charge, degradation rates, and a wide range of chemical, mechanical, thermal, physical, and biological properties.

Amino-acid-based PEA and PEUU materials synthesized from cationic amino acids, such as Arg or Lys are of particular interest because of the cationic nature of the polymers and the important biological roles they play. It is known that cationic drug carriers can undergo a quick binding process onto negatively charged cell membranes, followed by a rapid drug uptake by cells. Moreover, some Arg-rich proteins or Arg-rich peptide cationic drug carriers achieved the proton sponge effect (pH-buffering effect) that facilitates endosomal escape and provides better controlled drug release profiles. To biomimic the Arg-rich biopolymers, a water-soluble Arg-based PEA family was developed, and its application as a nonviral gene vector was reported. In those studies, certain types of Arg-PEAs showed very good transfection efficiency with very low cytotoxicity. A water-insoluble derivative of water-soluble Arg-PEA, consisting of two amino acids (Arg and Phe), was also synthesized (Arg-Phe PEA) and fabricated into NPs in a diluted poly (vinyl alcohol) aqueous solution under a gentle stirring.

Another newly synthesized amphiphilic Arg-containing poly(ester urea urethane) family, Arg PEUUs, possesses not only a strong cationic charge and hydrolyzable ester bond linkage on the polymer chain, but this family also possesses largely improved mechanical strength and the ability to photo-cross link. The facile preparation and highly versatile chemistry of amino-acid-based PEUUs enable the incorporation of various functional building blocks to generate stable nanoassemblies with the desired performance.

It is known that macrophages produce different levels of cytotoxic oxygen species and cytokines (superoxide, TNF-α, NO, IL-10, etc.) at classic or alternative activation modes. In tumor progression, macrophages and tumor cells have a complex relationship: macrophages produce chemokine-inhibiting cancer cells, whereas in most types of solid tumors, macrophages promote angiogenesis in tumor progression. By regulating the inducible nitric oxide synthase (iNOS) or arginase pathways of Arg metabolism, macrophages perform either destructive or constructive functions in pathological processes, i.e. tumor growth inhibition, and wound healing. An in vitro macrophage and cancer cell co-culture study reported that the activation of macrophages by the phagocytosis of the DOX conjugated PLGA NPs significantly elevated NO production and hence improved the efficacy of DOX that was conjugated to the PLGA NP carrier toward cancer cells.

Gambogic acid (GA), the main active medicinal compound of the gamboge resin that produced by *Garcinia hanburyi* trees in Southeast Asia, has been reported to demonstrate significant cytotoxic activity against multiple types of cancer cells in culture and in vivo (FIG. 1). GA can reduce the growth rate of leukemia, lung carcinoma, breast carcinoma and pancreatic cancer cells. Several studies have suggested that GA can suppress the growth of human tumors by multiple different mechanisms, such as inhibiting the expression of telomerase and telomerase reverse transcriptase mRNA, inhibiting the promoter of the human telomerase reverse transcriptase (hTERT), down-regulating Bcl-2, activating tumor necrosis factor (TNF)-induced apoptosis, inhibiting the NF-κB signaling pathway, suppressing cyclin-dependent kinase 7 (CDK7)-mediated phosphorylation of CDC2/34, and inhibiting VEGF-induced angiogenesis, etc. GA has been approved for phase II clinical trial for cancer therapy by the Chinese Food and Drug Administration (CFDA).

One important aspect of anticancer activity of GA is its induction of the apoptotic process. In general, induction of apoptosis for mammal species occurs primarily by two distinct but ultimately converging intrinsic and extrinsic signaling pathways: the Bcl-2 family regulated pathway (intrinsic or mitochondrial pathway) and the death-receptor pathway (extrinsic pathway). The mitochondrial pathway can be triggered by cellular stress, cytokine withdrawal or cytotoxic stimuli, and eventually lead to the disruption of the outer mitochondrial membrane, resulting in the release of cytochrome c and the other apoptogenic proteins. The death-receptor pathway is activated by ligation of proteins known as death receptors which are in the tumor necrosis factor receptor (TNFR) family. Different from these two classic apoptosis induction pathways, GA is found to bind to transferrin receptor (TfR) that subsequently activates the apoptosis cascade by caspase-8 and the mitochondrial pathway. Many reported studies suggest that the GA-mediated apoptosis hardly involves the extrinsic pathway. Moreover, GA acts as a prodrug and gains the proteasome-inhibitory function after being metabolized by intracellular CYP2E1 (cytochrome P450 2E1).

Compared to many conventional chemotherapeutic drugs in both animal tumor models and clinical trials, GA shows little chemotoxicity on immune and hemopoietic systems. However, several drawbacks, such as poor water solubility (<1 µg/mL), sensitivity to environmental factors like light, temperature, and humidity, fast clearance in plasma, and wide tissue distribution also limit the commercial development of pharmaceutical formulation and clinical application of GA. There is a great need for better GA delivery strategies. Using polymeric drug nanocarriers is a strategy employed to solve this problem.

Biodegradable arginine (Arg) based poly(ester amide) and poly(ester urea urethane) (PEUU) have been developed to promote wound healing quality and as gene and drug carriers. Arg PEUU NPs are promising nanocarrier biomaterials prepared by a facile dialysis method with adjustable cationic charge that are able to undergo a quick binding process onto the negatively charged cell membranes, followed by a rapid drug uptake by cells. Functionalized linear Arg-PEUUs are synthesized from 4 building blocks: Arg, diols, diisocyanate, and glycerol α-monoallyl ether. By controlling the feed ratio of monomers, the synthesized functional Arg-PEUU and Arg-Leu (Leucine) PEUU could be self-assembled into nanoparticles (NPs) in an aqueous environment. The facile preparation and highly variable chemistry of amino acid-based PEUUs enable the conjugation of targeting biomolecules to enhance the therapeutic efficacy of their drug delivery.

Folate receptor (FR) is a cell surface glycosyl phosphatidylinositol (GPI)-anchored glycopolypeptide that characteristically binds folic acid (folate, FA) and transports them by a non-classical endocytic mechanism. High expression of FR is associated with poorly differentiated and more aggressive tumors. Many malignant tumors are known to overexpress FR-α, including adenocarcinomas of the ovary, uterus and cervix, testicular choriocarcinoma, ependymal brain tumors, pleural mesothelioma, etc. Greater than 90% of ovarian carcinomas overexpress FR-α. Anticancer drugs, such as taxol and carboplatin have been conjugated to FA in attempts to use them as prodrugs to improve tissue-selective drug delivery. FA has also been immobilized on the surface of nano-particulate carriers to deliver into targeted cells via receptor-mediated endocytosis. FA-targeted nanoparticles (NPs)/liposomes have the potential to circumvent major limitations of some chemotherapeutic drugs (e.g., doxorubicin, paclitaxel) like poor water solubility by enveloping the drug with the desired drug concentration, prolonging the circulation time and facilitating intracellular delivery through the FR-mediated targeting. Also, most types of cancer cells also overexpress TfR which is the targeting site for GA-mediated apoptosis. Studies of recycling kinetics indicated FR-α is recycled at 3-fold slower rate compared to transmembrane TfR.

SUMMARY OF THE DISCLOSURE

In an aspect, the present disclosure provides polymers and nanoparticles. A polymer may be in the form of a nanoparticle. A polymer can be referred to as a polymeric material. A polymer is linear or branched and comprises one or more poly(ester urea) segment, optionally, one or more poly(urethane) segment, optionally, one or more diol segment, optionally, one or more poly(ethylene glycol) segment, and, optionally, one or more folate group, amine group, or fluorescent dye group. The polymer can be referred to as a copolymer.

A polymer can be a branched polymer. A branched polymer can be referred to as a polymeric compound. A branched polymer comprises a branching moiety. A branching moiety has one or more polymeric group covalently bound it. A polymer can be a linear polymer. A linear polymer comprises one or more poly(ester urea) segments (e.g., and one or more hydrophilic poly(ester urea) segment); optionally, one or more poly(urethane) segments (e.g., and one or more hydrophobic poly(urethane) segment), and optionally, one or more diol segments.

A polymer of the present disclosure can form a nanoparticle. A nanoparticle can comprise a drug. A drug (e.g., a hydrophobic drug such as, for example, gambogic acid) is sequestered in the nanoparticle.

In an aspect, the present disclosure provides compositions comprising one or more polymer and/or nanoparticle of the present disclosure. The compositions can be used to deliver a drug to an individual. The compositions may comprise one or more pharmaceutically acceptable carrier.

In aspect the disclosure provides products, e.g. articles of manufacture, which comprise pharmaceutical preparations containing any one or any combination of the polymers, nanoparticles, and compositions described herein. In an example, a kit comprises any one or any combination of the polymers, nanoparticles, and compositions described herein.

In an aspect, the present disclosure provides methods that use the polymers and/or nanoparticles of the present disclosure. In various examples, the present disclosure provide methods of administering a drug to an individual. The present disclosure provides methods of using one or more compounds of the present disclosure. For example, the compounds can be used to treat cancer and/or viral infections.

BRIEF DESCRIPTION OF THE FIGURES

For a fuller understanding of the nature and objects of the disclosure, reference should be made to the following detailed description taken in conjunction with the accompanying figures.

FIG. 24 shows solubility data of Arg-Leu PEUUs in water and common organic solvents at room temperature. +Soluble defined as >10 mg/mL at room temperature; -Insoluble; T; turbid suspension.

DETAILED DESCRIPTION OF THE DISCLOSURE

Figure 1:
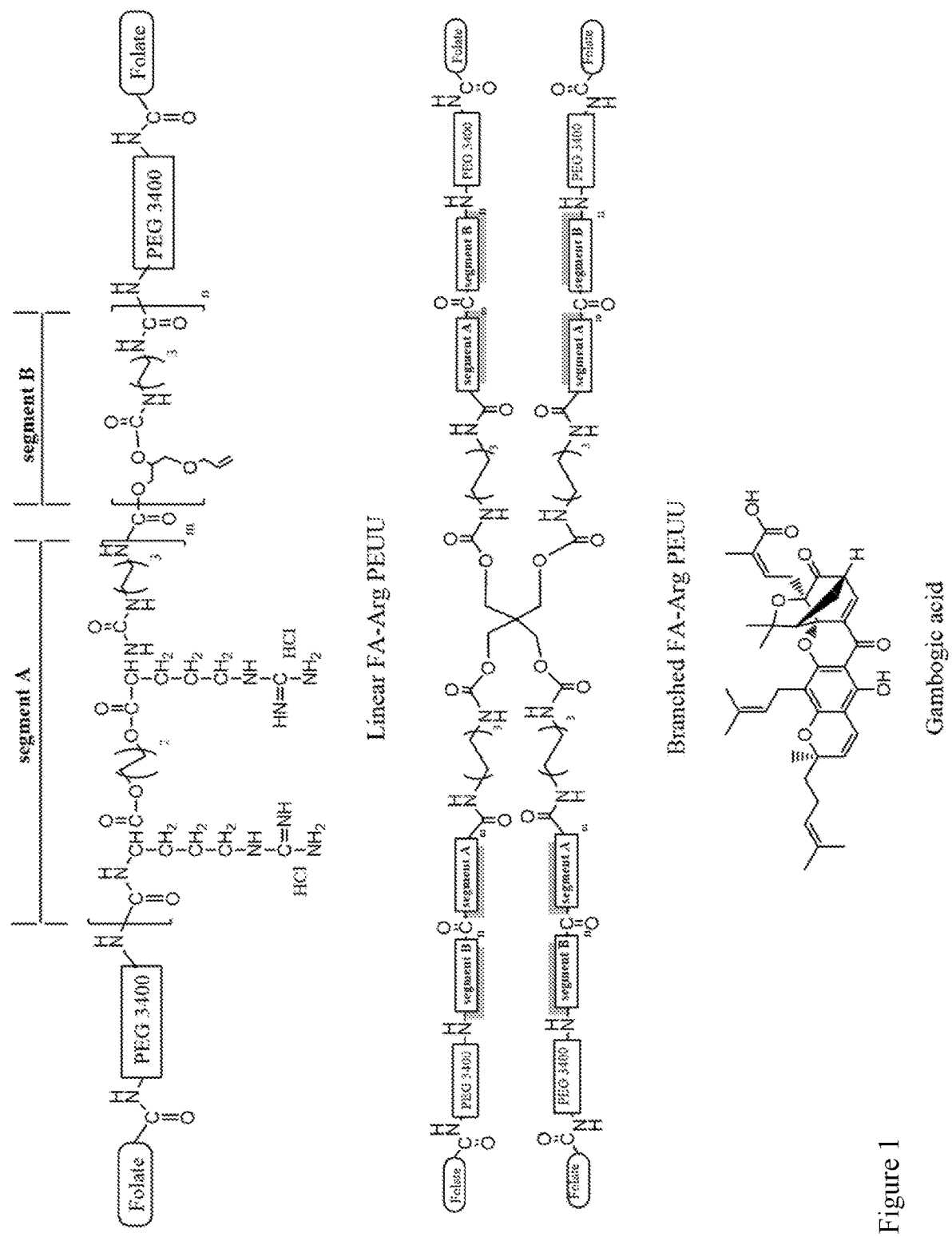
FIG. 1 shows a schematic chemical structure of linear, branched FA-Arg-PEUU and chemical structure of gambogic acid.

Although claimed subject matter will be described in terms of certain embodiments and examples, other embodiments and examples, including embodiments and examples that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

As used herein, unless otherwise stated, the term "group" refers to a chemical entity that has one terminus that can be covalently bonded to other chemical species. Examples of groups include, but are not limited to:

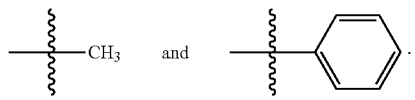

As used herein, unless otherwise stated, the term "moiety" refers to a chemical entity that has two or more termini that can be covalently bonded to other chemical species. Examples of moieties include, but are not limited to:

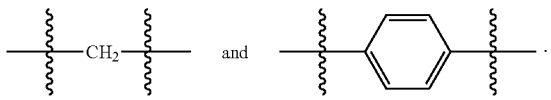

As used herein, unless otherwise indicated, the term "alkyl" refers to branched or unbranched saturated hydrocarbon groups. Examples of alkyl groups include, but are not limited to, methyl groups, ethyl groups, propyl groups, butyl groups, isopropyl groups, tert-butyl groups, and the like. For example, the alkyl group can be a $C_1$ to $C_{12}$, including all integer numbers of carbons and ranges of numbers of carbons therebetween, alkyl group. The alkyl group can be unsubstituted or substituted with one or more substituent. Examples of substituents include, but are not limited to, various substituents such as, for example, halogens (—F, —Cl, —Br, and —I), aliphatic groups (e.g., alkyl groups, alkenyl groups, alkynyl groups), aryl groups, alkoxide groups, carboxylate groups, carboxylic acids, ether groups, guanidium groups and the like, and combinations thereof. For example, a guanidium group can be covalently bonded to the terminus of the longest linear chain

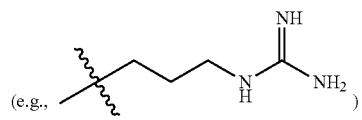 [SMILES: *CCCNC(=N)N]

or covalently bonded to an alkyl moiety branching off the longest linear chain

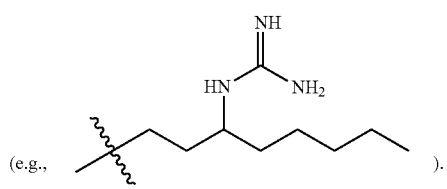 [SMILES: *CCC(CCCCC)NC(=N)N]

Examples of these groups can be called alkylguanidinium groups.

The present disclosure provides polymers, nanoparticles, and compositions comprising one or more polymers and/or one or more nanoparticles. The polymers, nanoparticles, and compositions can be used in drug delivery methods.

A goal of this disclosure is to develop a new family biodegradable and functional amino acid-based poly(ester urea urethane) biomaterials (AA-PEUU) that can be self-assembled into nanoparticles via hydrophobic and hydrophilic interactions. A model AA-PEUU compound used to demonstrate this new disclosure is Arg/Leu-PEUU in which Arg is arginine (hydrophilic) and Leu (hydrophobic) is leucine amino acids.

AA-PEUUs is a linear polyurethane material family with many variations on the selection of the building blocks, including, but not limited to: amino acid diester monomers, diisocyanate, etc. Also by adjusting the different monomer feed ratio various AA-PEUU materials can be achieved with different mechanical properties, hydrophobicity, etc. Moreover, the AA-PEUU has been demonstrated biocompatible and biodegradable towards mammalian cells. Because the cationic nature, Arg containing PEUUs used as coating can even improve the cell adhesion on the surface of many other materials which worked as a base.

The facile preparation and highly versatile chemistry of amino acid based PEUUs enable the incorporation of various functional building blocks to generate stable nano-assemblies with desired performance. Certain Arg-PEUUs or Arg-Leu PEUUs dissolved in water-miscible organic solvents can self-assemble into sub-micron sized particles by a simple dialysis method against water. Furthermore, Arg metabolism plays an important role in the inflammatory response of macrophages, biodegradable Arg-Leu based PEUU nanoparticles (NPs) might also lead to the inflammatory activation of macrophages to argument their inflammatory response toward cancer cells.

An important building block of AA-PEUU system is the glycerol 1-allyl ether (GAE) which provides the pendant double bond functionality, such as UV-crosslinking or further conversion to other chemical groups. For the UV-crosslinked PEUU coating or UV-crosslinked PEUU elastomer fabrication, high crosslinking density and hydrophobicity should be enhanced, the molar ratio of GAE to the total amount of monomers may have a value from 0.5 to 1. For the self assembled NP fabrication, the molar feed ration of GAE may not be higher than 0.2. The photo crosslinking capability of AA-PEUU could open the door for using this family of polymers for 3D printing of articles.

AA-PEUUs with a substantial feed ratio of GAE building blocks could be crosslinked under the UV radiation with the presence of photo-initiator within minutes. These AAPEUUs are promising 3D printing material, particularly, the AA-PEUU with Leu composition which could be dissolved in low boiling point organic solvents, e.g., methanol and ethanol.

The pendant double bonds of AA-PEUUs can also be further converted into other chemical functional groups (amine, carboxyl, hydroxyl) by the thiol-ene reaction. The introduced pendant amine groups on the PEUUs could be coupled with fluorescent dyes such as Fluorescein isothiocyanate (FITC), NHS-rhodamine, Cyanine 5.5 NHS ester etc for the preparation of NPs with desired fluorescence. One application of the fluorescent AA-PEUU is to prepare NPs which could be used to visualize the cellular uptake of the NPs under the fluorescent microscopy. The fluorescent AA-PEUU NPs might be applied as tractable drug carriers or a tool in the study of NP biodistribution.

Gambogic acid (GA) is a natural compound exhibiting a broad spectrum of anticancer activity and low chemotoxicity to normal tissues. However, poor aqueous solubility and sensitivity to hydrolysis that makes its pharmaceutical applications a challenge. In order to overcome these drawbacks, linear and branched Arg-based poly(ester urea urethane)s (Arg-PEUUs), folate (FA) conjugated Arg PEUUs (FA-Arg-PEUUs) and their self-assembled nanoparticles (NPs) were designed, synthesized and studied as the potential GA carriers for cancer treatment. In various examples, the average diameters of linear or branched Arg-PEUU/FA-Arg-PEUU NPs are from 98 to 267 nm, and zeta potential of +12.2 to +5.4 mV. Blank FA-Arg-PEUU NPs adhered onto and were internalized into HeLa and A549 cells, and showed no cytotoxicity. The GA loading efficiency in the NP carriers ranged from 40 to 98%, depending on the feed weight ratio of GA to Arg-PEUU, and the Arg-PEUU polymer structure (i.e., linear vs. branched). About 80-90% of the loaded GA in linear and branched FA-Arg-PEUU NPs was released in 60 h in vitro. The GA at 2 µg/mL concentration delivered by the FA-Arg-PEUU NP carriers led to a higher cytotoxicity and induced a higher apoptosis percentage against folate receptor (FR) overexpressed HeLa or HCT116 than Arg-PEUU NPs. FR-negative A549 cells was used for comparison to evaluate the role of the FA as targeting ligand. When compared to the free GA treatment, the GA loaded in the FA-Arg-PEUU NP carriers also led to significant loss of the mitochondrial membrane potential in a higher percentage of the cancer cell population and more DNA fragmentation. The GA loaded in FA-Arg-PEUU NP carriers at as low as 0.6 µg/mL GA concentration can also reduce more matrix metalloproteinases (MMP-2 and MMP-9) activity of cancer cells than free GA at the same concentration, suggesting that GA loaded Arg-PEUU NPs may have greater potential to reduce cancer cell invasion and metastasis than the free GA.

A folate-tagged branched Arginine based (ester urea urethane) can self-assemble into nanoparticles in water. In various examples, AA-PEUU copolymers can be synthesized from 4 building blocks: hydrophilic amino acid, hydrophobic amino acid, diols, 1,6 hexamethylene diisocyanate and diamino polyethylene glycol 3400. The branched Arg PEUU copolymers can have weight-average molecular weights around 25.5 KDa and glass-transition temperatures around −19.2° C. The self-assembled cationic nanoparticles (branched Arg PEUU NPs) can be easily prepared by, for example, a facile dialysis method. Arg-Leu PEUU NPs can have average diameters around 140 nm. Folate tagged branched Arg-PEUU NPs can improve the cell attachment/internalization and enhanced anti-cancer drug potency against cancer cells.

In an aspect, the present disclosure provides polymers and nanoparticles. A polymer may be in the form of a nanoparticle. A polymer can be referred to as a polymeric material. A polymer is linear or branched and comprises one or more poly(ester urea) segment, optionally, one or more poly(urethane) segment, optionally, one or more diol segment, optionally, one or more poly(ethylene glycol) segment, and, optionally, one or more folate group. The polymer can be referred to as a copolymer.

A polymer comprises one or more poly(ester urea) segment. A polymer can have the same or a combination of poly(ester urea) segments be the same or different.

In an example, a poly(ester urea) segment is a hydrophililc poly(ester urea) segment. A hydrophililc poly(ester urea) segment comprises one or more hydrophilic side chain (e.g., $R^1$), which can be the side chain of a hydrophilic amino acid residue (e.g., an arginine reside).

In an example, a poly(ester urea) segment is a hydrophobic poly(ester urea) segment. A hydrophobic poly(ester urea) segment comprises one or more hydrophobic side chain (e.g., $R^3$). For example, the side chain is the side chain of a hydrophobic amino acid residue (e.g., an leucine reside).

A poly(ester urea) segment can have various sizes. For example, a poly(ester urea) segment has a molecular weight (e.g., $M_w$ and/or $M_n$) of 376 to 615 g/mol, including all integer values and ranges therebetween. In other examples, the poly(ester urea) segment has a molecular weight (e.g., $M_w$ and/or $M_n$) of 200 to 75,000 g/mol, including all integer values and ranges therebetween.

For example, a poly(ester urea) segment has the following structure:

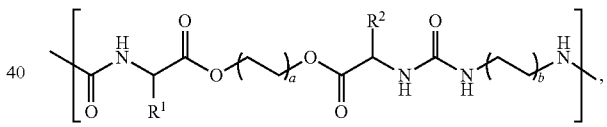

where $R^1$ and $R^2$ are independently, at each occurrence in the polymer, a hydrophilic group (e.g., a cationic group such as for example, an alkylguanidinium group (e.g., a side chain of a hydrophilic amino acid residue such as, for example, an arginine residue) or a hydrophobic group (e.g., a non-polar group such as, for example, an alkyl group (e.g., a side chain of hydrophobic amino acid residue such as, for example, a leucine residue); a is independently, at each occurrence in the polymer, 1, 2, or 3; and b is independently, at each occurrence in the polymer 2 or 3. In various examples, a poly(ester urea) segment or poly(ester urea) segments is/are one or more hydrophilic poly(ester urea) segments and/or one or more hydrophobic poly(ester urea) segments.

A polymer may comprise one or more poly(urethane) segment. A polymer can have the same or a combination of poly(urethane) segments be the same or different.

In an example, a poly(urethane) segment is a hydrophobic poly(urethane) segment. A hydrophobic poly(urethane) segment comprises one or more hydrophobic side chain (e.g., $R^3$). A side chain may comprise a reactive group (e.g., a carbon-carbon double bond). In an example, a reactive group is a cross-linkable group or a conjugating group. A crosslinkable group can react with another crosslinkable group to crosslink the polymer. A conjugating group can be reacted with a compound, such as, for example, a dye to conjugate the dye to the polymer. For example, a side chain having a reactive group has the following structure:

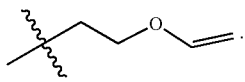 [SMILES: *CCOC=C]

For example, a side chain can be formed using a glycerin derivative.

A poly(urethane) segment can have various sizes. For example, a poly(urethane) segment has a molecular weight (e.g., $M_w$ and/or $M_n$) of 272 to 300 g/mol. In other examples, a poly(urethane) segment has a molecular weight (e.g., $M_w$ and/or $M_n$) of 0 to 7,500 g/mol, including all integer values and ranges therebetween.

For example, a poly(urethane) segment has the following structure:

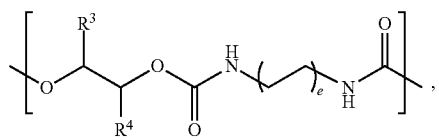

where $R^3$ is independently, at each occurance in the polymer, a side-chain comprising a cross-linkable group (e.g., a carbon-carbon double bond) or hydrogen; $R^4$ is independently, at each occurance in the polymer, a side-chain comprising a cross-linkable group (e.g., a carbon-carbon double bond) or hydrogen; and e is independently, at each occurrence in the polymer, 2 or 3.

A polymer may comprise one or more diol segments. A diol segment comprises one or more chain (e.g., $R^3$ and $R^4$). A side chain may comprise a reactive group (e.g., a carbon-carbon double bond). In an example, a reactive group is a cross-linkable group or a conjugating group. A crosslinkable group can react with another crosslinkable group to crosslink the polymer. A conjugating group can be reacted with a compound, such as, for example, a dye to conjugate the dye to the polymer. For example, a side chain having a reactive group has the following structure:

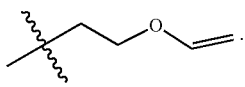 [SMILES: *CCOC=C]

For example, a side chain can be formed from functionalized glycerol derivatives.

A diol segment can have various sizes. For example, a doil segment has a molecular weight (e.g., $M_w$ and/or $M_n$) of 100 to 300 g/mol, including all integer values and ranges therebetween. In other examples, a diol segment has a molecular weight (e.g., $M_w$ and/or $M_n$) of 50 to 5,000 g/mol, including all integer values and ranges therebetween.

For example, a diol segment has the following structure:

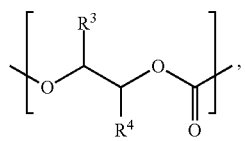

where $R^3$ is independently, at each occurance in the polymer, a side-chain comprising a reactive group (e.g., a crosslinkable or conjugating group comprising a carbon-carbon double bond) or hydrogen; $R^4$ is independently, at each occurance in the polymer, a side-chain comprising a reactive group (e.g., a crosslinkable or conjugating group comprising a carbon-carbon double bond) or hydrogen.

A polymer may comprise one or more poly(ethylene glycol) segment (PEG segment). A PEG segment can have various sizes. For example, a PEG segment has a molecular weight of 1,000 to 5,000 g/mol, including all integer g/mol values and ranges therebetween.

In the cases where a polymer comprises one or more poly(ester urea) segments and one or more poly(urethane) segments, the polymer can comprise various amount of the two types of segments. For example, a linear polymer comprises 80 to 100 mol % poly(ester urea) segment(s), including all integer mol % values and ranges therebetween, and/or 0 to 20 mol % poly(urethane) segment(s). The mol % values are based on the total moles of poly(ester urea) segment(s) and poly(ester urea) segment(s).

A polymer can be a branched polymer. A branched polymer can be referred to as a polymeric compound. A branched polymer comprises a branching moiety. A branching moiety has one or more polymeric group convalently bound it.

A branched polymer can have various branching moieties. In an example, a branching moiety comprises a moiety derived from pentaerythritol.

For example, a branching moiety has the following structure:

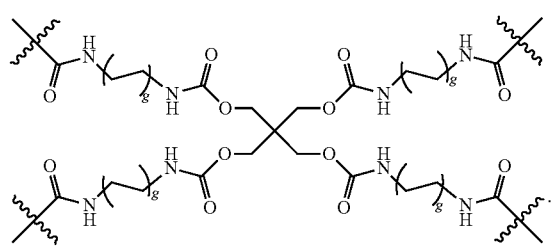

Where g is independently, at each occurrence in the polymer, 2 or 3. A terminus of a poly(ester urea) segment of a polymeric group is covalently bonded (e.g., via an amine moiety or carbonyl moiety) to each terminus of the branching unit.

In another example, a branching moiety has the following structure:

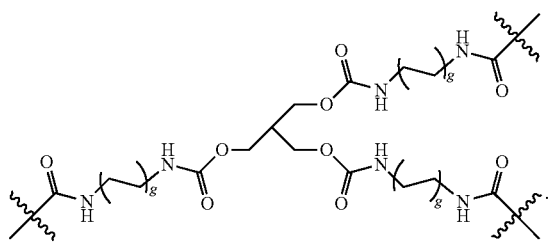

Where g is independently, at each occurrence in the polymer, 2 or 3. A terminus of a poly(ester urea) segment of a polymeric group is covalently bonded (e.g., via an amine moiety or carbonyl moiety) to each terminus of the branching unit.

A polymeric group is covalently bonded (e.g., via an amine moiety or a carbonyl moiety) to the branching moiety. A polymeric group comprises a poly(ester urea) segment (e.g., a poly(ester urea) segment comprising one or more ester urea repeat unit with pendant groups (e.g, two pendant groups such as, for example, alkyl guanidinium groups); a poly(urethane) segment (e.g., a poly(urethane) segment comprising one or more urethane repeat unit with a pendant cross-linkable group (e.g., a carbon-carbon double bond); a poly(ethylene glycol) segment comprising one or more ethylene glycol units; a folate group; and a branching moiety. In each polymeric group the poly(ester urea) segment is covalently bonded (e.g., via a carbonyl moiety) to the poly(urethane) segment, the poly(urethane) segment is covalently bonded (e.g., via an amine moiety) to the poly (ethylene glycol) segment, the folate group is covalently bonded (e.g., via an amide moiety) a terminus of the poly(ethylene glycol) segment.

In an example, a branched polymer comprises polymeric groups (e.g., four polymeric groups or three polymeric groups), each polymeric group comprising: a poly(ester urea) segment comprising one or more ester urea repeat unit with one or more pendant alkyl guanidinium groups (e.g., two pendant alkyl guanidinium groups); a poly(urethane) segment comprising one or more urethane repeat unit with a pendant cross-linkable group (e.g., a carbon-carbon double bond); a poly(ethylene glycol) segment comprising one or more ethylene glycol units; a folate group; and a branching moiety, where in each polymeric group the poly(ester urea) segment is covalently bonded (e.g., via a carbonyl moiety) to the poly(urethane) segment, the poly(urethane) segment is covalently bonded (e.g., via an amine moiety) to the poly (ethylene glycol) segment, the folate group is covalently bonded (e.g., via an amide moiety) a terminus of the poly(ethylene glycol) segment, and wherein each polymeric group is covalently bonded (e.g., via an amine moiety or a carbonyl moiety) to the branching moiety.

In the cases where a polymer comprises one or more poly(ester urea) segments and one or more poly(urethane) segments, the polymer can comprise various amount of the two types of segments. For example, a branched polymer comprises 80 to 100 mol % poly(ester urea) segment(s), including all integer mol % values and ranges therebetween, and/or 0 to 20 mol % poly(urethane) segment(s). The mol % values are based on the total moles of poly(ester urea) segment(s) and poly(ester urea) segment(s).

In various examples, a branched polymer has the following structure:

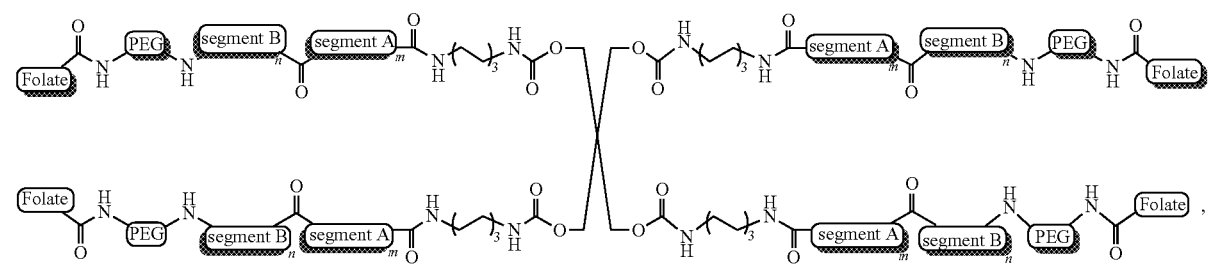

where segment A is

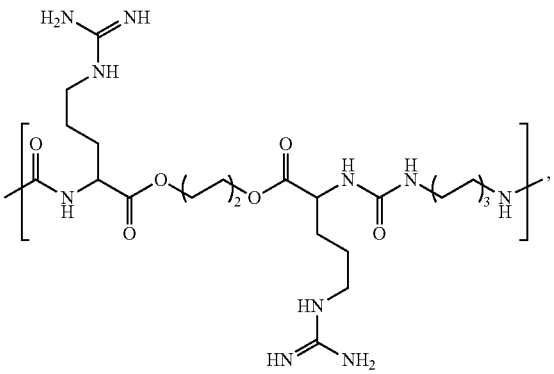

segment B is

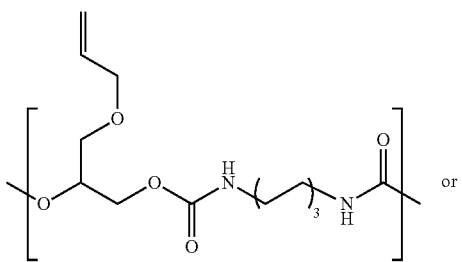 or

-continued

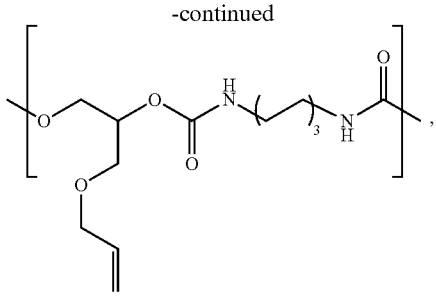

PEG is a poly(ethylene glycol) segment having a molecular weight of 1,000 to 5,000 g/mol, including all integer values and ranges therebetween, folate is

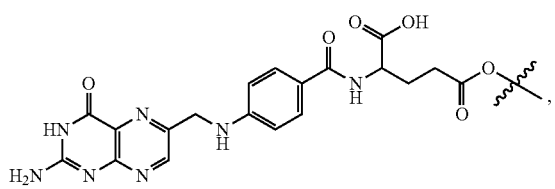

m is 1 to 30, including all integer values and ranges therebetween, and/or n is 0 to 6, including all integer values and ranges therebetween.

A polymer can have various end (e.g., terminal) groups. Examples of as include, but are not limited to, folate groups, amine groups, and/or fluorescent dye groups. In various examples, one or all of the end groups are folate groups. In various examples, one or all of the end groups are fluorescent dye groups. In various examples, one or all of the end groups are amine groups.

A polymer can be a linear polymer. A linear polymer comprises one or more poly(ester urea) segments (e.g., and one or more hydrophilic poly(ester urea) segment); optionally, one or more poly(urethane) segments (e.g., and one or more hydrophobic poly(urethane) segment), and optionally, one or more diol segments.

For example, a linear polymer comprises a hydrophilic poly(ester urea) segment comprising one or more ester urea repeat unit having two pendant alkyl guanidinium groups; and optionally, a poly(urethane) segment comprising one or more urethane repeat unit having a pendant cross-linkable group (e.g., a carbon-carbon double bond), wherein the poly(ester urea) segment covalently bound (e.g., via a carbonyl moiety) to the poly(urethane) segment; and a first poly(ethylene glycol) segment and a second poly(ethylene glycol) segment, each segment comprising one or more ethylene glycol units; and a first folate group and a second folate group, where the first poly(ethylene glycol) segment is covalently bound (e.g., via an amine moiety) to the poly(urethane) segment and the second poly(ethylene glycol) segment is covalently bound (e.g., via an amine moiety) to the hydrophilic poly(ester urea) segment, and the first folate group is segment is covalently bonded (e.g., via an amide moiety) to a terminus of the hydrophilic poly(ester urea) segment and the second folate group segment is covalently bonded (e.g., via an amide moiety) to a terminus of the poly(urethane) segment.

In various examples, a linear polymer has the following structure:

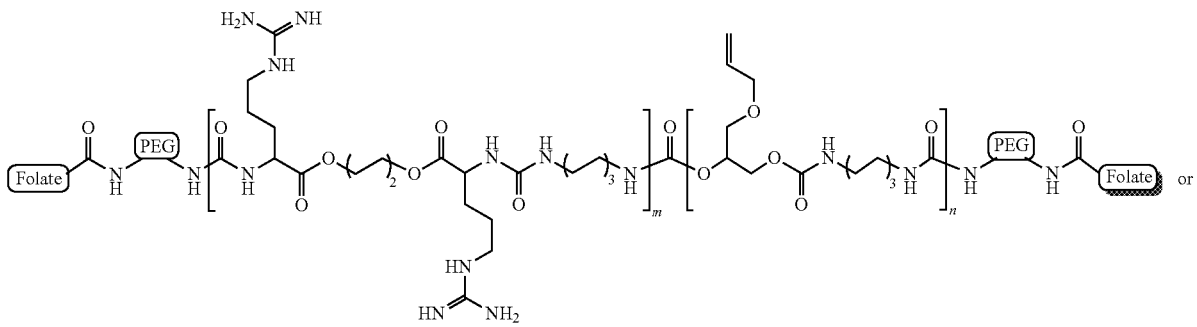 or

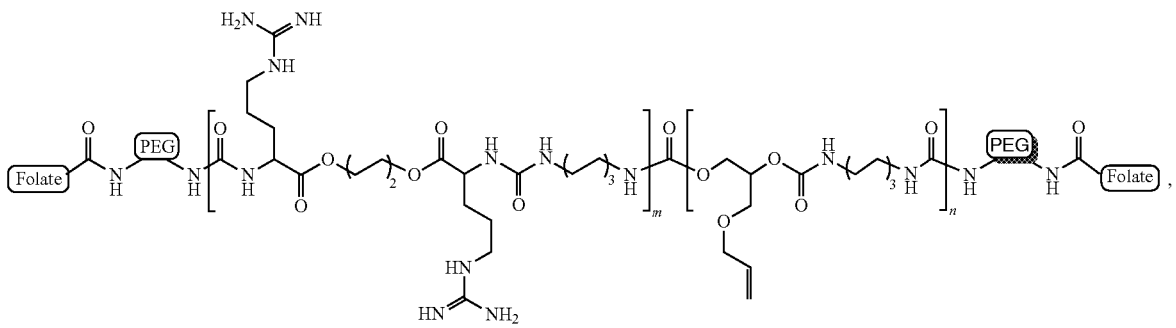, where PEG is a poly(ethylene glycol) segment having a molecular weight of 1,000 to 5,000 g/mol, including all integer values and ranges therebetween, folate is

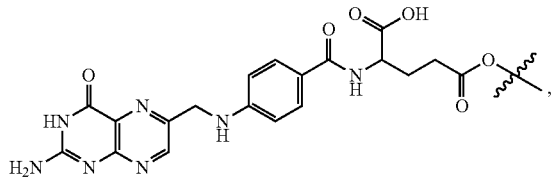 [SMILES: *OC(=O)CCC(NC(=O)c1ccc(NCc2cnc3nc(N)[nH]c(=O)c3n2)cc1)C(=O)O]

m is 1 to 70, including all integer values and ranges therebetween, and/or n is 0 to 14, including all integer values and ranges therebetween.

For example, a linear polymer comprises one or more hydrophilic poly(ester urea) segment (e.g., hydrophilic poly(ester urea) segment(s) comprising one or more ester urea repeat unit having hydrophilic side chains such as, for example, two pendant alkyl guanidinium groups); optionally, a hydrophobic poly(ester urea) segment (e.g., comprising one or more ester urea repeat unit having two pendant alkyl groups; and, optionally, a diol segment comprising one or more diol repeat units having a pendant cross-linkable group (e.g., a carbon-carbon double bond), wherein the poly(ester urea) segments and diol segments are covalently bound (e.g., via a carbonyl moiety).

A linear polymer comprising a pendant carbon-carbon double bond can have various pendant groups conjugated to the polymer via the pendant carbon-carbon double bond. Examples of such polymers are provided herein. For example, a group is conjugated to the polymer via a linking group. Non-limiting examples of pendant groups include fluorescent dyes (e.g., fluorescein), which can be formed, for example, by reaction of a pendant carbon-carbon double bond (or a terminal amine formed from the carbon-carbon double bond) with a suitably functionalized fluorescent dye (e.g., FITC).

In various examples, a linear polymer has the following structure:

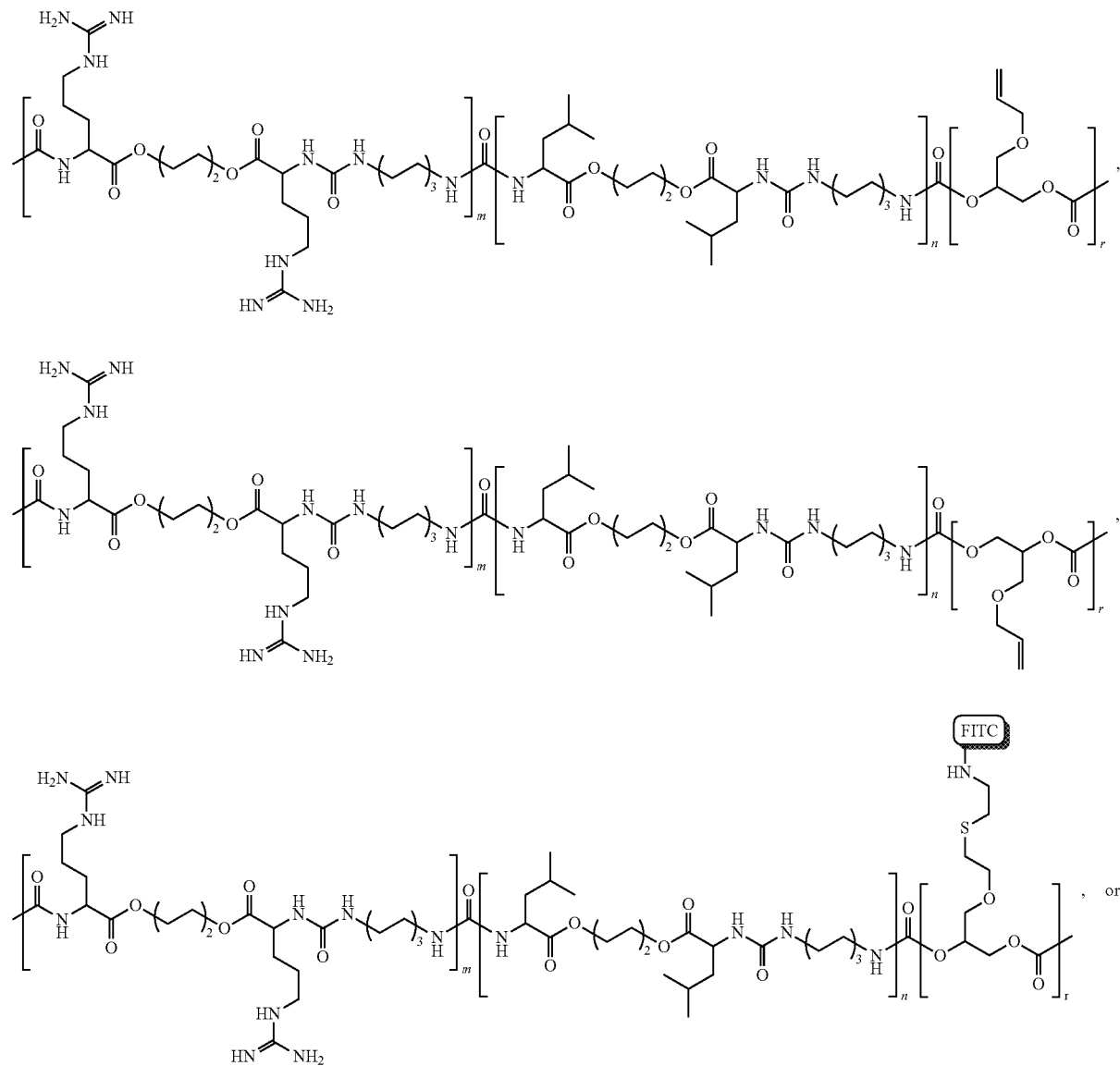

-continued

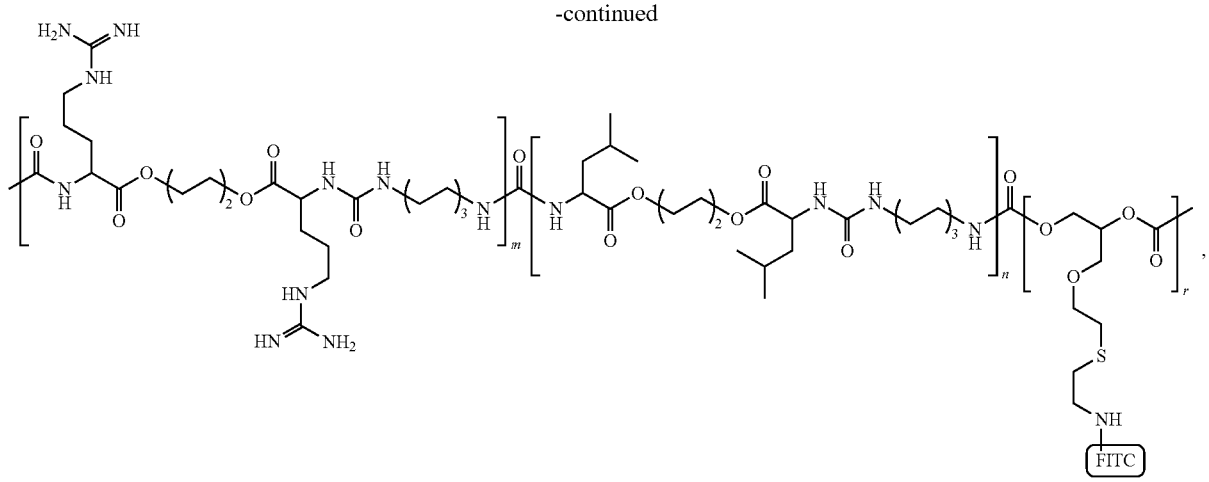

where FITC is

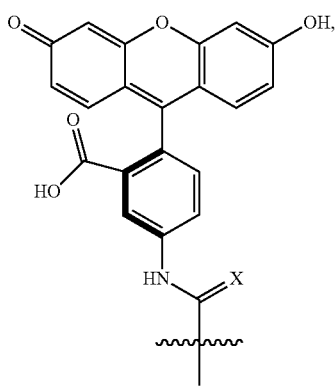

where X is sulfur or oxygen, m is 1 to 70, including all integer values and ranges therebetween, n is 0 to 14, including all integer values and ranges therebetween, and r is 0 to 20, including all integer values and ranges therebetween.

A polymer can have various molecular weights. In various examples, a polymer has a molecular weight (e.g., $M_w$ and/or $M_n$) of 15,000 to 70,000 g/mol, including all integer values and ranges therebetween.

In an example, a polymer comprises a hydrophilic poly(ester urea), an optional hydrophobic (ester urea), and an optional diol. In an example such as this, the hydrophilic poly(ester urea) and hydrophobic (ester urea) have a mole percent (e.g., the percent of the total moles of the hydrophilic poly(ester urea) segment, hydrophobic poly(ester urea) segment, and diol segment) of 80 to 100%, including all integers values and ranges therebetween, and the diol segment is 0 to 20%, including all integers values and ranges therebetween, of the total mole percent.

A polymer of the present disclosure can form a nanoparticle. Accordingly, the present disclosure provides a nanoparticle comprising one or more polymer of the present disclosure.

A nanoparticle can have various sizes. In various examples, a nanoparticle has a size (e.g., longest dimension) such as, for example, a diameter of 100 to 350 nm.

A nanoparticle can comprise a drug. A drug is sequestered in the nanoparticle. In various examples, a drug is encapsulated in (e.g., in the hydrophobic portion of) a nanoparticle. Examples of drugs include, but are not limited to, hydrophobic drugs. Examples of hydrophobic drugs include, but are not limited to gambogic acid (including derivatives and analogs thereof), doxorubicin (DOX), camptothecin, and paclitaxel.

Various amounts of drugs sequestered in (e.g., loaded in) a nanoparticle. In various examples, a nanoparticle has a loading of 10 to 15 wt % of a drug, including all integer values and ranges therebetween. In another example, the nanoparticle has a loading of 8 to 17 wt % of a drug, including all integer values and ranges therebetween. In various examples, the nanoparticle is cationic. In other examples, the amount of PEG is increased. In other examples, the amount of PEG is decreased.

In an aspect, the present disclosure provides compositions comprising one or more polymer and/or nanoparticle of the present disclosure. The compositions can be used to deliver a drug to an individual. The compositions may comprise one or more pharmaceutically acceptable carrier.

The compositions can include one or more standard pharmaceutically acceptable carriers. The compositions can include solutions, suspensions, emulsions, and solid injectable compositions that are dissolved or suspended in a solvent before use. The injections can be prepared by dissolving, suspending or emulsifying one or more of the active ingredients in a diluent. Examples of diluents are distilled water for injection, physiological saline, vegetable oil, alcohol, and a combination thereof. Further, the injections can contain stabilizers, solubilizers, suspending agents, emulsifiers, soothing agents, buffers, preservatives, etc. The injections, are sterilized in the final formulation step or prepared by sterile procedure. Pharmaceutical compositions of the instant disclosure can also be formulated into a sterile solid preparation, for example, by freeze-drying, and can be used after sterilized or dissolved in sterile injectable water or other sterile diluent(s) immediately before use. Non-limiting examples of pharmaceutically acceptable carriers can be found in: *Remington: The Science and Practice of Pharmacy* (2005) 21st Edition, Philadelphia, Pa. Lippincott Williams & Wilkins.

In aspect the disclosure provides products, e.g. articles of manufacture, which comprise pharmaceutical preparations containing any one or any combination of the polymers, nanoparticles, and compositions described herein. In an example, a kit comprises any one or any combination of the polymers, nanoparticles, and compositions described herein.

In an example, the instant disclosure includes a closed or sealed package that contains the pharmaceutical preparation. In certain embodiments, the package can comprise one or more closed or sealed vials, bottles, blister (bubble) packs, or any other suitable packaging for the sale, or distribution, or use of the pharmaceutical compounds and compositions comprising them. The printed material can include printed information. The printed information can be provided on a label, or on a paper insert, or printed on the packaging material itself. The printed information can include information that identifies the compound in the package, the amounts and types of other active and/or inactive ingredients, and instructions for taking the composition, such as the number of doses to take over a given period of time, and/or information directed to a pharmacist and/or another health care provider, such as a physician, or a patient. The printed material can include an indication that the pharmaceutical composition and/or any other agent provided with it is for treatment of cancer and/or viral infections and/or any disorder associated with cancer and/or viral infections. In examples, the product includes a label describing the contents of the container and providing indications and/or instructions regarding use of the contents of the container to treat any cancer and/or viral infection.

In an aspect, the present disclosure provides methods that use the polymers and/or nanoparticles of the present disclosure. In various examples, the present disclosure provide methods of administering a drug to an individual. The present disclosure provides methods of using one or more compounds of the present disclosure. For example, the compounds can be used to treat cancer and/or viral infections.

In various example, a method of administering a drug to an individual (e.g., an individual in need of treatment) comprises administering to an individual a nanoparticle of the present disclosure (e.g., a nanoparticle formed from a polymer of the present disclosure, wherein the nanoparticle comprises a drug sequestered in the nanoparticle.

In various examples, the present disclosure provides a method of treating cancer and/or a viral infection comprising administering to an individual who has cancer and/or a viral infection a drug (e.g., a therapeutically effective amount of a drug) or a composition comprising a drug of the present disclosure.

Compositions comprising the compounds described herein can be administered to an individual using any known method and route, including oral, parenteral, subcutaneous, intraperitoneal, intrapulmonary, intranasal and intracranial injections. Parenteral infusions include intramuscular, intravenous, intraarterial, intraperitoneal, and subcutaneous administration. Topical and/or transdermal administrations are also encompassed.

The methods can be carried out on various individuals. Accordingly, the methods can be used for human and veterinary purposes. In various examples, an individual is a human or non-human mammal. Examples of non-human mammals include, but are not limited to mice, rats, dogs, cats, cows, pigs, sheep, and the like.

The method can be carried out in an individual who has been diagnosed with or is suspected of having cancer and/or a viral infection (i.e., therapeutic use). A method can also be carried out in individuals who have a relapse or a high risk of relapse after being treated for cancer and/or a viral infection. A method can be carried out in an individual in need of prophylaxis for viral infections/illnesses.

The present nanoparticles and compositions comprising the nanoparticles can be used to augment the macrophage response (e.g., towards cancer cells) and hence provide the synergy of the cytotoxicity of the impregnated hydrophobic anticancer drugs.

The steps of the methods described in the various embodiments and examples disclosed herein are sufficient to carry out the methods of the present disclosure. Thus, in an example, a method consists essentially of a combination of steps of the methods disclosed herein. In another example, a method consists of such steps.

The following examples are presented to illustrate the present disclosure. They are not intended to be limiting in any matter.

EXAMPLE 1

This example provides a description of polymers and nanoparticles of the present disclosure, and methods of making and using polymers and nanoparticles of the present disclosure.

Gambogic acid (GA) is a nature compound exhibiting a broad spectrum of anticancer activity and low chemotoxicity to normal tissues. However, poor aqueous solubility and sensitivity to hydrolysis that makes its pharmaceutical applications a challenge. In order to overcome these drawbacks, linear and branched Arg-based poly(ester urea urethane)s (Arg-PEUUs), folate (FA) conjugated Arg PEUUs (FA-Arg-PEUUs) and their self-assembled nanoparticles (NPs) were designed, synthesized and studied as the potential GA carriers for cancer treatment. The average diameters of linear or branched Arg-PEUU/FA-Arg-PEUU NPs are from 98 to 267 nm, and zeta potential of +12.2 to +5.4 mV. Blank FA-Arg-PEUU NPs adhered onto and were internalized into HeLa and A549 cells, and showed no cytotoxicity. The GA loading efficiency in the NP carriers ranged from 40 to 98%, depending on the feed weight ratio of GA to Arg-PEUU, and the Arg-PEUU polymer structure (i.e., linear vs. branched). About 80-90% of the loaded GA in linear and branched FA-Arg-PEUU NPs was released in 60 h in vitro. The GA at 2 µg/mL concentration delivered by the FA-Arg-PEUU NP carriers led to a higher cytotoxicity and induced a higher apoptosis percentage against folate receptor (FR) overexpressed HeLa or HCT116 than Arg-PEUU NPs. FR-negative A549 cells was used for comparison to evaluate the role of the FA as targeting ligand. When compared to the free GA treatment, the GA loaded in the FA-Arg-PEUU NP carriers also led to significant loss of the mitochondrial membrane potential in a higher percentage of the cancer cell population and more DNA fragmentation. The GA loaded in FA-Arg-PEUU NP carriers at as low as 0.6 µg/mL GA concentration can also reduce more matrix metalloproteinases (MMP-2 and MMP-9) activity of cancer cells than free GA at the same concentration, suggesting that GA-loaded Arg-PEUU NPs may have greater potential to reduce cancer cell invasion and metastasis than the free GA.

In this example, FA-decorated linear and branched Arg-based poly(ester urea urethane)s (FA-Arg-PEUUs) and their self-assembled NPs were designed, synthesized, characterized and studied as GA carriers. The internalization and anticancer activity of the GA-loaded Arg-PEUU NPs were investigated in both HeLa (FR overexpressed cell line) and A549 human lung cancer cells (FR deficiency cell line commonly used for comparison with HeLa in vitro to test the targeting function of folate conjugated materials).

Experimental Section

Materials. L-Arginine hydrochloride (L-Arg-Cl) (Alfa Aesar, Ward Hill, Mass.), 1,4-butanediol (Alfa Aesar, Ward Hill, Mass.), p-toluene sulfonic acid monohydrate (TsOH·H$_2$O) (JT Baker, Philipsburg, N.J.), glycerol α-monoallyl ether (GAE, TCI, Portland, Oreg.), triethylamine (TEA) (99%, EMD Chemical, Darmstadt, Germany), hexamethylene diisocyanate (HDI) and methanesulfonyl chloride (Acros organics, Geel, Belgium) were used for the polymer synthesis. Stannous 2-ethyl-hexanoate, sodium bicarbonate, N,N-dicyclohexylcarbodiimide (DCC), polyethylene glycol (PEG, $M_n$ 3,400) and pentaerythritol were purchased from Sigma (St. Louis, Mo.). Cysteamine was purchased from TCI, Portland, Oreg. Gambogic acid was purchased from BroadPharm, San Diego, Calif. Thiazolyl blue tetrazolium bromide, N-hydroxysuccinimide (NETS) and 4% paraformaldehyde in PBS were purchased from Alfa Aesar, Ward Hill, Mass. Solvents like toluene, chloroform (VWR Science, West Chester, Pa.), dimethyl sulfoxide (DMSO), N, N-dimethylformamide (DMF), aqueous ammonia (Mallinckrodt incorporated, St. Louis, Mo.), anhydrous ethyl alcohol (PHARMCO-AAPER, CT), ethyl ether (Fisher Chemical, Rockford, Ill.), isopropyl alcohol (ACS, 99.5%, Macron Chemicals, Philipsburg, N.J.) tetrahydrofuran (THF) and ethyl acetate (BDH, London, UK) were used without further purification. The snakeskin dialysis tubes (molecular weight cutoff (MWCO): 3,500 g/mol and 10,000 g/mol) and NHS-rhodamine (Ex/Em: 552/575 nm) were purchased from Thermo Fisher Scientific, Rockford, Ill. Prolong® Gold anti-fading mounting reagent with DAPI was purchased from Life Technologies, CA, USA.

Synthesis of Arg-PEUU with PEG3400 spacer. To improve the availability of FA for receptor-binding, PEG spacer was introduced to link FA to the Arg-PEUU polymer. The synthesis method of diaminopolyethylene glycol 3400 (PEG3400-NH$_2$) is described elsewhere. Linear Arg-PEUU was synthesized using the prior reported method with modifications on building block feed ratio (Table 1.).

In order to provide more polymer end groups for FA conjugating, branched Arg-PEUU was prepared by a core-first method. In a typical synthesis of branched Arg-PEUU, 1 mmol pentathritol (0.136 g) and 25 mmol HDI (4.2 g) were magnetically stirred in 10 mL DMSO with stannous 2-ethylhexanoate catalyst (1 wt % of total mass of reactants). The mixture was allowed to react at 45° C. for a period of 40 min in a dry nitrogen atmosphere with magnetic stirring. 2 mmol GAE (0.264 g) and 18 mmol Arg-4-Cl diester (14.3 g) in 50 mL DMSO were then added to the prepolymer solution, and the reaction was continued at 45° C. for another 8 h. In the end group capping step by PEG3400-NH$_2$, 2.5 mmol PEG3400-NH$_2$ (8.5 g) in 30 mL DMSO was added and the reaction was continued for 6 h. The crude Arg-PEUU-PEG3400 product was precipitated in THF, dried and redissolved in DMF, then purified by dialysis (3 L, 8 h; MWCO: 3,500 g/mol) six times against DI water at room temperature. The precipitate product was collected and dried in vacuo. The feed ratios of the building blocks in the synthesis of linear and branched Arg-PEUU are listed in Table 1.

Synthesis of folate-PEG-Arg-PEUUs (FA-Arg-PEUUs). Folate N-hydroxysuccinimidyl ester (FA-NHS) was prepared according to the published procedures. Briefly, 1.0 g FA was dispersed in 2 mL acetonitrile, then was mixed in 40 mL DMSO and 0.5 mL TEA. After addition of NHS (0.52 g 2.2 equiv.) and DCC (0.5 g, 1.1 equiv.), the mixture was stirred in the dark for 18 h. Insoluble dicyclohexylurea (DCU) precipitation was removed by filtration. 250 mL of 30% acetone in ethyl ether was then added while stirring. The yellow FA-NHS precipitate was collected on sintered glass funnel, washed with acetone and ethyl ether, dried and was used immediately in the next synthesis step of conjugating onto Arg-PEUU with capped PEG3400 polymer end.

FA-NHS was coupled to Arg-PEUU as follows: 400 mg FA-NHS was dissolved in 5 mL DMSO and then added into 2.6 g Arg-PEUU in 10 mL DMSO, in the presence of TEA (30 µL); the mixture was then stirred overnight in the dark at room temperature. The FA-tagged Arg-PEUU product was purified by dialysis (3 L, 4 h; MWCO: 3,500 g/mol) twice against 0.05 M NaHCO$_3$ aqueous solution, and subsequently twice against DI water (3 L, 6 h; MWCO: 3,500 g/mol). The chemical structures of both linear and branched FA-Arg-PEUU are shown in FIG. 1. The contents of the FA on FA-Arg-PEUUs were measured by dissolving FA-Arg-PEUU to 0.5 mg/mL solution in DMSO. FA amounts incorporated into Arg-PEUUs were determined by a UV absorption at 365 nm wavelength in a quartz cuvette. Corresponding linear or branched Arg-PEUU-PEG 3400 at 0.5 mg/mL in DMSO was used as the references. Serially diluted concentrations of FA in DMSO were used to construct a calibration curve from 12.5-100 µg/mL.

Preparation of rhodamine labeled FA-Arg-PEUUs. The pendant double bonds on the segment B of FA-Arg-PEUU were converted to amine groups by adding cysteamine to create the amino reaction site for rhodamine conjugation as described in prior studies. 300 mg cysteamine was added into 20 wt % FA-Arg-PEUU (5 g) DMSO solution in a glass flask equipped with a magnetic stirring bar. The flask was heated in a 70° C. oil bath overnight. The resulting product was precipitated out by adding cold ethyl acetate, filtering, vacuum drying and purification by dialysis against DI water (3 L, 6 h; MWCO: 3,500 g/mol) four times. After being dried in vacuo, 1 g FA-Arg-PEUU with pendant amine group and 10 mg NHS-rhodamine were dissolved in 5 mL DMSO, then protected from light and stirred at room temperature for 10 h. The solution was then dialyzed in the dark against DI water (2 L, 6 h; MWCO: 3,500 g/mol). Rhodamine labeled FA-Arg-PEUU was collected by lyophilizing the suspension in the dialysis tube.

Characterizations of FA-Arg-PEUUs. Fourier transform infrared (FTIR) spectra of FA-Arg-PEUUs were recorded on a PerkinElmer (Madison, Wis.) Nicolet Magna 560 FTIR spectrometer with Omnic software for data acquisition and analysis. All solubility tests (in DI water, DMF, DMSO, ethanol, methanol, chloroform, THF, ethyl acetate, acetone) were performed at room temperature. Gel permeation chromatography (GPC) of Arg-PEUU was tested on a Waters Agilent GPC equipped with a Waters 2414 differential RI detector and Waters 2998 Photodiode Array Detector (PDA) in the Materials Research Laboratory at University of California, Santa Babara. Visco Gel I-series columns (IM-BHMW-3078, Viscotek, 7.8 mm×30 cm) were used. DMF (contained 0.1% lithium bromide) was used as an eluant (flow rate 1 mL/min) at temperature of 25° C. A WATERS Alliance HPLC 2695 separation pump was used with 100 µL injection volume. Polystyrene standards were used for calibration. The glass transition temperature ($T_g$) of Arg-PEUU was measured by a TA Q2000 differential scanning calorimetry (DSC) under a nitrogen gas flow 50 mL/min.

Preparation of GA-loaded Arg-PEUU and FA-Arg-PEUU NPs. GA-loaded Arg-PEUU NPs was prepared by a facile dialysis method. Predetermined amounts of GA was mixed with 1 mg/mL Arg-PEUUs in DMSO and dialyzed against DI water three times (3 L, 6 h; SnakeSkin™ dialysis tubing, MWCO: 3,500 g/mol) at room temperature. The Arg-PEUU NP suspension was formed in the dialysis tube. FA-Arg-PEUU and rhodamine-tagged FA-Arg-PEUU NPs were also prepared using the same dialysis method but in the dark environment. The resulting GA-loaded Arg-PEUU or FA-Arg-PEUU NPs in the dialysis bag was lyophilized and stored at 4° C.

Transmission electron microscopy (TEM) of Arg-PEUU NPs. TEM images were recorded on a FEI T12 SPIRIT microscope at 120 kV equipped with a LaB6 filament and SIS Megaview III CCD camera. Samples were prepared by dropping 1 mg/mL Arg-PEUU or FA-Arg-PEUU NP suspension in water onto a copper grid (200 mesh coated with carbon), and the water was sucked up using a piece of filter paper at the edge of the copper grid. Phosphomolybdic acid was used to stain Arg-PEUU NP to enhance their electron contrast.

Arg-PEUU NP size and zeta potential characterization. The size and zeta potential of the Arg-PEUU NP were measured at 25° C. using a Malvern Zetasizer Nano-ZS machine (Worcestershire, UK). 1 mg/mL Arg-PEUU NP suspension samples were placed in 1.0 mL plastic cuvettes. The average hydrodynamic radius of the Arg-PEUU NP in solution was measured by using a light scattering to measure. Zeta potentials were calculated by using the Smoluchowsky model for aqueous suspensions.

The loading efficiency (LE) and drug loading content (LC). The LE and LC of the GA-loaded Arg-PEUU NPs were measured in DMSO by using a UV-Vis spectrophotometer (PerkinElmer Lambada 35, Madison, Wis.). The GA contents in 5 mg, lyophilized Arg-PEUU NPs was extracted by fast stirring in 30 mL ethanol for 2 h at 40° C. The ethanol solution was cooled to room temperature then filtered using 0.2 µm Nylon filter (VWR, West Chester, Pa.) and collected in clean glass vials. Ethanol was dried in vacuum oven at room temperature. The GA in the glass vials was redissolved in 20 mL DMSO. The concentration of GA in DMSO was determined by the absorption at 360 nm wavelength (quartz cuvette). The GA content was calculated from the calibration curve over the linear range from 1 to 100 µg/mL.

$$LE = \frac{\text{mass of GA loaded in NPs}}{\text{mass of GA used during the NP preparation}} \times 100$$

$$LC = \frac{\text{mass of GA loaded in NPs}}{\text{mass of the NPs with loaded GA}} \times 100$$

In vitro release of GA from FA-Arg-PEUU NPs. The in vitro release profiles of GA from linear and branched FA-Arg-PEUU NPs were investigated using dialysis bags (MWCO: 10,000 g/mol) at 37° C. Briefly, 10 mg of GA-loaded FA-Arg-PEUU NPs (20 wt % GA initial loading) was suspended in 5 mL of DI water and poured into a dialysis bag. The dialysis bags were immersed in 50 mL of 0.05 M pH 7.4 PBS buffer in capped glass bottles, which were placed in a shaking incubator at 37° C. (Julabo, water bath). At predetermined time intervals, three 1 mL solution samples were taken from the release medium and 3 mL of fresh PBS was added to maintain a constant volume. The concentration of GA released into the buffers was measured using a UV-Vis spectrophotometer at 360 nm.

Confocal image analysis of cellular uptake. HeLa and A549 cells were maintained in DMEM with 10% FBS and 1% penicillin-streptomycin. HeLa and A549 cells were seeded on the circular coverslip in 24-well plates at a density of $2 \times 10^4$ cells/well and incubated for 24 h at 37° C. For cellular internalization observation, cells were incubated along with various rhodamine-labeled Arg-PEUU NPs at a concentration of 100 µg/mL in the media. After incubation for 4 h at 37° C., cells were washed twice with ice cold PBS and fixed with fresh 4% paraformaldehyde in PBS for 30 min at room temperature. The coverslips were then mounted on glass microscope slides with a drop of anti-fading mounting agent with DAPI. Samples were kept in a dark environment at 4° C. overnight before imaging. The cellular uptake was visualized using confocal laser scanning microscopy (Carl Zeiss LSM 710, Germany).

Quantitative NP uptake study by flow cytometry. HeLa and A549 cells were seeded on 6-well plates at a density of $5 \times 10^5$ cells/well. After 24 h incubation, the cells were treated with various rhodamine-labeled Arg-PEUU NPs (100 µg/mL) at 37° C. for 4 h. After incubation, medium was removed and cells were harvested. The cells were washed with PBS and collected by centrifugation (200 rcf, 5 min) twice followed by flow cytometric analysis (BD FACS Aria Fusion flow cytometry) immediately. The mean fluorescence intensity of $1 \times 10^4$ cells was recorded for each sample.

Cytotoxicity assay of GA-loaded Arg-PEUU NPs. The cytotoxicity of GA-loaded Arg-PEUU NPs (20 wt % initial loading) against HeLa and A549 was evaluated by MTT assay. The cells were seeded onto 96-well plates at a density of $7 \times 10^3$ cells/well and incubated for 24 h. 200 µg/mL GA stock solution in DMSO was diluted in complete cell culture media to 2 concentration (2 µg/mL, 6 µg/mL) as free GA treatments. Calculated amount of GA-loaded into the Arg-PEUU NPs was weighed and suspended in cell culture media to achieve 2 or 6 µg/mL GA concentration. Free GA, blank FA-Arg-PEUU NPs, and GA-loaded Arg-PEUU NPs were incubated with cells for 5 or 12 h at 37° C. The media were then removed after incubation and cells were washed twice with PBS. Afterward, the cells were incubated with MTT (20 µl per well, 5 mg/mL) in 100 µL media for 4 h at 37° C. The supernatant was then removed before adding DMSO (150 µL per well) into the wells. The optical absorbance of the DMSO solution in the 96 well plate was then measured at wavelengths of 570 nm and 690 nm (Spectramax plus 384, Molecular Devices, USA). The cell viability (%) was calculated according to the following equation:

$$\text{Viability}(\%) = \frac{OD570(\text{sample}) - OD690(\text{sample})}{OD570(\text{control}) - OD690(\text{control})} \times 100$$

where OD570 (control) and OD690 (control) represent the measurements from the wells treated with cell medium only, and OD570 (sample) and OD690 (sample) are measurements from the wells treated with blank FA-Arg-PEUU NPs, free GA, and various GA-loaded Arg-PEUU and FA-Arg-PEUU NPs. 8 samples of each type of treatment were analyzed.

Cellular apoptosis studies performed by flow cytometry. 200 µg/mL GA stock solution in DMSO was diluted to 2 µg/mL in a complete cell culture medium (McCoy's 5A medium for HCT116, DMEM for A549) to be used as the free GA treatment without carriers. $5 \times 10^5$/well HCT116 (a FR-positive human colon cancer cell line was used as a substitute for HeLa) or A549 cells were cultured for 24 h in 6 well plates, then were washed with PBS and incubated with fresh media containing 2 µg/mL free GA, 20 µg/mL blank branched FA-Arg-PEUU NPs, and GA-loaded branched FA-Arg-PEUU NPs (20 wt % GA initial loading at the equivalent amount of the free GA). Apoptosis was assessed using staining with Annexin V-FITC/PI apoptosis detection kit (Affymetrix, CA) according to the manufacturer's instruction followed by flow cytometry analysis. HeLa is not suggested for Annexin V-FITC/PI test because specific membrane damage may occur during the cell harvesting, and annexin v-FITC/PI staining of HCT 116 was reported in many studies. However, HeLa shares the same culture media and environment as A549 cells, hence used for other GA drug effect studies, including mitochondrial membrane potential change, DNA fragmentation and matrix metalloproteinases activity etc.).

Determination of mitochondrial membrane potential ($\Delta\Psi m$) change. The effects of 2 µg/mL free GA, blank Arg-PEUU NPs, and GA-loaded Arg-PEUU NPs on $\Delta\Psi m$ of HeLa and A549 cells were measured using the mitochondrion-specific lipophilic cationic probe, fluorochrome JC-1 (5',6,6'-tetrachloro-1,1',3,3'-tetraethylbenzimidazolylcarbocyanine iodide; Adipogen, San Diego, Calif.) as described previously. $8\times10^5$ HeLa and A549 cells were incubated with free GA, blank Arg-PEUU NPs and GA-loaded Arg-PEUU NPs for 24 h. 50 µM CCCP in media (carbonyl cyanide 3-chlorophenylhydrazone, Cayman chemical, MI) was used as the positive control to confirm the JC-1 response. After treatment, the cells were incubated with JC-1 dye for 20 min, washed with PBS, and analyzed by flow cytometry.

DNA fragmentation. DNA fragmentations induced by free GA and GA-loaded Arg-PEUU NPs were assayed using the apoptotic DNA ladder Detection kit (Takara Bio, Shiga, Japan). Briefly, $2\times10^6$ cells were cultured in individual flasks and incubated with free GA (2 µg/mL), GA loaded in Arg-PEUU NPs (at an equivalent GA concentration of 2 µg/mL in linear or branched Arg-PEUU or FA-Arg-PEUU NPs) for 48 h. Cells were then collected and the fragmented DNA was extracted according to the manufacturer's instructions. The extracted fragmented DNA was dissolved in TE buffer, separated and visualized on Flashgel™ system (Lonza, Switzerland).

Gelatin zymography. Gelatin zymography was used to examine the effect of the GA-loaded Arg-PEUU NPs on matrix metalloproteinases (MMP) activity. $9\times10^5$ HeLa or A549 cells were seeded and then incubated in 1.5 mL serum-free DMEM for 16 h with 0.6 µg/mL concentrations of GA or equivalent GA content in the GA-loaded Arg-PEUU NP carriers. The media supernatants were centrifuged (400 rcf, 5 min, 4° C.), collected and mixed with sample buffer, and gelatin zymography was performed as described previously. In brief, SDS-PAGE gels were prepared containing 1% type B gelatin (w/v). After electrophoresis, the gels were washed with 2.5% Triton X-100 (v/v) for 10 min three times to remove SDS and followed by washing with developing buffer (50 mM Tris-HCl buffer containing 10 mM of $CaCl_2$), 0.02% $NaN_3$, pH 7.6) for 30 min. The gels were then incubated at 37° C. for 16 h in the fresh developing buffer. The gels were staining with 0.25% Coomassie Brilliant Blue R-250 staining solution and the destained with the acetic acid/ethanol/water=1/4/5 solution. Enzyme digested regions were observed as white bands against a blue background.

Statistical analysis. All data are presented as mean values with standard deviations (SD). Statistical analysis was performed with one-way ANOVA test, and $p<0.05$ was considered statistically significant.

Discussion.

Figure 2:
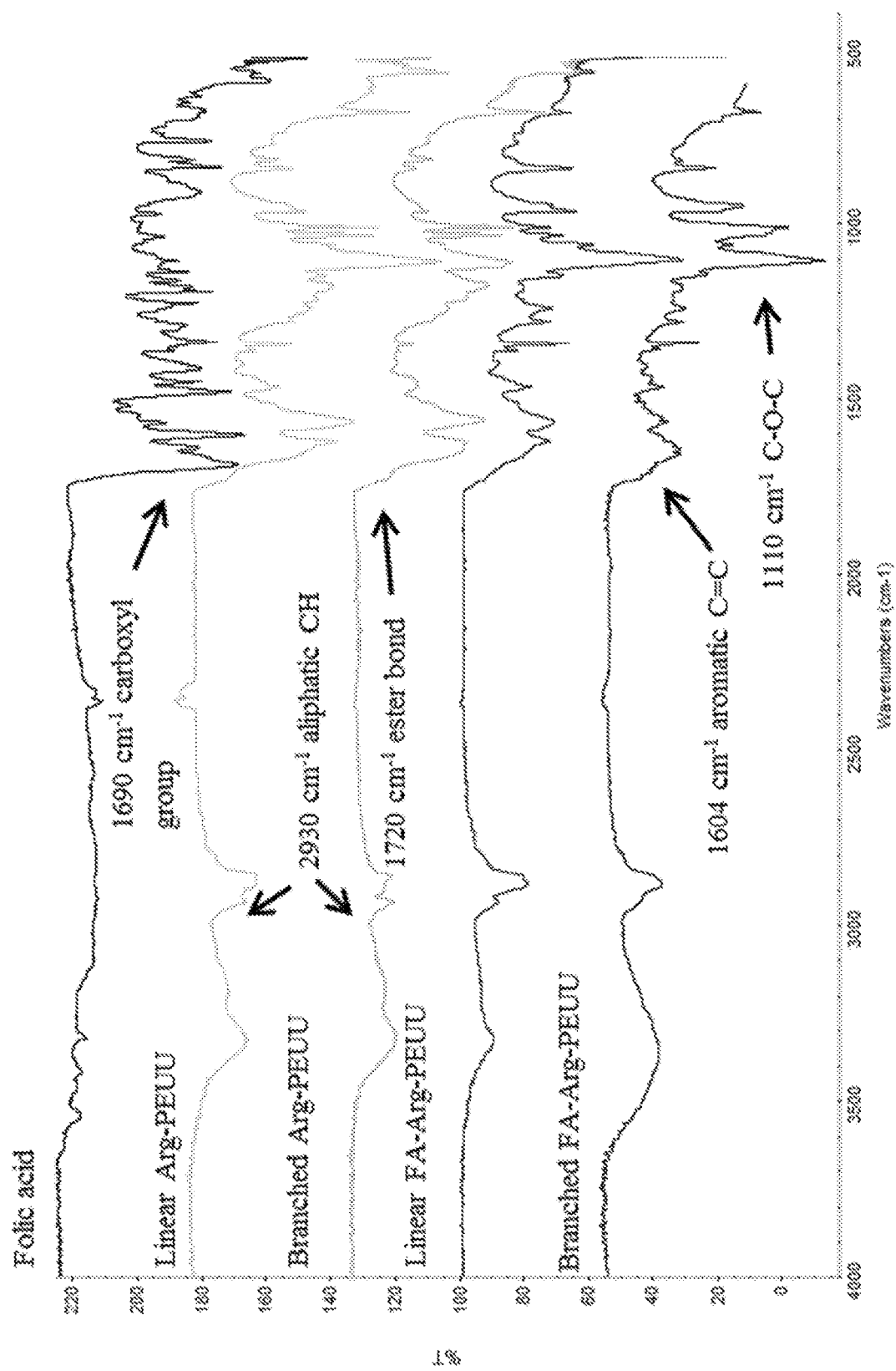
FIG. 2 shows FTIR spectra of Arg-PEUU, FA-Arg-PEUU and folic acid.

Synthesis and characterization of Arg-PEUU and FA-Arg-PEUU polymers. FT-IR data were obtained to verify the chemical composition of the newly synthesized FA-Arg-PEUUs (FIG. 2). The presence of an aromatic peak (1604 $cm^{-1}$) at the FT-IR spectrum of FA-Arg-PEUU demonstrates the presence of FA when comparing with the Arg-PEUU. The FA spectrum showed peak at 1690 $cm^{-1}$ (carboxyl group), while the Arg-PEUU showed characteristic bands of ester bond at 1720 $cm^{-1}$. The absorbance at 1110 $cm^{-1}$ on the Arg-PEUUs and FA-Arg-PEUU indicate the presence of the C—O stretch of ether bond that comes from the PEG composition. Conjugated FA concentration on linear and branched FA-Arg-PEUU was measured by UV absorption at 365 nm. Each gram of linear or branched FA-Arg-PEUU has 0.11 or 0.21 mM FA, respectively (Table 1.). Branched Arg-PEUU polymer structure improved 91% FA density on the Arg PEUU which may improve targeting effect of FA.

As shown in Table 1, the number average molecular weights ($M_n$) of linear and branched Arg-PEUUs from GPC data are 18,430 and 25,530 g/mol, while the polydispersity (PDI) are 1.73 and 2.26, respectively. The relatively higher PDI is believed to be attributed to the multiple additions of the monomers into the reaction. There is no obvious $T_g$ difference between the linear and branched FA-Arg-PEUUs, −19.08° C. vs. −19.15° C.

Compared to the prior published $T_g$ data of Arg-PEUUs and Arg-Leu PEUUs which ranged from −3.4° C. to −9.7° C., the incorporation of PEG3400 composition into Arg-PEUU in the current study led to a much lower $T_g$ of FA-Arg-PEUUs (−19.08° C. to −19.15° C.) as the $T_g$ of PEG3400 is −41° C. (according to the manufacture's technical data). Linear and branched Arg-PEUU and the FA-conjugated counterparts are not aqueous soluble, but soluble in DMF or DMSO (Table 2.).

TABLE 1

Molecular weight, glass transition temperature of linear and branched Arg-PEUUs

| Arg-PEUUs | Building blocks | Molar feed ratio of the building blocks | $M_n$ (g/mol) | $M_w$ (g/mol) | PDI | $T_g$ (° C.) | FA content in 1 gram FA-Arg-PEUU (mM) |
|---|---|---|---|---|---|---|---|
| Linear Arg-PEUU | Arg-4-Cl, GAE, HDI, PEG3400-NH$_2$ | 9:1:11:2 | 18,430 | 31,880 | 1.73 | −19.08 | 0.11 |
| Branched Arg-PEUU | Pentaerythriol, Arg-4-Cl, GAE, HDI, PEG3400-NH$_2$ | 1:18:2:25:2 | 25,530 | 57,700 | 2.26 | −19.15 | 0.21 |

TABLE 2

Solubility of linear and branched Arg-PEUU in common solvents

| Sample/solvent | H$_2$O | DMF | DMSO | Ethanol | Methanol | Chloroform | THF | Ethyl acetate | Acetone |
|---|---|---|---|---|---|---|---|---|---|
| Linear Arg-PEUU | − | + | + | − | − | − | − | − | − |
| Branched Arg-PEUU | − | + | + | − | − | − | − | − | − |

TABLE 2-continued

Solubility of linear and branched Arg-PEUU in common solvents

| Sample/solvent | H₂O | DMF | DMSO | Ethanol | Methanol | Chloroform | THF | Ethyl acetate | Acetone |
|---|---|---|---|---|---|---|---|---|---|
| Linear FA-Arg-PEUU | - | + | + | - | - | - | - | - | - |
| Branched FA-Arg-PEUU | - | + | + | - | - | - | - | - | - |

Figure 3:
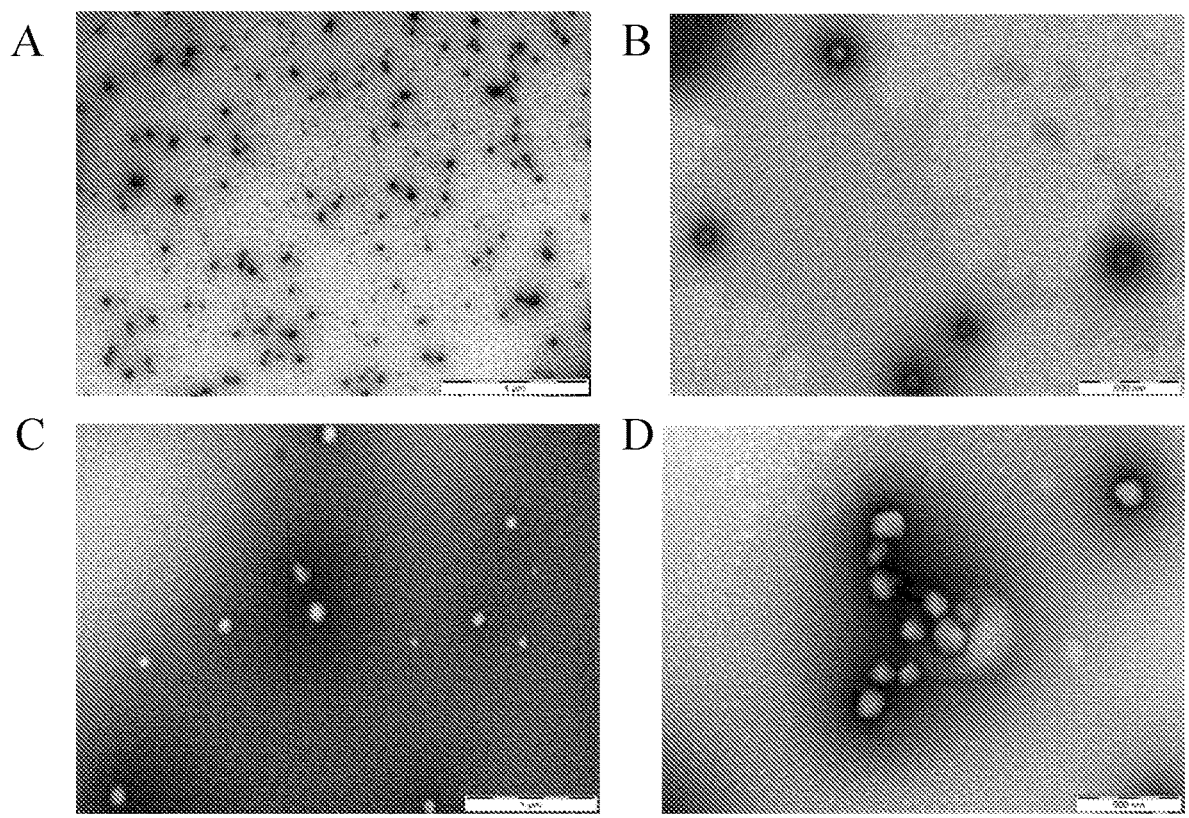
FIG. 3 shows representative TEM images of FA-Arg-PEUU NPs; (A) linear FA-Arg-PEUU NPs; (B) linear FA-Arg-PEUU NPs with 20 wt % GA initial feeding; (C) branched FA-Arg-PEUU NPs; (D) branched FA-Arg-PEUU NPs with 20 wt % GA initial feeding.

Soluble: +; Insoluble: -. Soluble is defined as >10 mg/mL solubility at room temperature Characterization of Arg-PEUU, FA-Arg-PEUU NPs and GA encapsulation. Both light scattering techniques (zetasizer) and transmission electronic microscope (TEM) were used to characterize FA-Arg-PEUU NP morphology. The branched FA-Arg-PEUUNPs had larger particle size (267.3 nm in diameter) than its linear counterpart (229.8 nm in diameter) in an aqueous environment, because branched FA-Arg-PEUU NPs have more hydrophilic PEG3400 contents (Table 3 and FIG. 3). The conjugation of PEG 3400 and FA onto Arg-PEUU also led to a larger NP size in both linear (229.8 nm vs. 98.8 nm) and branched Arg-PEUU (267.3 nm vs. 143.3 nm), and a lower positive charge (9.0 mV vs.12.2 mV for linear, and 5.4 mV vs.10.4 mV for branched) in an aqueous environment.

TABLE 3

Size and zeta potential of Arg-PEUU NPs

| Self-assembled nanoparticles | Number average diameter (nm) at 25° C. | Polydispersity | Zeta potential (mV) |
|---|---|---|---|
| Linear Arg-PEUU | 99 ± 1 | 0.29 | +12.2 ± 1.0 |
| Linear FA-Arg-PEUU | 230 ± 77 | 0.37 | +9.0 ± 2.7 |
| Branched Arg-PEUU | 143 ± 11 | 0.36 | +10.4 ± 2.1 |
| Branched FA-Arg-PEUU | 267 ± 44 | 0.39 | +5.4 ± 2.9 |

TABLE 4

GA drug loading content (LC) and loading efficiency (LE) in Arg-PEUU and FA-Arg-PEUU NPs.

| Feed weight ratio (%) | Linear Arg-PEUU | | Branched Arg-PEUU | | Linear FA-Arg-PEUU | | Branched FA-Arg-PEUU | |
|---|---|---|---|---|---|---|---|---|
| | Loading content (%) | Loading efficiency (%) | Loading content (%) | Loading efficiency (%) | Loading content (%) | Loading efficiency (%) | Loading content (%) | Loading efficiency (%) |
| 10 | 9.7 ± 2.0 | 97 ± 2 | 9.2 ± 0.5 | 92 ± 5 | 9.5 ± 0.4 | 95 ± 4 | 9.8 ± 0.6 | 98 ± 6 |
| 20 | 10.7 ± 0.6 | 53 ± 3 | 13.2 ± 0.6 | 66 ± 3 | 11.2 ± 1.2 | 56 ± 6 | 13.6 ± 0.4 | 68 ± 2 |
| 30 | 12.1 ± 0.1 | 40 ± 4 | 14.9 ± 1.8 | 50 ± 6 | 12.5 ± 2.1 | 42 ± 7 | 15.6 ± 0.9 | 52 ± 3 |

As shown in Table 4, the LE of GA in FA-Arg-PEUU NPs ranged from 40% to 98%, depending on the feed ratio of GA to the NP carrier (10 to 30 wt %) and the type of Arg-PEUU NPs (i.e., linear vs. branched). To achieve a balanced LE and LC, i.e., higher LC with adequate LE, GA-loaded FA-Arg-PEUU NPs were formulated with the 20 wt % feed ratio of GA to FA-Arg-PEUU NPs, and this formulation was used for the following tests of drug effect. The GA concentrations in all the treatments were calculated using the measured GA content in the carriers.

Figure 4:
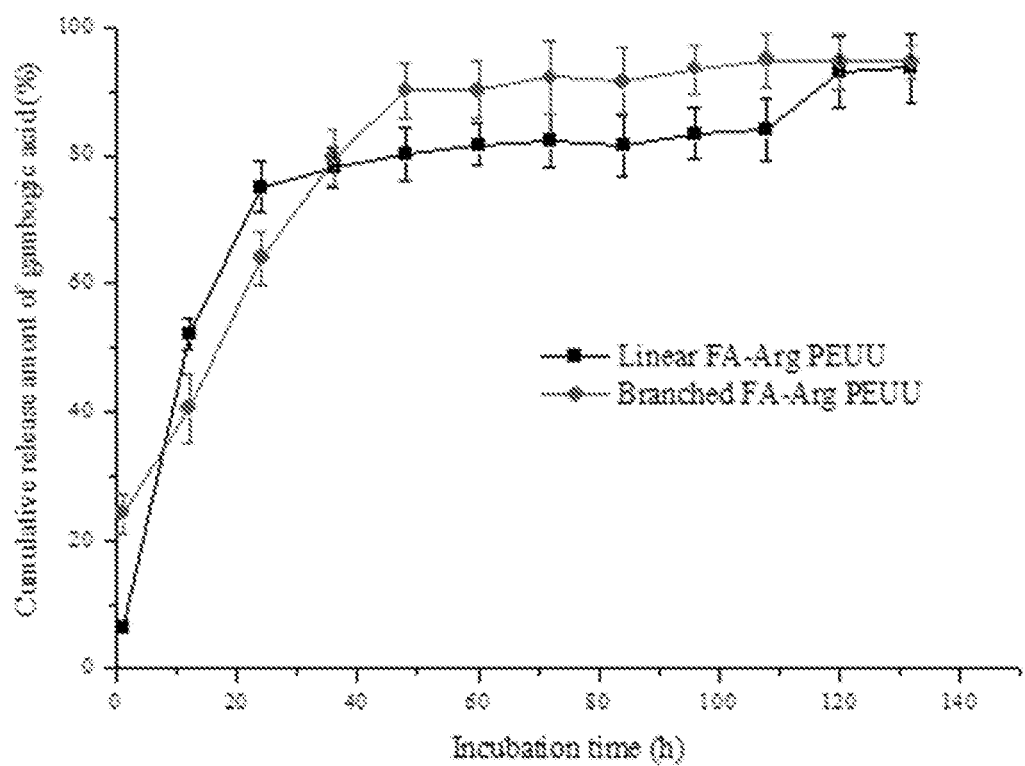
FIG. 4 shows cumulative release of GA from linear or branched FA-Arg-PEUU NPs in a 0.05 M PBS buffer, at pH 7.4, and 37° C. The GA to the FA-Arg-PEUU NPs feeding ratio is 20 wt %.

In vitro release of GA from FA-Arg-PEUU NP carriers. The in vitro release of GA from the FA-Arg-PEUU NP carriers with a 20 wt % GA initial feeding was examined at pH 7.4 PBS and 37° C. The GA release data in FIG. 4 show that the branched FA-Arg-PEUU NP carrier had a lower burst release (~40%) at 18 h but a more complete release (~90%) at 60 h when comparing to the release profile of the linear Arg-PEUU NP carrier (~50% at 18 h and ~80% at 60 h).

Adhesion and internalization of FA-Arg-PEUU NPs to HeLa and A549 cells. The FR-positive HeLa cells and FR-negative A549 cells were utilized to visualize the attachment and internalization of rhodamine-labeled GA-loaded Arg-PEUU and FA-Arg-PEUU NPs by using confocal microscope imaging and flow cytometry test. The merged fluorescent images of rhodamine and DAPI channels in FIGS. 5A, B and C provide visual evidence of the Arg-PEUU and FA-Arg-PEUU NPs (red fluorescence) adhered and engulfed by HeLa (FIG. 5A) and A549 (FIG. 5B) cells after 4 h incubation. FIG. 5C shows a representative 3D image of the internalization of the linear FA-Arg-PEUU NP inside A549 cells. FIGS. 5D and E show the quantitative rhodamine fluorescence intensity for both HeLa and A549 cells.

Figure 5:
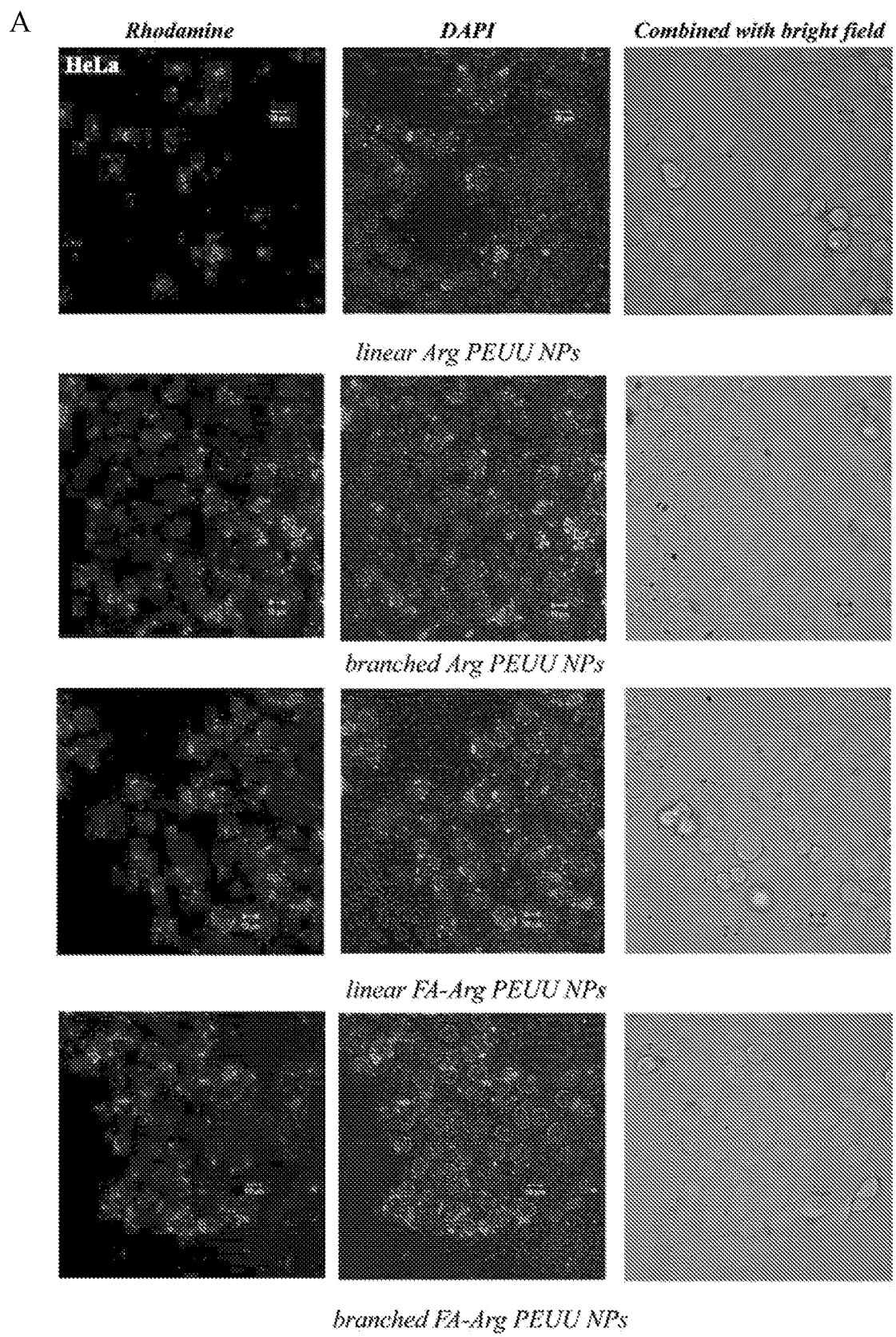
FIG. 5 shows confocal laser scanning microscopy images (CLSM) of cell uptake of rhodamine labeled Arg-PEUU and FA-Arg-PEUU NPs after 4 h (h=hour(s)) incubation at 100 µg/mL concentration at 37° C. (A) CLSM images of the uptake of the NPs in HeLa cells; (B) CLSM images of the uptake of the NPs in A549 cells; (C) representative 3D CLSM scanning of the linear FA-Arg-PEUU NP internalization in A549 cells; (D) Quantitative fluorescent intensity of rhodamine labeled Arg-PEUU and FA-Arg-PEUU NPs engulfed by HeLa cells; (E) Quantitative fluorescent intensity of rhodamine labeled GA-loaded Arg-PEUU and FA-Arg-PEUU NPs engulfed by A549 cells.
Figure 5:
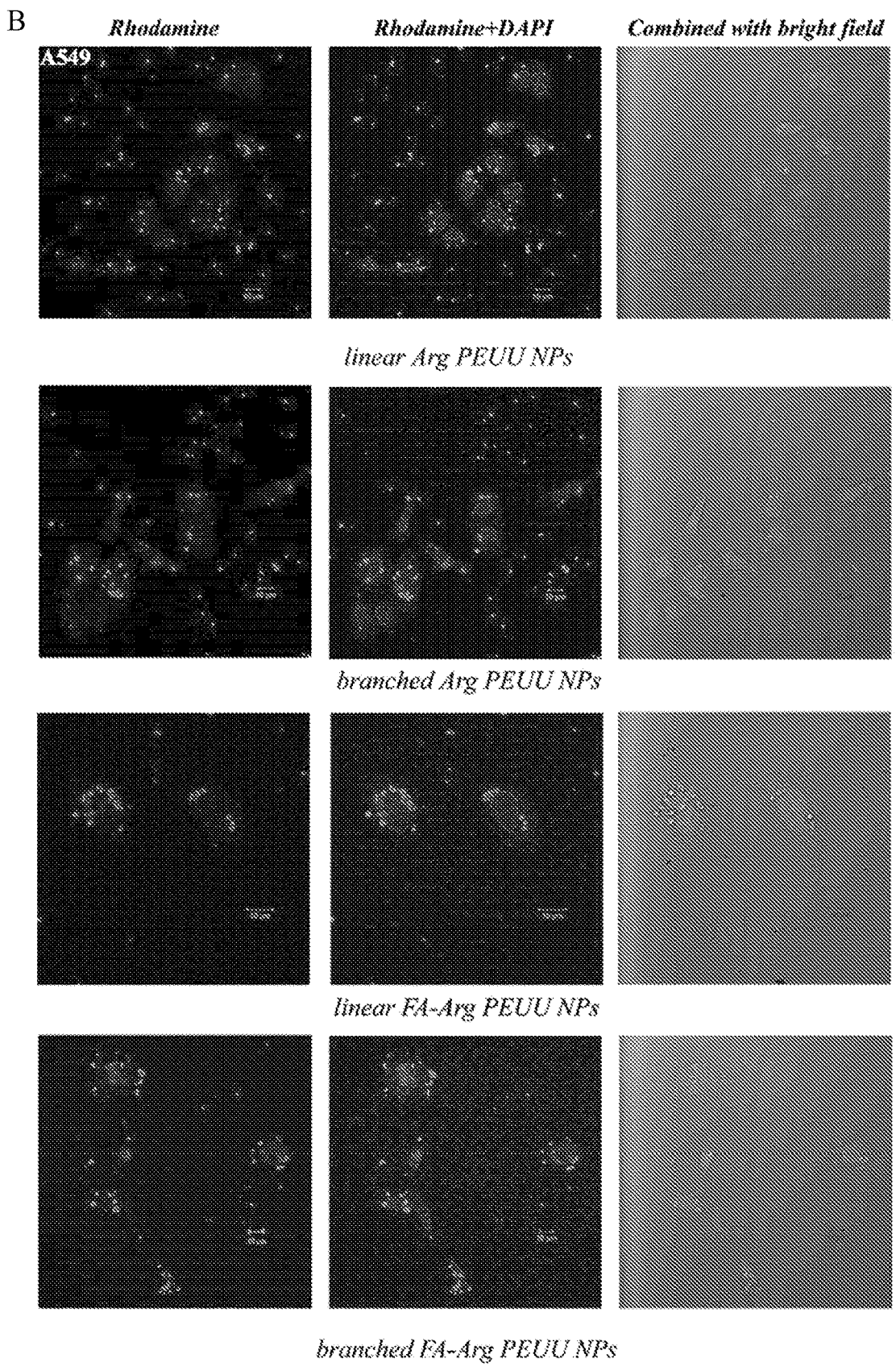
Figure 5:
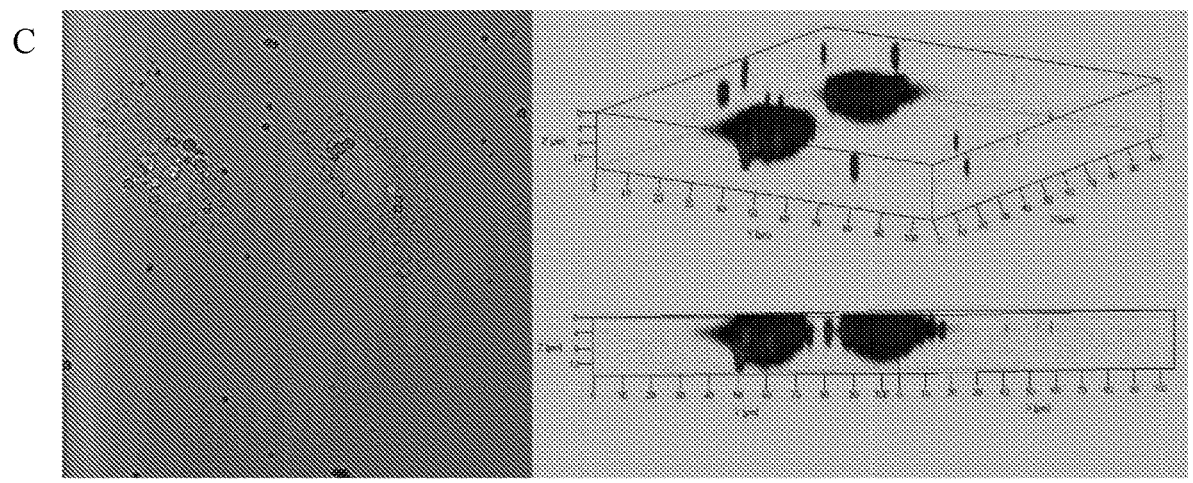
Figure 5:
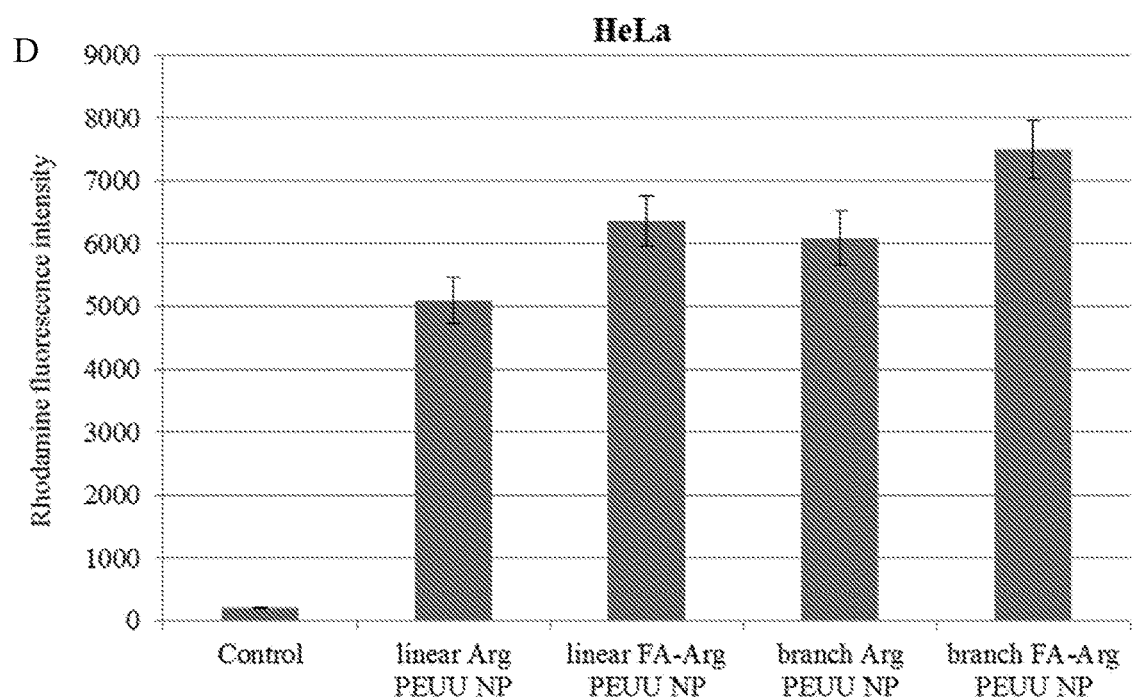
Figure 5:
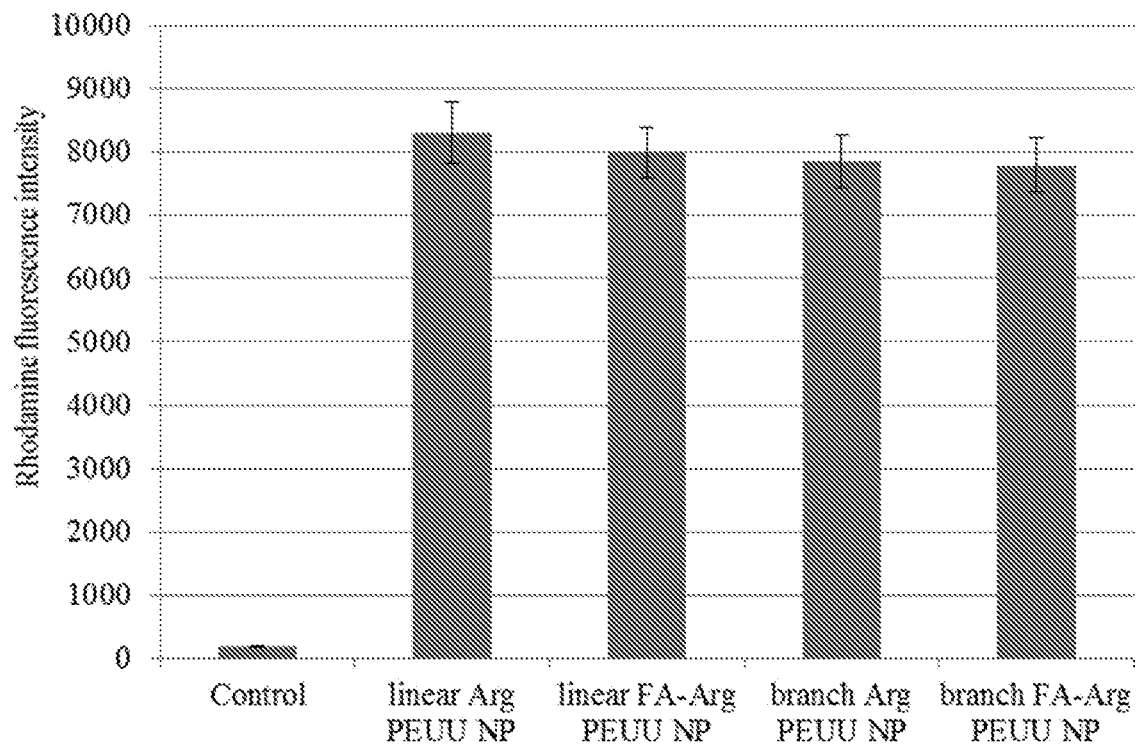

The red fluorescence of the Arg-PEUU NPs could be observed after washed with cold PBS before fixation and imaging. Most Arg-PEUU NPs are located on the perimeter of the cells. The representative 3D confocal laser scanning microscopy (CLSM) images in FIG. 5C shows that linear FA-Arg-PEUU NPs were internalized inside A549 cells. FIG. 5 D shows the quantitative rhodamine fluorescence intensity in HeLa cells after 4 h incubation with Arg-PEUU NPs as well as FA-tagged NPs. The fluorescence intensity data indicate that, when compared to the non-FA conjugated Arg-PEUU NPs treatment, HeLa cells showed 25% higher fluorescence intensity after they were treated with linear FA-Arg-PEUU NP carrier, and 23% higher fluorescence intensity after they were treated with the branched FA-Arg-PEUU NPs rather than the corresponding non-FA-tagged NPs. As shown in FIG. 5E for the A549 cancer cells, the FA-Arg-PEUU NPs did not significantly change the adhesion/internalization levels from the non-FA conjugated Arg-PEUU NPs, probably due to the lack of FA receptor on A549.

The difference in the internalization level of other published FA-conjugated polymers towards FR positive/negative cell lines was reported. The uptake of hydroxypropyl methacrylamide (HPMA) by A549 and HeLa cells was previously examined, and the data show no improved internalization in A549 cells, but an approximately 100% increased cell uptake in HeLa cells. A significant part of the cytotoxicity of GA is from its induced apoptosis through the GA/TfR interaction, hence adhesion onto the cell membrane and release GA close to transmembrane TfR vicinity may lead to an increased cytotoxicity toward cancer cells.

Cytotoxicity of GA-loaded Arg-PEUU and FA-Arg-PEUU NPs. Cytotoxicity against HeLa and A549 cells after 5 or 12 h treatment by free GA, blank FA-Arg-PEUU, GA-loaded Arg-PEUU and FA-Arg-PEUU PEUU NP carriers were evaluated by using a MTT assay. The acronym for a variety of treatments are given in Table 5 and used in all following data charts.

TABLE 5

The abbreviations of corresponding treatments.

| Sample | Abbreviation |
| --- | --- |
| blank linear FA-Arg-PEUU NPs | FL |
| blank branched FA-Arg-PEUU NPs | FB |
| free gambogic acid | GA |
| GA-loaded linear Arg-PEUU NPs | GL |
| GA-loaded branched Arg-PEUU NPs | GB |
| GA-loaded linear FA-Arg-PEUU NPs | GFL |
| GA-loaded branched FA-Arg-PEUU NPs | GFB |

Figure 6:
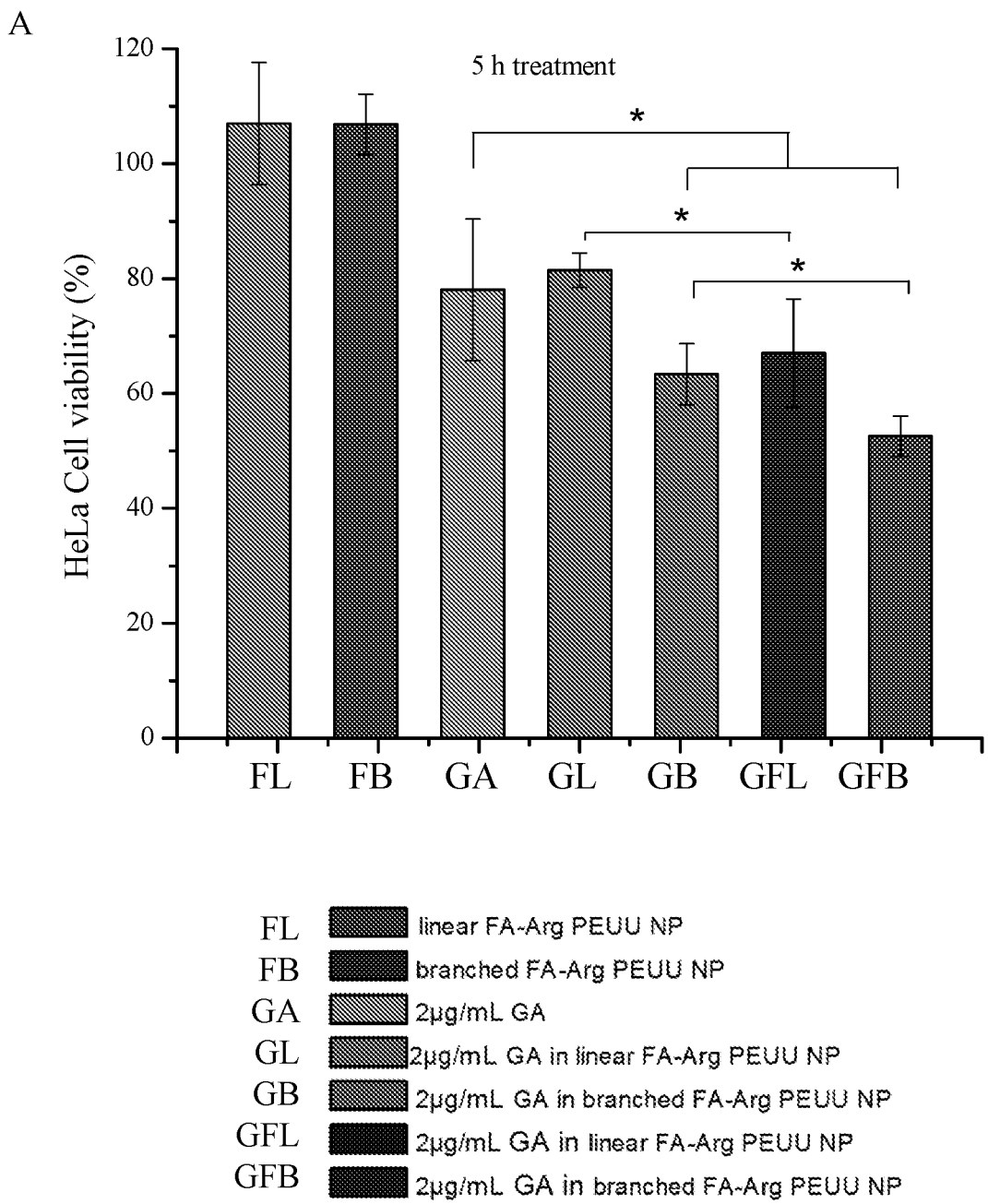
FIG. 6 shows cytotoxicity of blank and GA-loaded Arg-PEUU and FA-Arg-PEUU NPs toward HeLa cells at two GA concentrations (2 and 6 µg/mL) upon 5 h (A and C) and 12 h (B and D) incubations. (A) HeLa cell viability treated by blank Arg-PEUU and FA-Arg-PEUU NPs at 20 µg/mL NP carriers' concentration, 2 µg/mL free GA or equal amount GA-loaded in linear (GL), branched (GB), FA-tagged (GFL and GFB) Arg-PEUU NP carriers for 5 h. (B) same as A for 12 h; (C) 60 µg/mL blank Arg-PEUU NP carrier, 6 µg/mL GA or equal amount loaded in NP carriers for 5 h, and (D) same as C for 12 h. * $p<0.05$.
Figure 6:
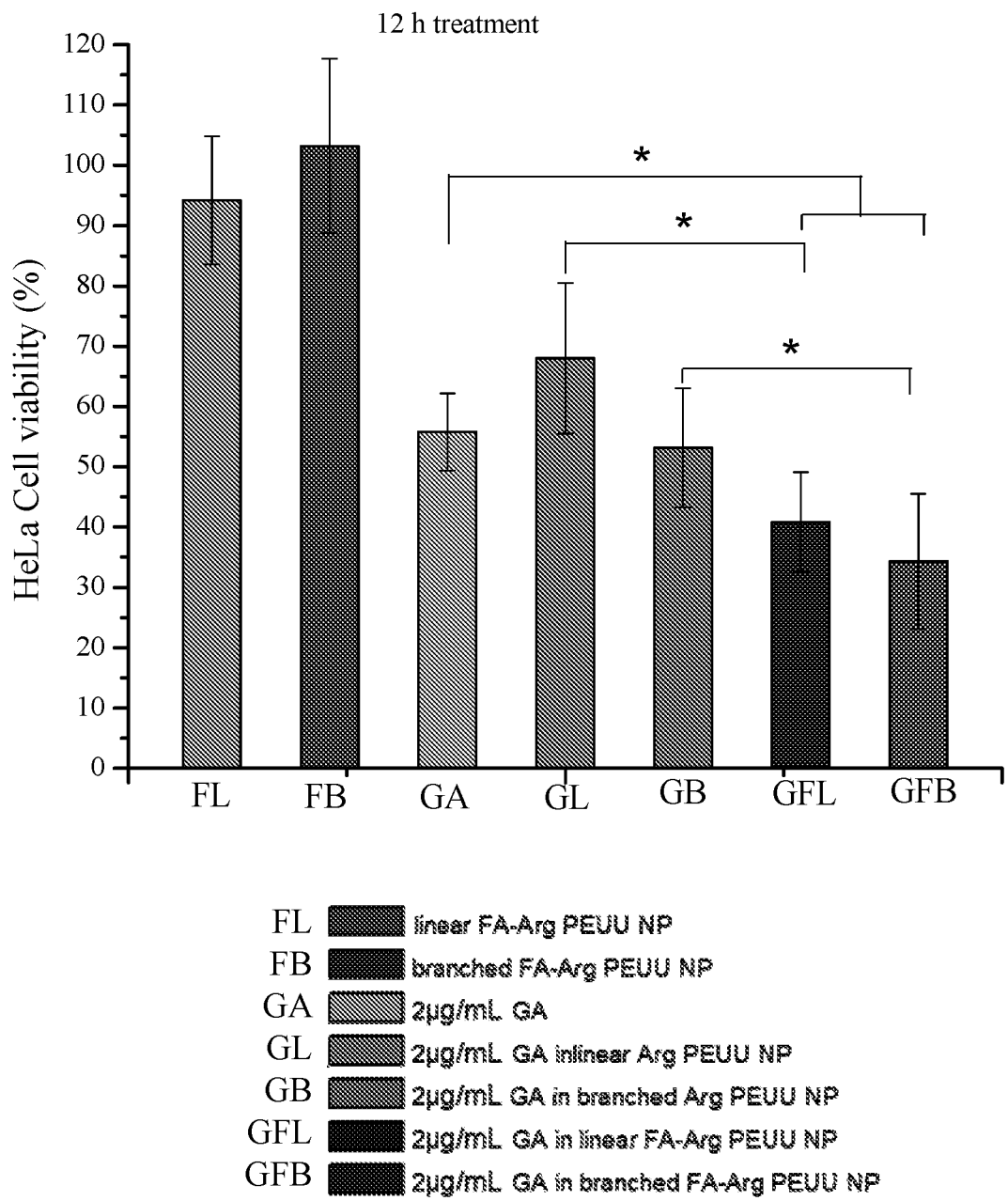
Figure 6:
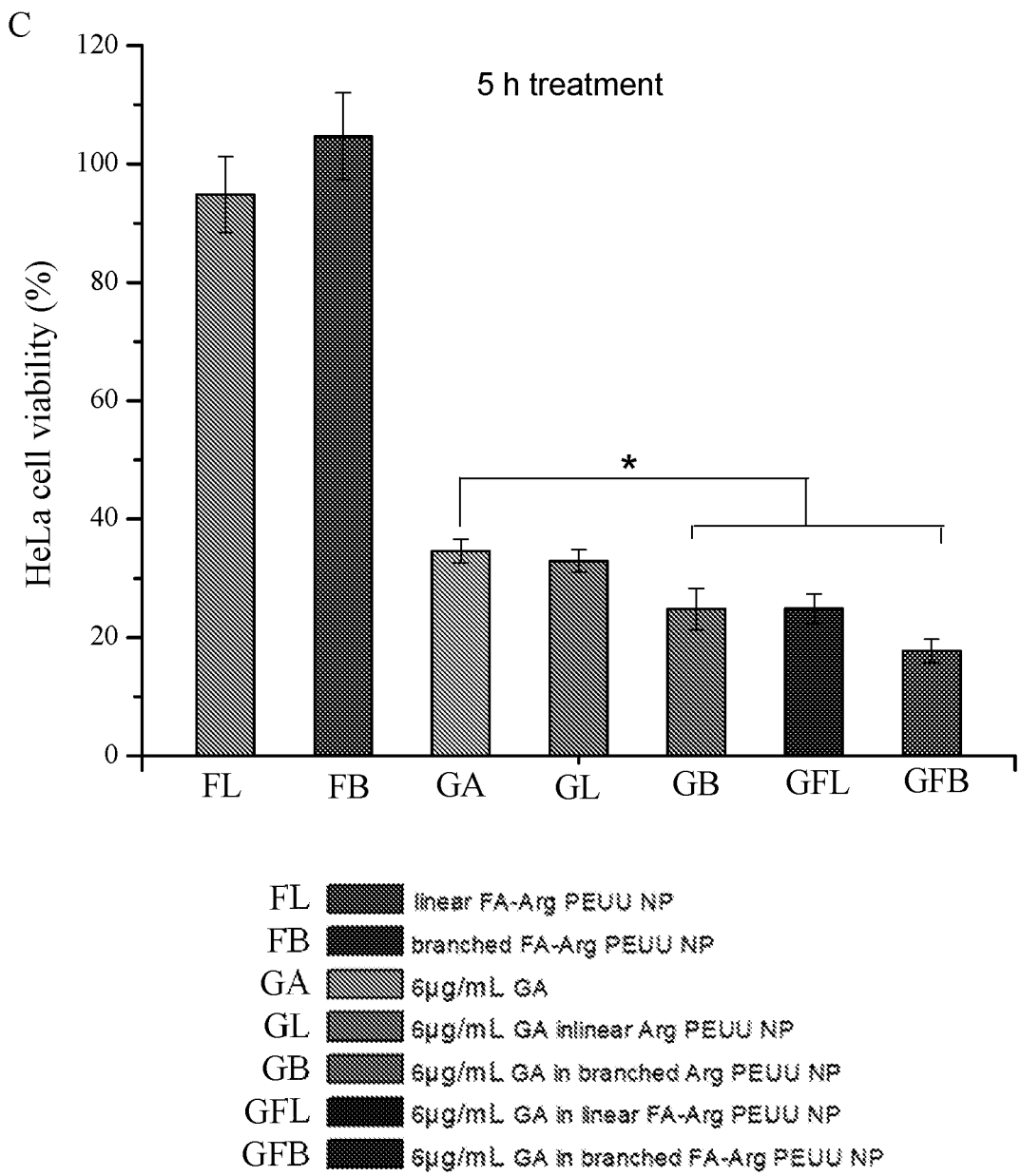
Figure 6:
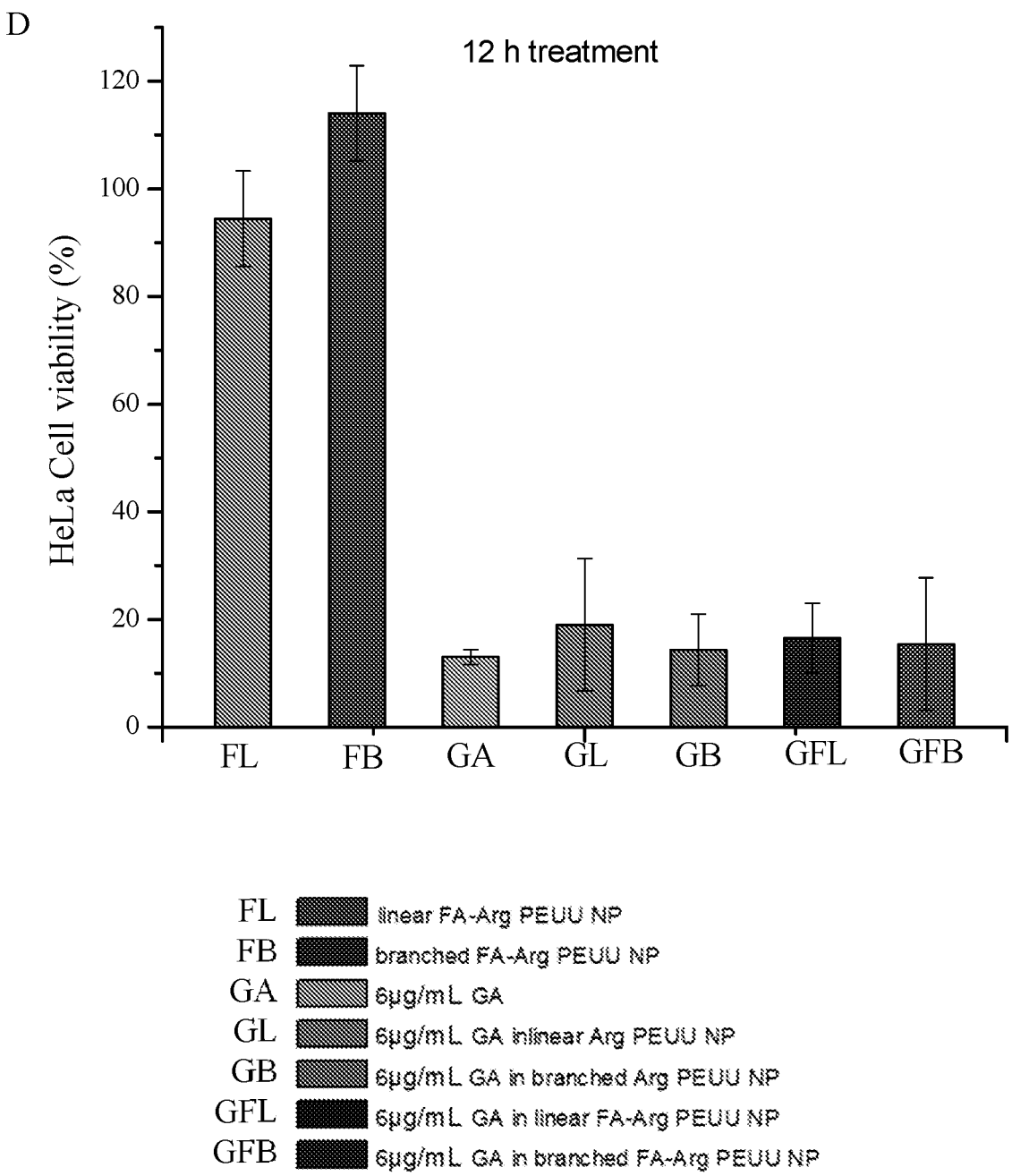
Figure 7:
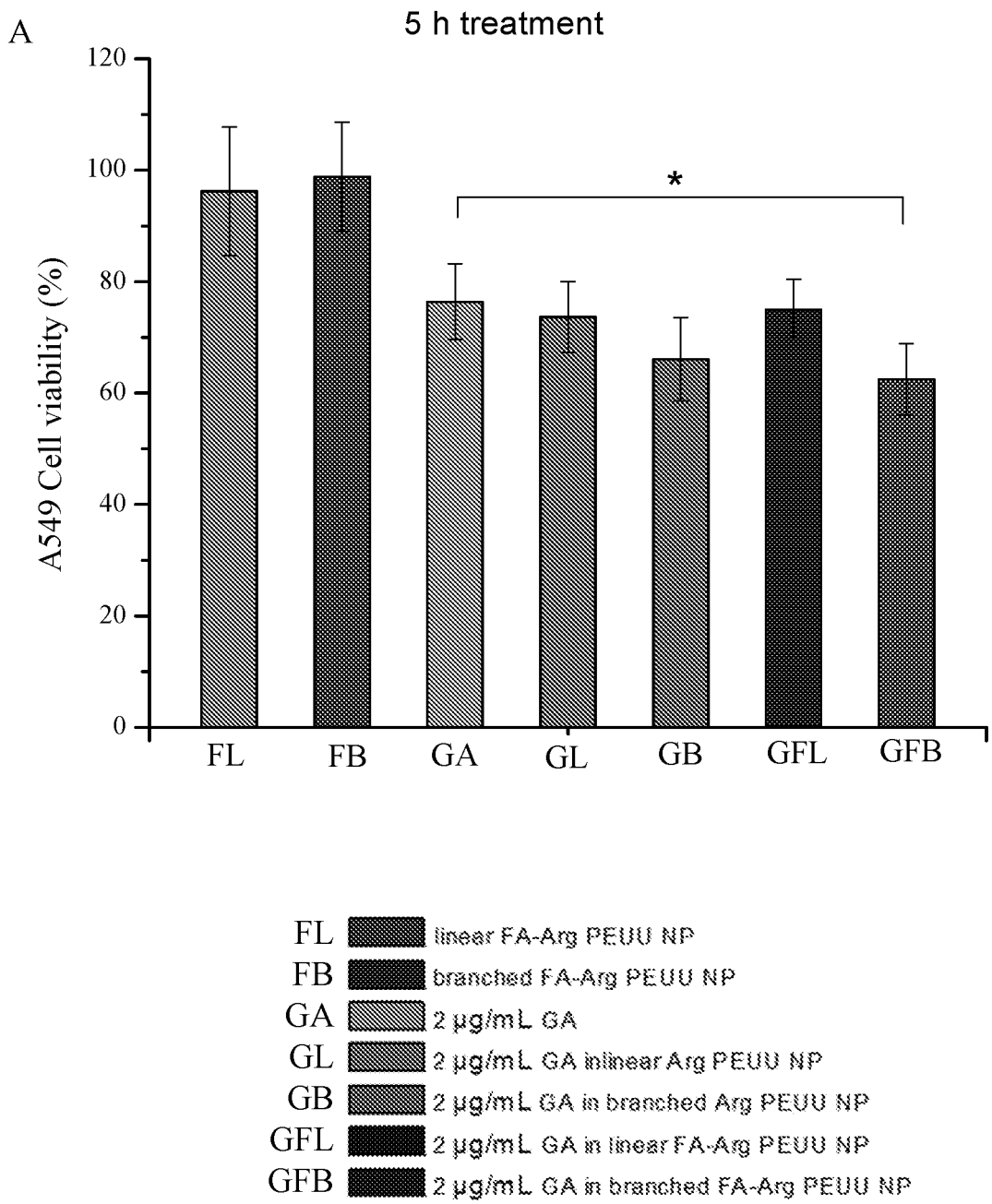
FIG. 7 shows cytotoxicity of blank and GA-loaded Arg-PEUU and FA-Arg-PEUU NPs toward A549 cells at two GA concentrations (2 and 6 µg/mL) upon 5 h (A and C) and 12 h (B and D) incubations. (A) A549 cell viability treated by blank Arg-PEUU and FA-Arg-PEUU NPs at 20 µg/mL NP carriers' concentration, 2 µg/mL free GA or equal amount GA-loaded in linear (GL), branched (GB), FA-tagged (GFL and GFB) Arg-PEUU NP carriers for 5 h, and (B) same as A for 12 h; (C) 60 µg/mL blank Arg-PEUU NP carrier, 6 µg/mL GA or equal amount loaded in NP carriers for 5 h, and (D) same as C for 12 h. * $p<0.05$
Figure 7:
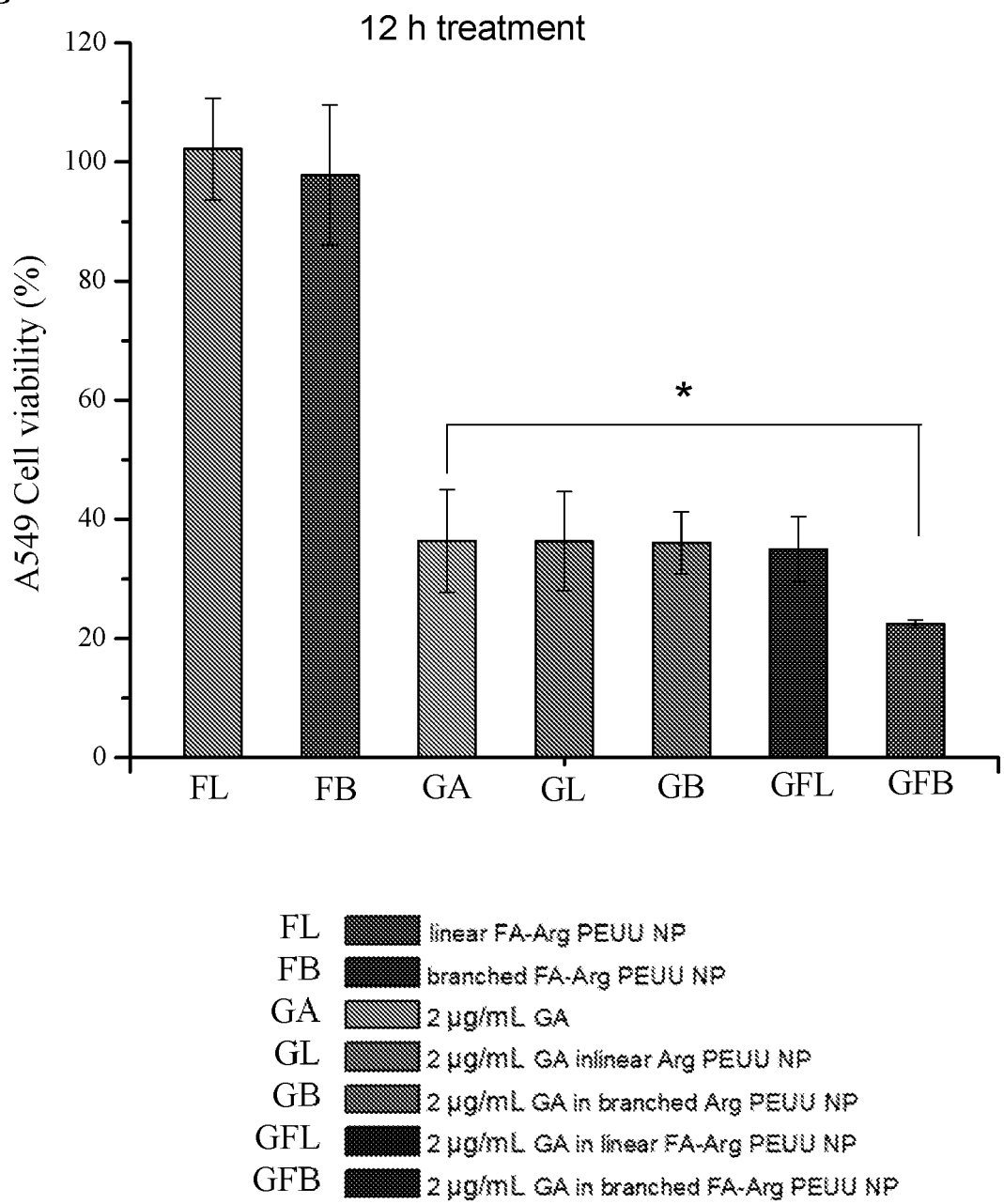
Figure 7:
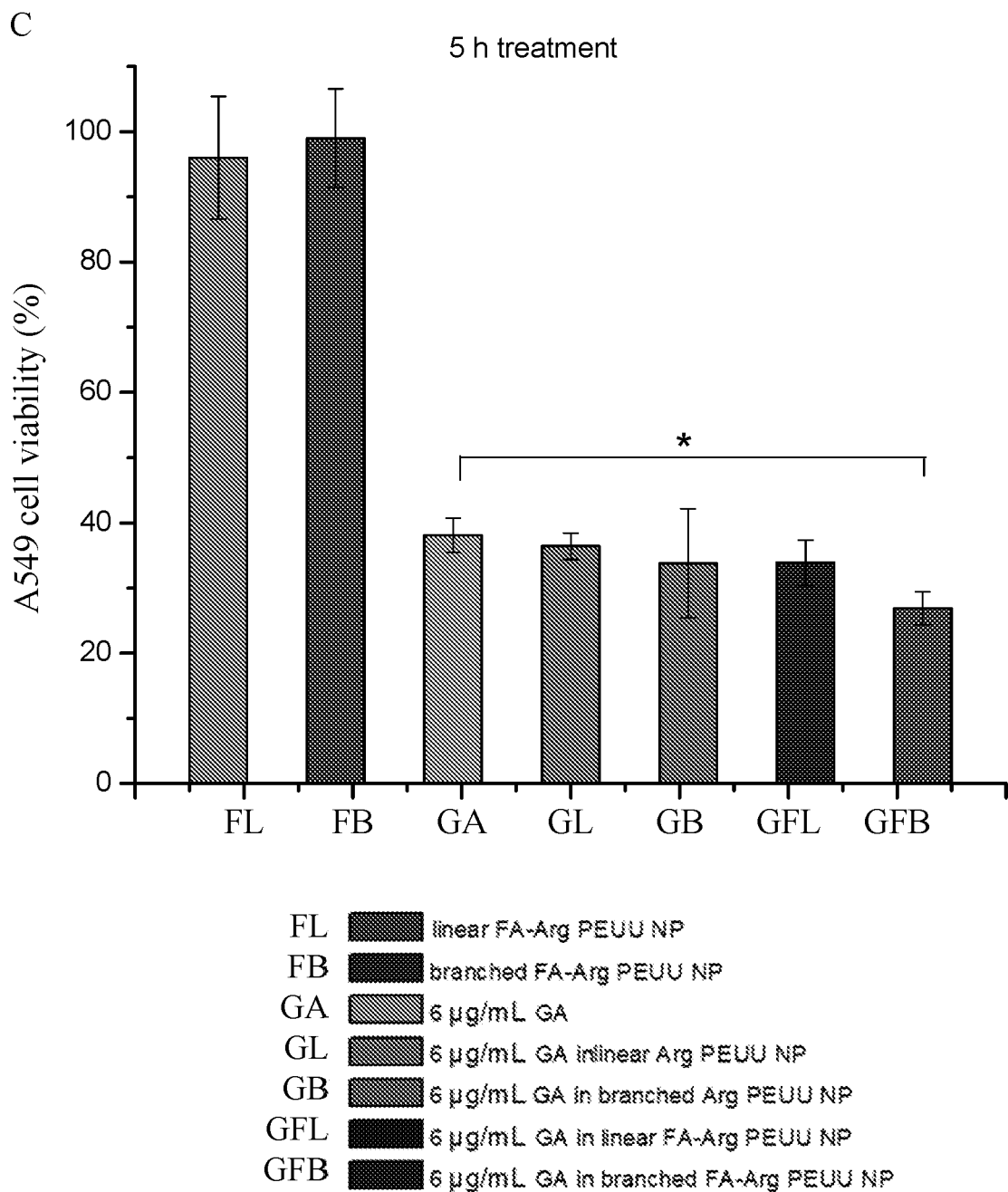
Figure 7:
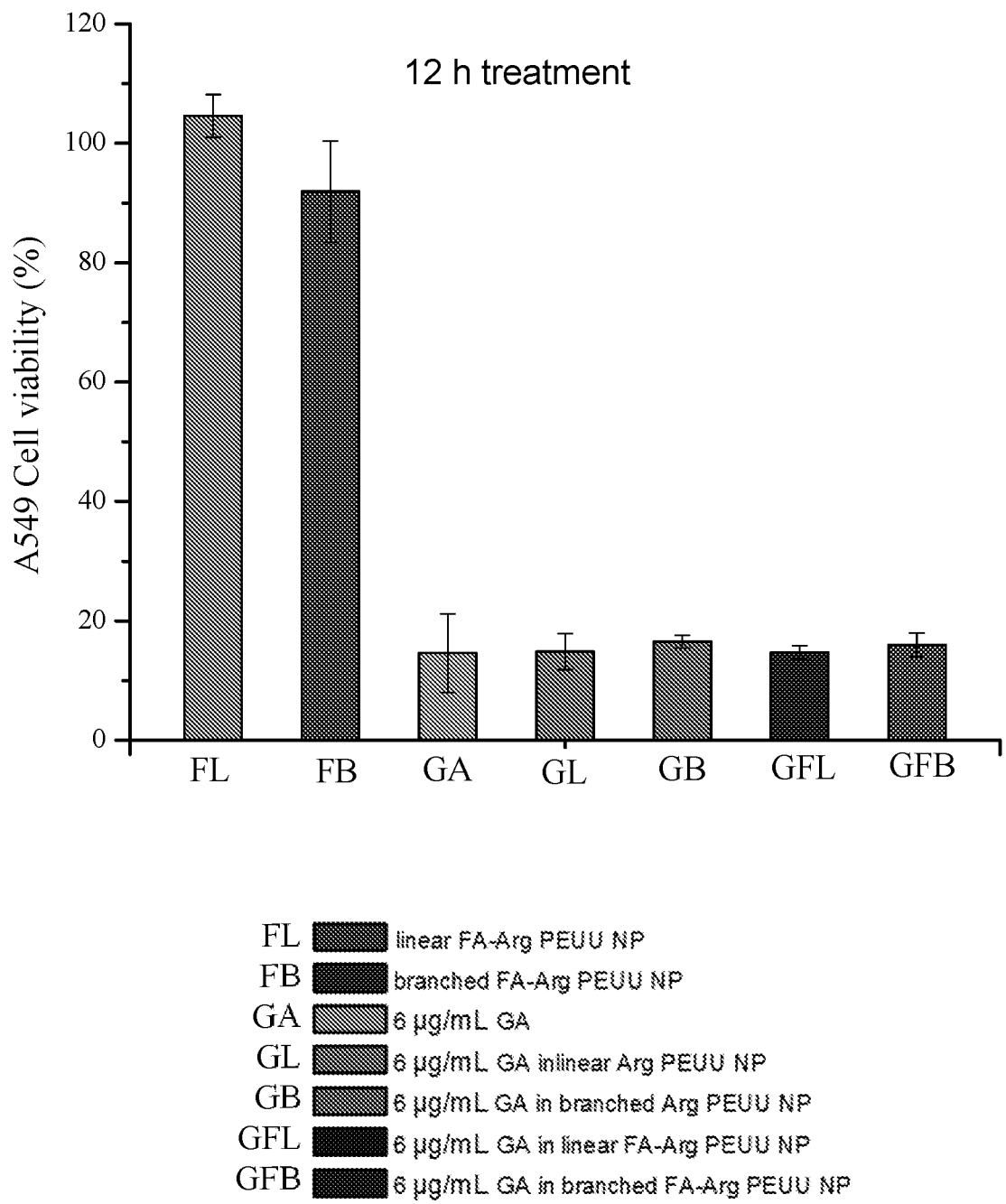

As shown in FIGS. 6 and 7, no cytotoxicity to HeLa and A549 cells was observed for both blank FA-Arg-PEUU NPs at 20 and 60 µg/mL NP concentrations and 5 and 12 h incubation periods with cell viability ranging from 94% to >100%. Similar good biocompatibility of Arg PEUU NPs without FA conjugated (up to 500 µg/mL in media) has been reported in prior studies. Free GA, GA-loaded Arg-PEUU and FA-Arg-PEUU NPs showed time and concentration-dependent cytotoxicity towards both cells. GFL or GFB showed 11.0% and 25.5% higher toxicity toward HeLa cells, respectively, than the free GA at 2 µg/mL 5 h incubation (FIG. 6A); a similarly trend was observed at 6 µg/mL GA concentration, 9.7% and 16.9% higher toxicity toward HeLa cells when comparing to the free GA data (FIG. 6B). In the case of A549 cells, the GL, GB, GFL and GFB treatments showed slightly higher toxicity than the free GA treatment at 2 µg/mL in media, i.e. 2.8%, 10.4%, 1.5% and 13.9% higher, upon 5 h incubation (FIG. 7A).

It's reported that GA can trigger apoptosis by contacting TfR on cell membrane. So, GA released from the Arg-PEUU NPs adhering onto the cell membrane can lead to a closer proximity to TfR and exerting cytotoxicity. Moreover, GA-induced cytotoxicity is only partially dependent on the Bcl-2 regulated apoptosis pathway. It is also a proteasome inhibitor and only gains proteasome-inhibitory function after being metabolized by intracellular CYP2E1. A few other studies reported that an improvement in internalization of GA by using submicron carriers (e.g., carbon nanotubes and hyaluronic acid derivative NPs) can increase its cytotoxicity.

Comparing to GL and GB, both GFL and GFB showed significantly lower HeLa cell viability at 2 µg/mL GA concentration in FIGS. 6A and 6B. At 6 µg/mL GA concentration, only small or little HeLa cell viability difference between samples was observed for 5 or 12 h incubation (FIG. 6C and FIG. 6D). GFB and GFL may promote GA cytotoxicity against HeLa by increased cell membrane adhesion and internalization (FIG. 5D and FIG. 6), when comparing to GB and GL. Since the FA conjugation approach didn't play an important role to improve adhesion and internalization towards A549 cells (FIG. 5E), the cell viability difference between GA-loaded carriers are not significant (FIG. 7).

GA induced cell apoptosis study performed by flow cytometry. Flow cytometry studies on HCT 116 and A549 cell lines were performed in order to quantify the percentages of apoptotic and necrotic cells after the treatment of GA-loaded Arg-PEUU NPs. HCT 116 is a FR-positive human colon cancer cell line which is more suitable for annexin-V-FITC/PI staining test than HeLa. FIG. 8A shows that GFB (54.6%) and GFL (54.7%) exhibited lower percentages of healthy HCT 116 cells than the 2 µg/mL free GA treatment (68.1%), similar percentage of dead cells, (31.0% for GFB and 25.1% for GFL vs. 27.7% for free GA), but with higher percentage of late apoptotic cells than the free GA treatment, i.e., 11.7% and 11.0% for GFB and GFL vs. 2.0% for free GA (FIG. 8A). Even for the FR-negative A549 cells treated by GB, GFB and GFL had a higher percentage of late apoptotic cells than the free GA treatment, but had lower dead cell percentage (FIG. 8B). GFL caused more late-apoptotic A549 cells (61.1%) than GB and GFB (20.3% and 35.3%); and this can possibly be attributed to the higher burst release of GA from the linear FA-Arg-PEUU NPs at the 24 h treatment period (FIG. 4).

Mitochondrial membrane potential disruption. The $\Delta\Psi m$ change of HeLa (FIG. 9A) and A549 (FIG. 9B) cells was detected after treated by the GA-loaded FA-Arg-PEUU NPs (equivalent to 2 µg/mL GA) for 24 h. When mitochondria lose the cross-membrane electrochemical gradient, JC-1 dissociates into monomers and emits green fluorescence. CCCP, as the positive control, strongly disrupted the mitochondrial membrane of HeLa cells (60.0% of the cell population) and A549 cells (89.7%), and showed high green fluorescence percentage and low red fluorescence percentage.

The percentages of HeLa cell populations that showed severe losses of $\Delta\Psi m$ after the GB, GFL and GFB treatments ranged from 35.1%, 37.5% and 39.6%, respectively, vs. 29.7% population after the free GA treatment (FIG. 9A). In the HeLa cells, GFB had a slight higher $\Delta\Psi m$ loss (39.6%) than the corresponding GB treatment (35.1%). The percentage of HeLa cells emitting red fluorescence also decreased accordingly. A549 cells treated by GB and GFB also showed higher percentage population with severe $\Delta\Psi m$ loss (70.0% and 64.0%) than GFL treatment (58.3%) and free GA (60.1%) as shown in FIG. 9B.

Figure 9:
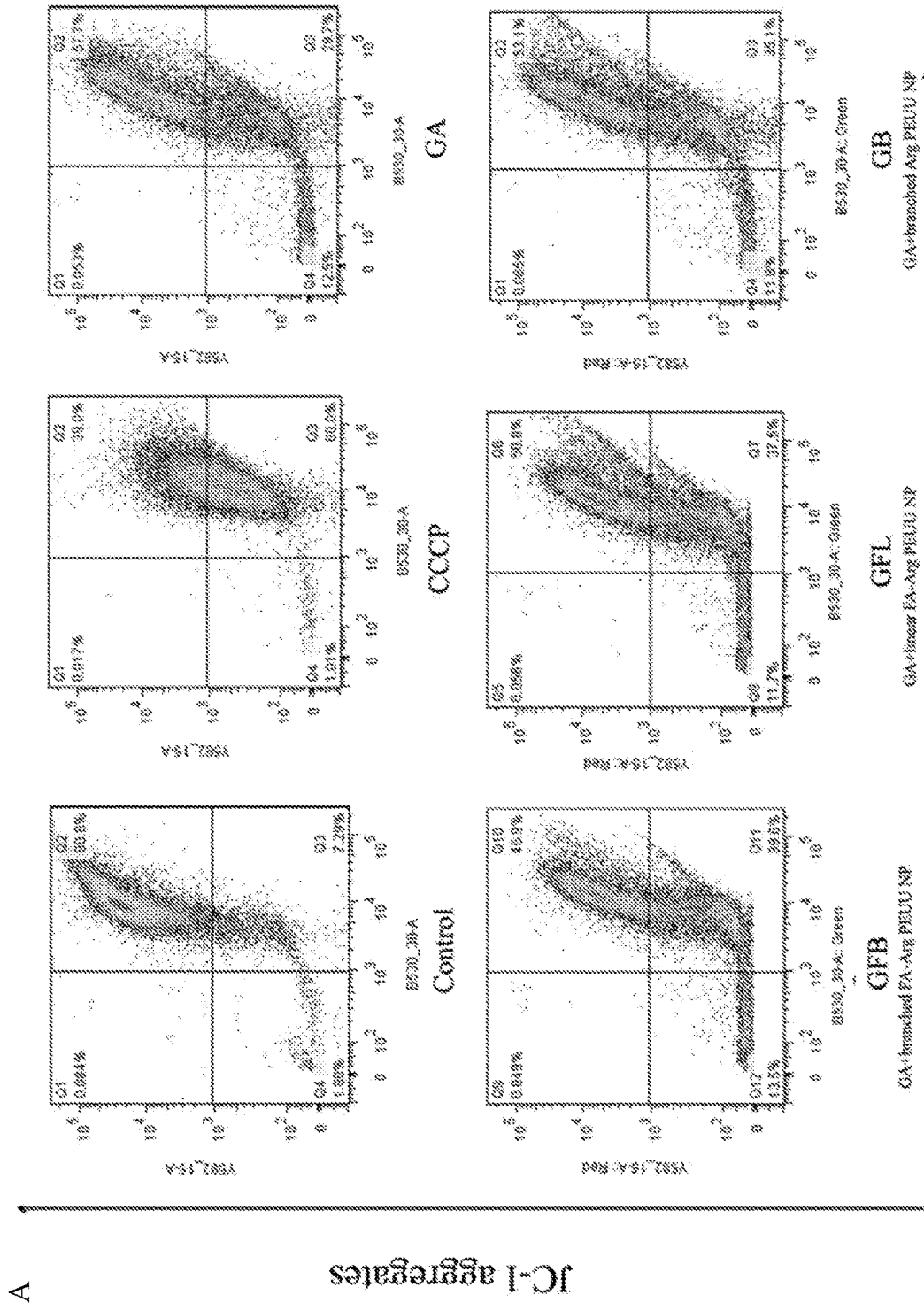
FIG. 9 shows flow cytometry analysis of mitochondrial membrane potential ($\Delta\Psi m$) change, in (A) HeLa and (B) A549 cells treated with 2 µg/mL free GA (GA), or equal amount GA-loaded in linear (GL), branched (GB) Arg-PEUU NP, FA-Arg-PEUU NP (GFL and GFB) carriers in media were incubated with $5\times10^5$ cells for 24 h. Cell culture media was used as control. Cells were stained with 2.5 µg/mL JC-1 dye. 50 µM CCCP in media was used to confirm JC-1 response.
Figure 9:
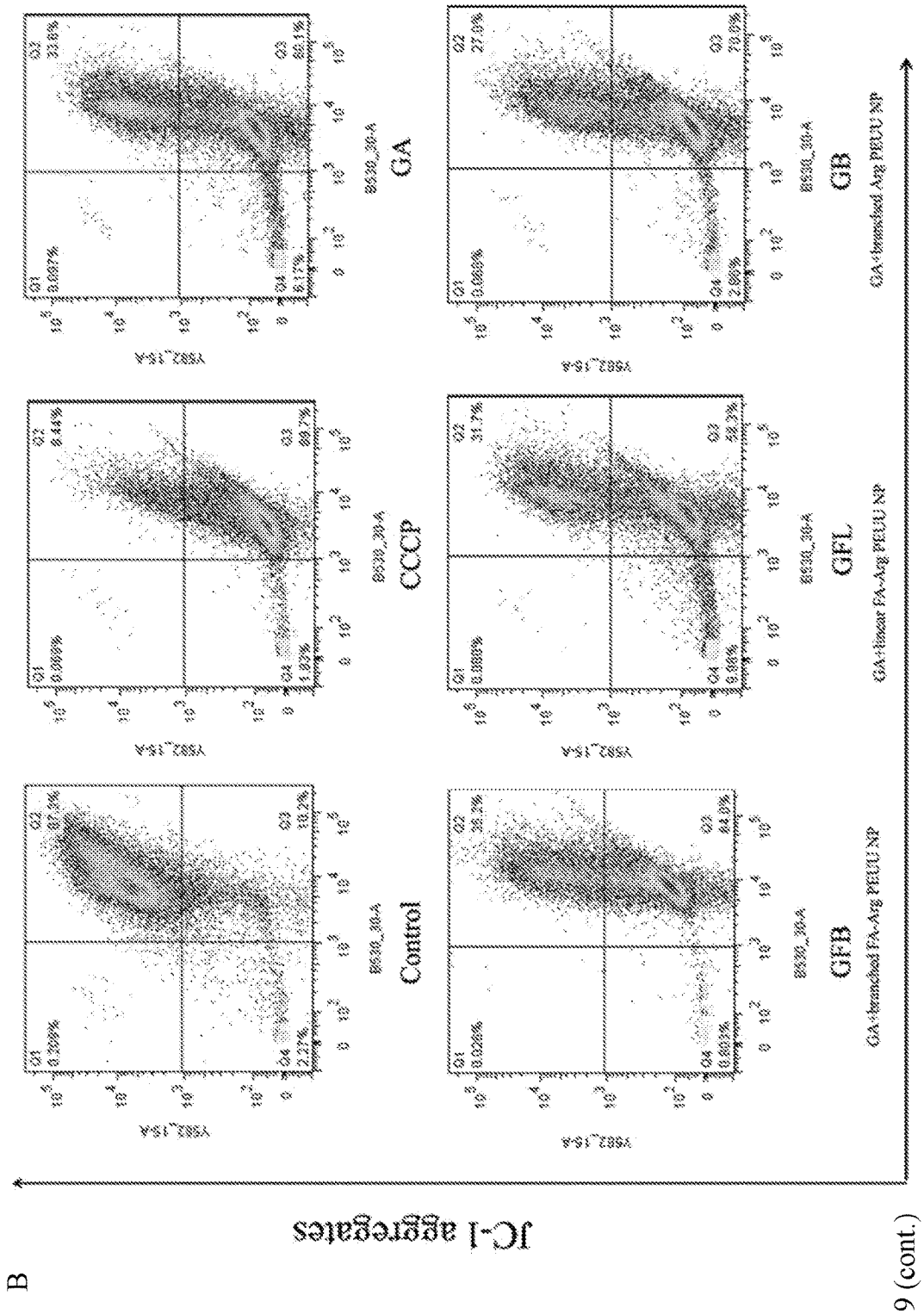

In the GA apoptotic mechanism, the imbalance in the mitochondrial membrane potential change causes membrane depolarization and induces a cascade of mitochondrion-dependent apoptotic signaling. It has been reported by Zhai et al. that GA neutralizes the biological function of Bcl-2 family which suppresses the release of apoptogenic protein from mitochondria; then leads to the disruption of mitochondrial membrane. The reduced $\Delta\Psi m$ is considered an irreversible step towards cell apoptosis, occurring in the first event during apoptosis. FIG. 9 indicates that using Arg-PEUU NP carriers to convey GA induced higher apoptotic cancer cell percentage, when compared to the free GA treatment at the same concentration and 24 h. The FA-Arg-PEUU NPs (GFL and GFB) also increased an additional 3~4% more apoptotic HeLa cells (FIG. 9A) than the GB treatment.

Figure 8:
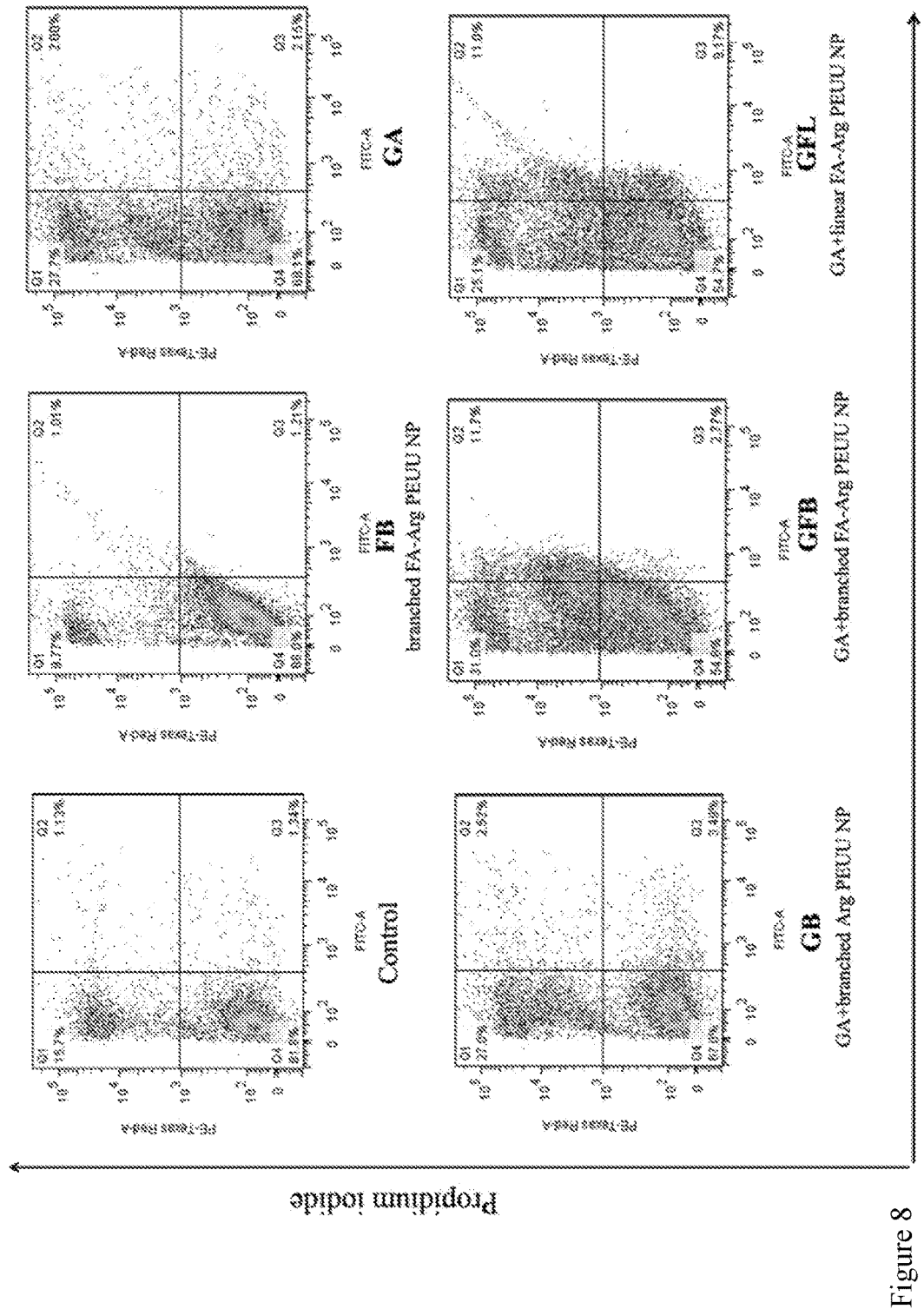
FIG. 8 shows flow cytometry analysis of annexin-V/PI stained HCT 116 (A) and A549 cells (B). 2 µg/mL free GA or equal amount GA-loaded in linear (GL), branched (GB), FA-Arg-PEUU NP (GFL and GFB) carriers in media were incubated with $5\times10^5$ cells for 24 h. Cell culture media was used as control.
Figure 8:
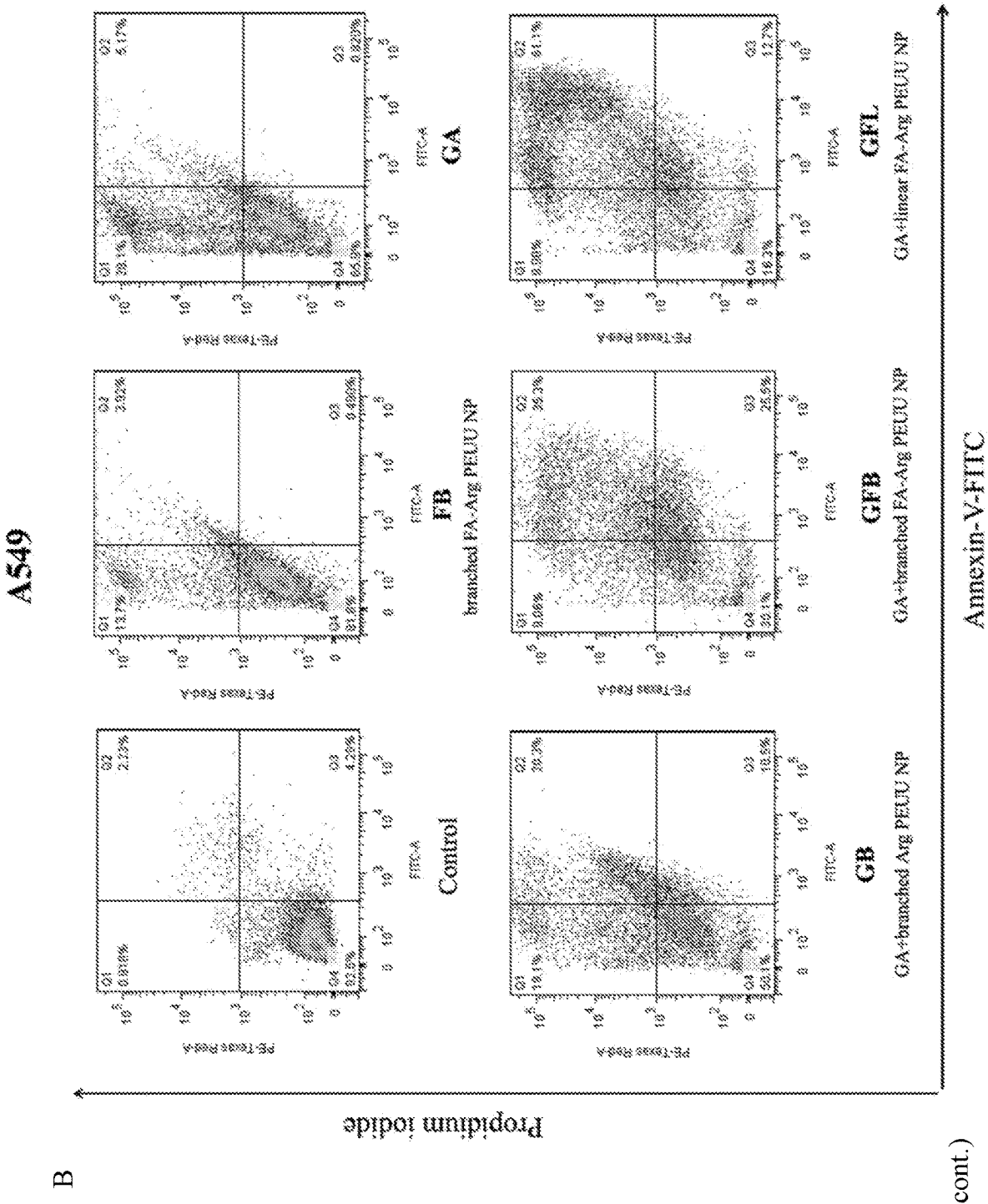
Figure 10:
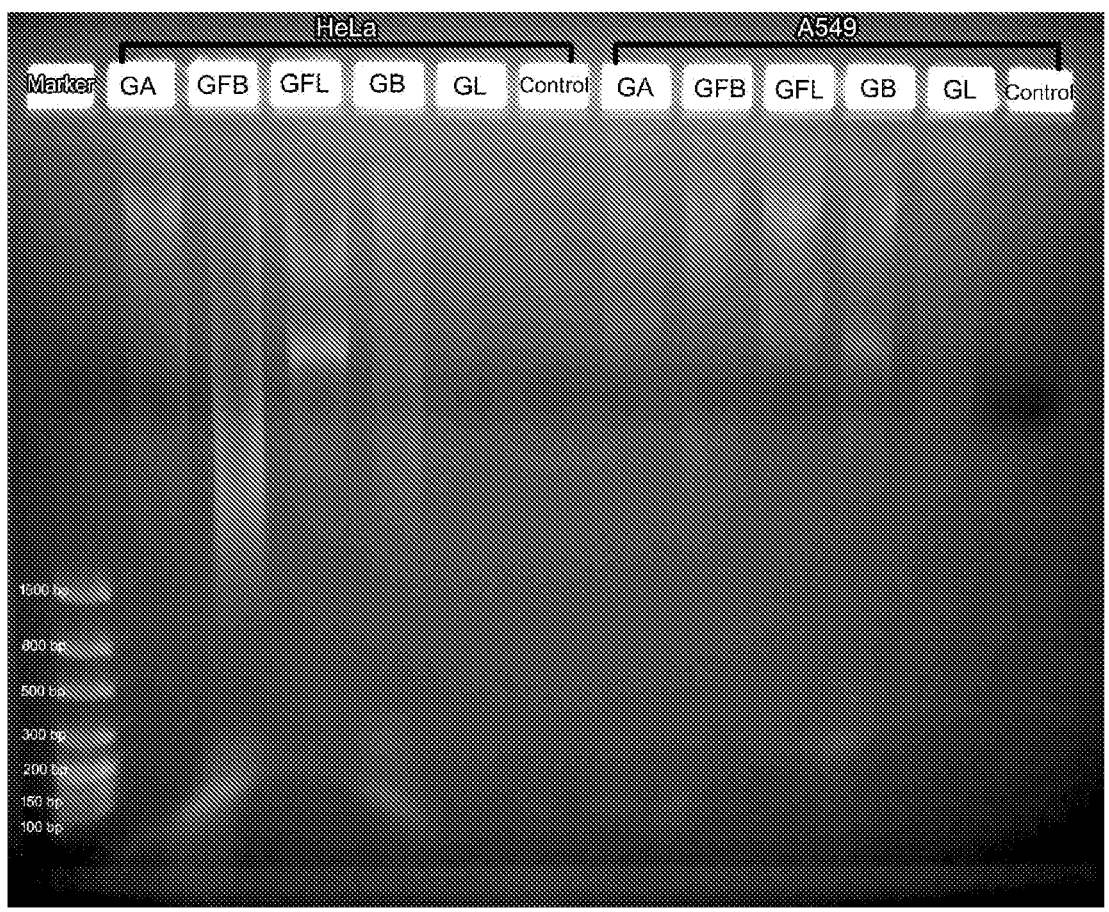
FIG. 10 shows DNA fragmentation in HeLa and A549 cells after treated with 2 µg/mL free GA or equal amount GA-loaded in linear (GL), branched (GB) Arg-PEUU NP, FA-Arg-PEUU NP (GFL and GFB) carriers for 48 h. Cell culture media was used as control. Marker: Flashgel™ DNA marker 50 bp-1.5 kb.

DNA fragmentation. DNA fragmentations induced by GA, GL, GB, GFB, and GFL NP carriers are shown in FIG. 10. GFL and GFB induced more fragmented DNA than the free GA treatment. In all testing samples, GFB induced the most complete DNA fragmentation in HeLa cells that produced 180-185 base pairs. Internucleosomal DNA fragmentation during apoptosis (so called DNA laddering) is activated when the inhibitor of the caspase-activated DNase (ICAD) is proteolyzed. DNA laddering is accompanied with the cleavage of crucial structural proteins by caspases which led to cell demolition. DNA degrading into nucleic acids is considered an indicator of apoptotic cell death. As shown in FIG. 8, GFL and GFB are more effective than free GA treatment to kill cancer cells by the apoptosis mechanism.

MMP activity. Gelatin zymography was used to examine MMP-2 and MMP-9 activity of HeLa and A549 cells after treated with 0.6 μg/mL free GA and equivalent amounts of GA-loaded Arg-PEUU NP carriers. The MMP-2 and MMP-9 activity data provides clues about the potential of the GA treatment from the loaded Arg-PEUU NP carriers toward the metastasis and invasion character of the treated cancer cells. The low GA concentration (0.6 μg/mL) was chosen to circumvent the cell viability influence to the MMP production. It was previously reported that up to 0.75 μg/mL GA treated MDA-MB-231 human breast carcinoma cells still had a higher than 90% cell viability after 24 treatment.

Figure 11:
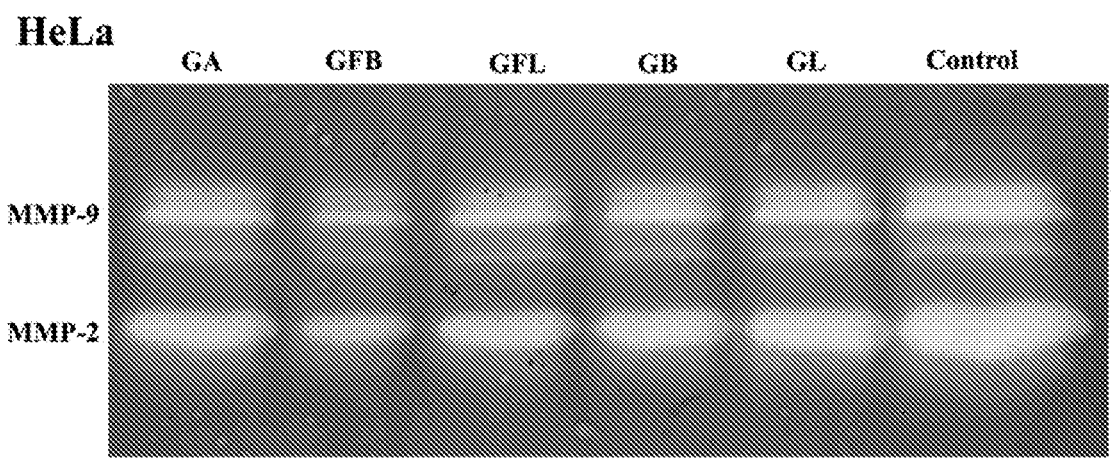
FIG. 11 shows gelatin zymography analysis of HeLa (A) and A549 (B) cells treated by 0.6 µg/mL free GA or equal amount GA-loaded in linear (GL), branched (GB) Arg-PEUU NP, FA-Arg-PEUU NP (GFL and GFB) carriers in serum-free media were incubated with $9\times10^5$ cells for 16 h. Serum-free cell culture media was used as control.
Figure 11:
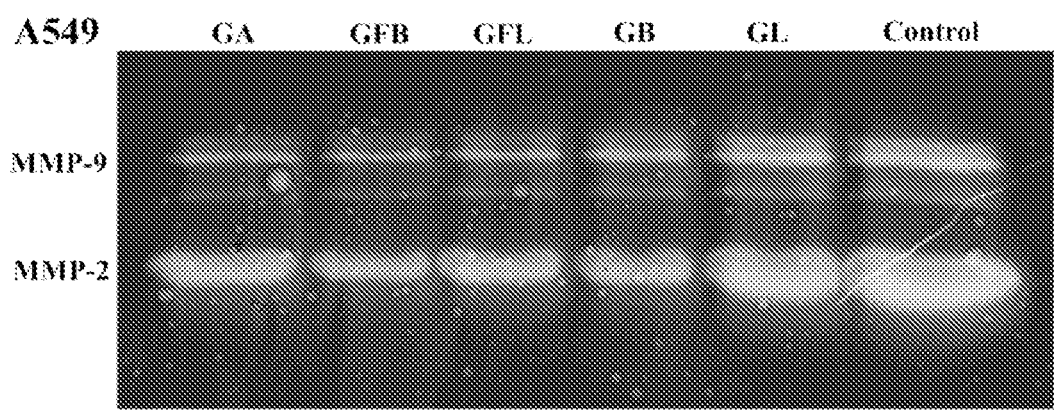

As shown in FIG. 11, zymography of an equal volume of medium conditioned by $9\times10^5$ cells after treated with free GA and various GA in carriers revealed smaller band area than that of control group. For HeLa, the GFB treatment showed the lowest band intensity and smallest size, followed by GFL, GB, GL GA treatments in FIG. 11A. For A549, the MMP activity from the free GA treated cells (FIG. 11B) was also reduced when comparing to the control sample. Among the Arg-PEUU NP samples, the GFB treatment showed the smallest MMP band size and intensity, while the MMP activities among GFL, GB, GL were similar to the free GA treatment.

MMPs are a family of zinc-dependent endopeptidases that are involved in tumor invasion and metastasis. The inhibition of MMP activity is important for controlling tumor growth and metastasis. GA induces down-regulation of MMP-9 by down-regulating NF-κB, and the TfRs are required for this regulation pathway. The adherence onto cancer cells might facilitate the loaded GA to interact with TfRs on cancer cell membranes. In addition, FA conjugation onto Arg-PEUU NPs can also improve the Arg-PEUU NP binding to FR-positive HeLa, so the inhibition effect of the GA loaded in the Arg-PEUU NPs on MMP production is more prominent than the FR-negative A549. From in vitro data, the GA delivered by FA-Arg-PEUU NP carriers may reduce the tumor cell invasion and metastasis by reducing the MMP activity even at a low GA concentration, i.e. 0.6 μg/mL.

Gambogic acid (GA) is known for its broad spectrum of anticancer activity and low toxicity to normal tissues, but its pharmaceutical and clinical application has been limited by its poor water solubility, sensitivity to hydrolysis, light, etc. To overcome these drawbacks, linear and branched Arg-based poly (ester urea urethane)s (Arg-PEUU) and folate (FA) conjugated Arg-PEUU were synthesized, and characterized. Typical linear and branched Arg-PEUU polymers have number average molecular weights ($M_n$) 18,430 and 25,530 g/mol, respectively. To be applied as GA carriers, Arg-PEUU or FA-Arg-PEUU nanoparticles (NPs) were formulated with average size ranged from 98 to 267 nm in diameter with zeta potential from +5.4 to +12.2 mV. Arg-PEUU or FA-Arg-PEUU NPs achieved good adhesion and internalization into cancer cells in 4 h.

The GA-loaded NPs were examined for their anticancer cell effects on folate receptor (FR) overexpressed cells (HeLa, HCT 116). FR-negative cell (A549) was used for comparison and confirmed the role of FA conjugation in NP adhesion/internalization. In general, FA-Arg-PEUU NP carriers showed more GA potency toward HeLa/HCT 116 than the NP carriers without FA decoration. The GA at 2 μg/mL delivered by the NP carriers led to a higher cytotoxicity and induced a higher apoptosis percentage against cancer cells than the free GA. Higher mitochondrial membrane potential disruption, increased DNA fragmentation and reduced matrix metalloproteinases (MMP-2 and MMP-9) activity were also observed from the cancer cells treated with GA-loaded PEUU NP carriers. FA conjugation on Arg-PEUU NPs improved the cell attachment/internalization and enhanced GA potency against cancer cells.

EXAMPLE 2

This example provides a description of polymers and nanoparticles of the present disclosure, and methods of making and using polymers and nanoparticles of the present disclosure.

Self-Assembled Cationic Biodegradable Nanoparticles from pH-Responsive Amino-Acid-Based Poly(Ester Urea Urethane)s and Their Application As a Drug Delivery Vehicles. In this example, a new family of biodegradable and biologically active copolymers and their subsequent self-assembled cationic nanoparticles were developed as better delivery vehicles for anticancer drugs to achieve the synergism between the cytotoxicity effects of the loaded drugs and the macrophage inflammatory response of the delivery vehicle. This family of cationic nanoparticles was formulated from a new family of amphiphilic cationic Arginine-Leucine (Arg-Leu)-based poly(ester urea urethane) (Arg-Leu PEUU) synthesized from four building blocks (amino acids, diols, glycerol α-monoallyl ether, and 1,6 hexamethylene diisocyanate). The chemical, physical, and biological properties of Arg-Leu PEUU biomaterials can be tuned by controlling the feed ratio of the four building blocks. The Arg-Leu PEUU copolymers have weight-average molecular weights from 13.4 to 16.8 kDa and glass-transition temperatures from −3.4 to −4.6° C. The self-assembled cationic nanoparticles (Arg-Leu PEUU NPs) were prepared using a facile dialysis method. Arg-Leu PEUU NPs have average diameters ranging from 187 to 272 nm, show good biocompatibility with 3T3 fibroblasts, and they support bovine aortic endothelial cell (BAEC) proliferation and adhesion. Arg-Leu PEUU NPs also enhanced the macrophages' production of tumor necrosis factor-α (TNF-α) and nitric oxide (NO), but produced relatively low levels of interleukin-10 (IL-10), and therefore, the antitumor activity of macrophages might be enhanced. Arg-Leu PEUU NPs were taken up by HeLa cells after 4 h of incubation. The in vitro hemolysis assay showed the cationic Arg-Leu PEUU NPs increased their chance of endosomal escape at a more acidic pH. Doxorubicin (DOX) was successfully incorporated into the Arg-Leu PEUU NPs, and the DOX-loaded Arg-Leu PEUU NPs exhibited a pH-dependent drug release profile with accelerated release kinetics in a mild acidic condition. The DOX-loaded 6-Arg-4-Leu-4 A/L-2/1 NPs showed higher HeLa cell toxicity than the free DOX at the same concentration after 24 h of treatment. The results suggest the cationic Arg-Leu PEUU NPs could potentially be a useful carrier family for hydrophobic anticancer drugs and produce a synergistic effect between DOX cytotoxicity and the production of TNF-α and NO by macrophages.

In this example, a new Arg-Leu PEUU polymer family is designed, synthesized and characterized to explore its feasibility and potential as an advanced cationic nanocarrier biomaterial for hydrophobic anticancer drugs such as DOX. Arg possesses a strong cationic nature allowing for better cell uptake, giving it an important role in macrophage-induced TNF-α and NO production. Leu, a neutral and hydrophobic amino acid, is complementary to hydrophilic Arg because it provides a hydrophobic moiety required for the self-assembly and stability of the resulting self-assembled NPs. It has been reported that the Leu moiety in the protein, the peptide, and synthetic polymers help the formation and stabilize the supra-molecular structure. These novel Arg-Leu PEUU NPs may be utilized as nano drug carriers to improve cancer therapies.

Experimental Section

Materials. L-Arginine hydrochloride (L-Arg-Cl) (Alfa Aesar, Ward Hill, Mass.), L-Leucine (TCI, Portland, Oreg.), 1,4-butanediol (Alfa Aesar, Ward Hill, Mass.), p-toluene sulfonic acid monohydrate (TsOH·H$_2$O) (JT Baker, Philipsburg, N.J.), sodium bicarbonate, glycerol α-monoallyl ether (GAE, TCI, Portland, Oreg.), hexamethylene diisocyanate (HDI) (Acros organics, Geel, Belgium), and triethylamine (TEA) (99%, EMD Chemical, Darmstadt, Germany), were used without further purification. Stannous 2-ethyl-hexanoate and fluorescein isothiocyanate (FITC) were purchased from Sigma (St. Louis, Mo.). Cysteamine was purchased from TCI in Portland, Oreg. Doxorubicin hydrochloride (DOX·HCl) was purchased from Lancrix Chemicals in Shanghai, China. Thiazolyl blue tetrazolium bromide, branched polyethylenimine (PEI, Mn 1800 g/mol) and 4% paraformaldehyde in PBS were purchased from Alfa Aesar in Ward Hill, Mass. Solvents such as toluene, chloroform (VWR Science, West Chester, Pa.), dimethyl sulfoxide (DMSO), N,N-dimethylformamide (DMF) (Mallinckrodt incorporated, St. Louis, Mo.), anhydrous ethyl alcohol (PHARMCO-AAPER, CT), isopropyl alcohol (ACS, 99.5%, Macron Chemicals, Philipsburg, N.J.), and ethyl acetate (BDH, London, U.K.) were used without further purification. Dialysis bags (molecular weight cutoff (MWCO): 3500 g/mol and 10 000 g/mol) were purchased from Thermo Fisher Scientific in Rockford, Ill. Prolong Gold antifading mounting reagent with DAPI (4',6-diamidino-2-phenylindole) was purchased from Life Technologies in CA and bovine whole blood was purchased from Lampire biological laboratory in Pipersville, Pa. The TNF-α assay kit was purchased from Biolegend in San Diego, Calif. and the Griessreagent system was purchased from Promega in Madison, Wis. The vinculin primary antibody and DAPI were purchased from Sigma (St. Louis, Mo.). Alexa Flour 488 and Phalloidin Alexa 568 were purchased from Life Technologies (Waltham, Mass.).

Synthesis of Dihydrochloride Acid Salt of Bis (L-Arg) Butane Diester Monomers (Arg-4-Cl) and Bis (L-Leu) Butane Monomers (Leu-4). The Arg-4-Cl and Leu-4 building blocks were synthesized according to a previously described method with minor modifications. Briefly, L-Arg hydrochloride or L-Leu (0.04 mol) and 1,4 butanediol (0.018 mol) were directly condensed in 80 mL of refluxed toluene (bp 110° C.) with the presence of TsOH·H$_2$O (0.05 mol). The heterogeneous solid-liquid reaction mixture was heated to 120° C. and refluxed for 48 h after ~1.62 mL (~0.09 mol) of water was generated and collected by a dean-stark apparatus. After the reaction was ended and cooled to room temperature, toluene was decanted. Arg-4-Cl was purified by recrystallization three times in cold isopropyl alcohol (precipitate at −20° C.) and then was dissolved in 50 mL of deionized (DI) water. The TsO$^-$ ion on the amino group of Arg was then neutralized by adding 2 M sodium bicarbonate into the solution to reach a final pH of 9.5. The resulting bis (L-Arg) butane diester aqueous solution was then vacuum-dried at room temperature. Leu-4 was purified by recrystallization in DI water three times (precipitated at 4° C.), and the TsO$^-$ ion was neutralized by adjusting the pH of its aqueous solution to 9.5 with 1 M sodium bicarbonate. The Leu-4 solution was then quickly cooled in an ice-water bath and refrigerated for 8 h at 4° C. The Leu-4 precipitation from the cooled aqueous solution was filtered and vacuum-dried.

Figure 12:
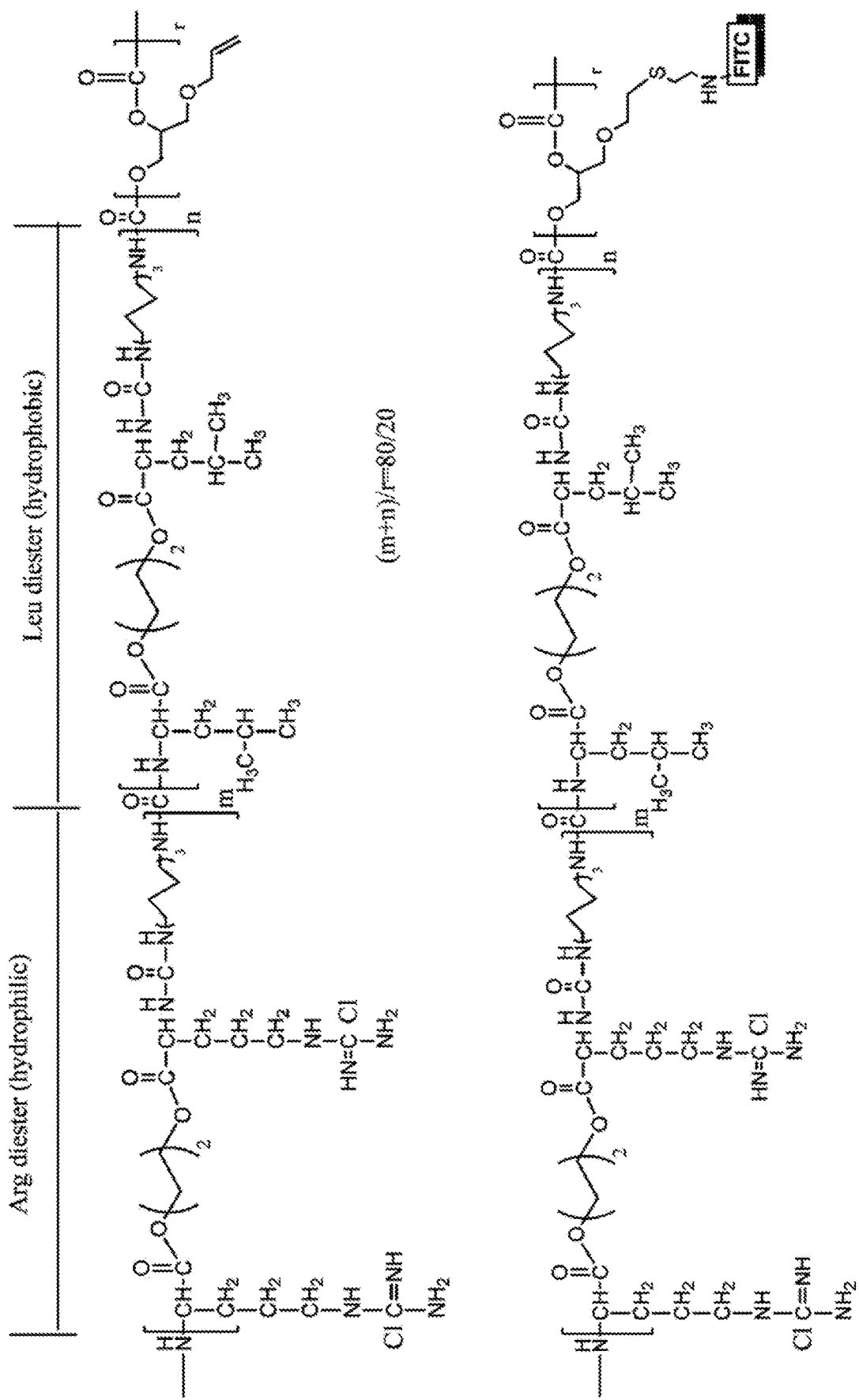
FIG. 12 shows chemical structures of Arg-Leu PEUUs and their FITC-labeled derivatives.

Synthesis of the Arg-Leu PEUU Series. The Arg-Leu PEUUs were synthesized using a two-step solution polymerization that is similar to the Arg-based PEUU preparation method. The generic chemical structure of the Arg-Leu PEUU is shown in FIG. 12. GAE diol was reacted with an excess amount of HDI to form a prepolymer in the first step. The incorporation of GAE into the PEUU polymer backbone introduced reactive pendant double bonds which can be further converted into other pendant functional groups (amine, carboxyl, hydroxyl) by the thiol-ene reaction. In this example, the pendant double bonds were then converted into free amine groups and labeled with FITC dye to image endocytosis of the Arg-Leu PEUU NPs. In the synthesis of Arg-Leu PEUU, the stiochiometry of GAE to the sum of Arg-4-Cl and Leu-4 was set to 1/4. In the second step, Arg-4-Cl and Leu-4 in DMSO solution were added in the reaction to extend the prepolymer synthesized in step one. Polymerization was carried out in a 250 mL three-necked round bottomed flask under a dry nitrogen atmosphere. The stoichiometry of Arg-4-Cl and Leu-4 monomers were 2/1, 1/1, 1/2, and 1/4. The sum of the molar amounts of GAE, Arg-4-Cl, and Leu-4 were equal to the molar amounts of HDI. For example, in a typical synthesis of 6-Arg-4-Leu-4 PEUU A/L-1/1 (where A/L is the molar ratio of Arg-4-Cl (m) to Leu-4 (n) building blocks in the Arg-Leu PEUU), 0.05 mol HDI (8.41 g) and 0.01 mol GAE (1.32 g) were magnetically stirred in 30 mL of DMSO with stannous 2-ethyl-hexanoate catalyst (1 wt % of total mass of reactants). The mixture was allowed to react at 50° C. for a period of 3 h under a dry nitrogen atmosphere with gentle magnetic stirring. 80 mL of DMSO solution of 0.02 mol Arg-4-Cl monomer and 0.02 mol Leu-4 were then added to the prepolymer solution, and the reaction continued at 50° C. for 20 h under a dry nitrogen atmosphere. The polymer product was precipitated out from the solution by adding cold ethyl acetate. The precipitant was collected and vacuum-dried at room temperature. The crude polymer product was purified by dialysis (1 L, 6 h; MWCO: 3500 g/mol) twice against ethanol first and then purified further by dialysis (3 L, 6 h; MWCO: 3500 g/mol) three times against DI water at room temperature. The milky and cloudy product suspension and precipitation in the dialysis bag was collected and finally dried in vacuo.

Arg-Leu PEUU Labeled with FITC. Cysteamine was used to convert the pendant double bonds of Arg-Leu PEUU into amine groups for subsequent FITC labeling. 300 mg of cysteamine was added into 25 mL of 20 wt % Arg-Leu PEUU DMSO solution in a glass flask equipped with a magnetic stirring bar. The flask was heated in an oil bath of 70° C. overnight. The resulting product (Arg-Leu PEUU-NH2) was precipitated out by adding cold ethyl acetate, and filtered and purified by dialysis against DI water (3 L, 6 h; MWCO: 3500 g/mol) four times. After drying in vacuo, 1 g of Arg-Leu PEUU-NH2 and 10 mg of FITC were dissolved into 5 mL of DMSO, and then protected from light and stirred at room temperature for 10 h. The solution was then dialyzed in the dark against DI water (2 L, 6 h; MWCO: 3500 g/mol) to remove the physically absorbed FITC. Arg-Leu PEUU-FITC was collected by vacuum drying the suspension in a dialysis bag at room temperature and stored in a dark and dry environment before use.

Characterizations of Arg-Leu PEUU. The Arg-4-Cl, Leu-4 monomers and Arg-Leu PEUUs were analyzed by proton nuclear magnetic resonance ($^1$H NMR). $^1$H NMR spectra were recorded on a Varian (Palo Alto, Calif.) INOVA-400 spectrometer at 400 MHz. Deuterated dimethyl sulfoxide (DMSO-$d_6$, Cambridge Isotope Laboratories) was used as the solvent. The sample concentration in DMSO-$d_6$ was about 1% (w/v). All of the chemical shifts were reported in parts per million (ppm). Fourier transform infrared (FTIR) spectra of Arg-Leu PEUUs were recorded on a PerkinElmer (Madison, Wis.) Nicolet Magna 560 FTIR spectrometer with Omnic software for data acquisition and analysis. All solubility tests were performed in glass vials at room temperature. Gel permeation chromatography (GPC) of Arg-Leu PEUU was tested at the University of California, Santa Barbara on a Waters Agilent GPC equipped with Waters Alliance HPLC 2695 separation pump, Visco Gel I-series columns (IMBHMW-3078, Viscotek, 7.8 mm×30 cm), a Waters 2414 differential RI detector, and a Waters 2998 Photodiode Array Detector (PDA). DMF (containing 0.1% lithium bromide) was used as an eluent (at a flow rate of 1 mL/min) at 25° C. The injection volume of the polymer sample solution was 100 μL. Polystyrene standards were used for calibration. The glass transition temperature ($T_g$) of Arg-Leu PEUUs were tested by a TA Q2000 differential scanning calorimetry (DSC) under a nitrogen gas flow of 50 mL/min. The hydrophilicity of all types of Arg-Leu PEUUs were measured by an Imass CAA2 contact angle analyzer at room temperature as described previously.

Preparation of Arg-Leu PEUU NPs and DOX Encapsulation. The fabrication of Arg-Leu PEUU self-assembled NPs and their DOX loading were performed by a facile dialysis method. In a typical preparation, 10 mg of Arg-Leu PEUU was dissolved in 10 mL of DMSO and then dialyzed against DI water three times (3 L, 6 h; MWCO: 3500 g/mol). The Arg-Leu PEUU NP suspension was formed inside the dialysis bag with gentle stirring. The final concentration of the Arg-Leu PEUU NPs was about 0.9 mg/mL after dialysis (verified after lyophilization). Arg-Leu PEUU-FITC fluorescent NPs were also prepared using the same dialysis method but protected from light.

To formulate DOX-loaded Arg-Leu PEUU NPs, 10 mg of DOX HCl was dissolved and magnetically stirred overnight in 2 mL of DMSO in the presence of 6 mg of TEA to remove the Cl$^-$ of DOX·HCl. A predetermined volume of DOX DMSO solution, as prepared above, was combined with 1 mg/mL Arg-Leu PEUUs in DMSO and dialyzed against DI water three times (3 L, 6 h; MWCO: 3500 g/mol) at room temperature. During the formation of the DOX-loaded Arg-Leu PEUU NPs in the dialysis process, the free DOX and TEA were also removed simultaneously. The DOX-loaded Arg-Leu PEUU NPs were collected by lyophilizing the NP suspension inside the dialysis bag (Labconco Freezone 2.5, Kansas City, Mo.), and the samples were stored at 4° C.

Transmission Electron Microscopy (TEM). TEM images were recorded on a FEI T12 SPIRIT microscope at 120 kV equipped with a LaB6 filament and a SIS Megaview III CCD camera. Samples were prepared by dropping a 0.9 mg/mL Arg-Leu PEUU NP suspension in water onto a copper grid (200 mesh coated with carbon), and excess water was removed using a piece of filter paper at the edge of the copper grid. Phosphomolybdic tungstic acid solution was used to stain NPs to enhance their electron contrast.

NP Size and Zeta Potential Characterization. The size and zeta potential of the Arg-Leu PEUU NPs were measured at 25° C. using a Malvern Zetasizer Nano-ZS machine (Worcestershire, U.K.). 0.9 mg/mL Arg-Leu PEUU NP suspension samples were placed in 1.0 mL plastic cuvettes. The average hydrodynamic particle size was measured by using light scattering. Zeta potentials were calculated by using the Smoluchowsky model for aqueous suspensions.

Encapsulation Efficiency (EE) and Drug Loading Content (DL). The EE and DL of the DOX-loaded Arg-Leu PEUU NPs were measured with a UV-vis spectrophotometer (PerkinElmer Lambda 35, Madison, Wis.) at 480 nm. Five milligrams of freeze-dried DOXloaded NPs were dissolved into 20 mL of DMSO. The concentration of DOX was determined by absorption at a 480 nm wavelength. The DOX content was calculated from the calibration curve over the linear range from 1 to 60 μg/mL.

$$EE = \frac{\text{mass of } DOX \text{ encapsulated in } NPs}{\text{mass of } DOX \text{ used during the } NP \text{ preparation}} \times 100$$

$$DL = \frac{\text{mass of } DOX \text{ encapsulated in } NPs}{\text{mass of the } NPs \text{ with loaded } DOX} \times 100$$

In Vitro Cytotoxicity Assay of Arg-Leu PEUU NPs. 3T3 fibroblasts were maintained in Dulbecco's modified eagle medium (DMEM) supplemented with 10% fetal bovine serum (FBS) and 100 U/mL penicillin-streptomycin. The cytotoxicity of blank Arg-Leu PEUU NPs against 3T3 fibroblasts was evaluated by a standard MTT assay as shown previously. 3T3 fibroblasts were seeded on a 96-well plate with a density of 2000 cells/well. All Arg-Leu PEUU NP samples were suspended in PBS buffer and sterilized under a UV lamp (265 nm wavelength) for 30 min. After washing with PBS, 150 μL of sterilized Arg-Leu PEUU NPs (6-Arg-4-Leu-4 A/L-1/4 or 6-Arg-4-Leu-4 A/G 2/1) at each of the 4 concentrations (diluted to 1 mg/mL, 0.5 mg/mL, 0.2 and 0.1 mg/mL in cell culture media) were added and incubated along with 3T3 cells for 24 and 48 h. Cells cultured with cell culture media were used as controls. After 24 and 48 h, the cell media was removed, washed with PBS, and 100 μL of media containing 10 μL of 5 mg/mL MTT solution (thiazolyl blue tetrazolium bromide in PBS filtered by a 0.22 μm filter) was added to each well following another 4 h of incubation. 150 μL of DMSO was added into each well after removing the media, and the 96-well plate was gently shaken for 30 min at room temperature. The optical absorbance of the DMSO solution in the 96 well plate was measured at wavelengths of 570 and 690 nm (Spectramax plus 384, Molecular Devices, U.S.A.). The cell viability (%) was calculated according to the following equation:

$$\text{viability}(\%) = \frac{OD570(\text{sample}) - OD690(\text{sample})}{OD570(\text{control}) - OD690(\text{control})} \times 100$$

where OD570 (control) and OD690 (control) represent the measurements from the wells treated with cell medium only, and OD570 (sample) and OD 690 (sample) are measurements from the wells treated with various Arg-Leu PEUU NPs. Eight samples of each concentration of 6-Arg-4-Leu-4 A/L-2/1 and 6-Arg-4-Leu-4 A/L-1/4 were analyzed.

Adhesion Assay of Bovine Aortic Endothelial Cells (BAECs) on an Arg-Leu PEUU Substrate. First, 150 μL of 1 mg/mL 6-Arg-4-Leu-4 A/L-2/1 PEUU solution in DMF was coated twice on circular glass coverslips (11 mm diameter), dried at room temperature in a fume hood, and sterilized by 30 min of UV radiation (265 nm). BAECs were seeded onto Arg-Leu-PEUU coated glass coverslips as well as uncoated glass controls at 163 cells/mm$^2$. BAECs were cultured with M199 media supplemented with serum fetal clone III, penicillin-streptomycin, MEM amino acids, and vitamins. After 3 days in culture, the samples were fixed with 3.7% formaldehyde and prepared for scanning electron microscopy (SEM) by dehydration in increasing concentrations of 50%, 70%, 90%, and 100% ethanol solution before freeze-drying. The samples were spin-coated with carbon and images were taken using an SEM (Tescan Mira 3). For fluorescence imaging, samples were fixed, permeabilized using 1% Triton and PBS/0.02% Tween washes, and blocked with PBS/0.02% Tween/3% bovine serum albumin. Primary vinculin antibody (1:100) and secondary antibody (1:200, Alexa Flour 488) were both incubated overnight. Actin was stained with phalloidin (1:100, Alexa Flour 568) for 1 h, and the nucleus was stained with DAPI (1:100) for 10 min. Images were acquired on a laser scanning confocal microscope (Carl Zeiss LSM 700, Germany) using a 40×water-immersion objective.

Inflammatory Response Assays (TNF-α, Nitric Oxide, IL-10 373 Production) of RAW 264.7 Macrophages Treated with Arg-Leu 374 PEUU NPs. RAW 264.7 macrophages (provided by Dr. Cynthia Leifer, Cornell Veterinary College) were grown at 37° C. and 5% $CO_2$ in DMEM supplemented with 10% fetal bovine serum (with 1% penicillin-streptomycin, 4-(2-hydroxyethyl)-1-piperazineethanesulfonic acid (HEPES), L-glutamine and sodium pyruvate). A total of 1×10$^5$ RAW 264.7 mouse macrophages were plated in each well of a 24-well plate and cultured for 24 h at 37° C. and 5% $CO_2$. RAW 264.7 macrophages on tissue culture plates in media were used as a negative control group, and macrophages stimulated with 100 µL of 100 ng/mL lipopolysaccharide (LPS) were used as a positive contrast.

TNF-α assay: RAW 264.7 macrophages were treated with 1 and 2 mg/mL NPs or LPS for 24 h. The supernatants were harvested, centrifuged (500 g, 15 min, 4° C.) and measured using an ELISA kit according to the manufacturer's instruction (Biolegend, San Diego, Calif.). Briefly, 100 µL of pretitrated diluted capture antibody (1:200) in the coating buffer were added to each well of the 96-well plate (8.4 g of NaHCO$_3$, 3.56 g of Na$_2$CO$_3$, DI water added up to 1 L, and the pH was adjusted to 9.5) and allowed to incubate overnight at 4° C. The next day, the plate was washed four times with wash buffer (0.5% Tween 20 in 1×PBS), and an assay diluent (1% BSA in 1×PBS) was added to block nonspecific binding. After 1 h, the plate was washed four times, and the culture supernatants were added to wells and allowed to incubate for 2 h at room temperature. Afterwards, the plate was washed four times, 100 µL of detection antibody was added to the diluted supernatants, and the plate was incubated at room temperature for 1 h and washed 4 times. After the plate was blotted dry, 100 µL of avidin-horse radish peroxidase was added to each well (diluted 1:1000 in assay diluent) and incubated at room temperature for 30 min. The plate was blotted dry, and 100 µL of tetramethylbenzidine (TMB) solution (Sigma-Aldrich) was added to each well and allowed to incubate at room temperature for 20 min in the dark. Finally, 100 µL of 2 N $H_2SO_4$ solution was added to each well, and the plate was read at 450 nm using a BioRad plate reader. TNF-α concentrations were calculated using the standard curve generated from the recombinant murine TNF-α standard with 2-fold serial dilutions from 7.8 to 500 pg/mL. Three replicate wells were tested, and the average TNF-α release (corrected for volume and expressed as total release from the specified cell count) and standard error of the mean were determined.

NO production: The Arg-Leu PEUU NP samples were diluted to 1 and 2 mg/mL, and the LPS and blank control were individually incubated for 24 h with 1×10$^5$ RAW 264.7 macrophages at 37° C. and 416 5% $CO_2$. The nitrate content was measured by the Griess reagent system (Promega, Madison, Wis.). Then, 50 µL of cell-free culture supernatant samples were taken from the cell culture with the hydrogel samples and control groups, mixed with 50 µL of a sulfanilamide solution (1% sulfanilamide in 5% phosphoric acid) and incubated for 5 to 10 min at room temperature, and protected from light. Then, 50 µL of NED solution (0.1% N-1-naphthylethylenediamine dihydrochloride in water) was dispensed to all wells, and incubated at room temperature for 5 to 10 min, and protected from light. The absorbance was measured within 30 min in a plate reader at 540 nm. Nitrite concentration was calculated with a sodium nitrite standard curve generated for each experiment. Three samples of each hydrogel type and control groups were tested, and the mean values were calculated with a standard deviation.

IL-10 assay: The production of IL-10 from RAW 264.7 macro-phages after 24 h of NP treatment was measured using the corresponding ELISA MAX mouse kit (Biolegend, San Diego, Calif.) by a plate reader at a wavelength of 450 nm according to the manufacturer's instructions.

Hemolysis. Hemolytic activity of two representative Arg-Leu PEUU NPs (6-Arg-4-Leu-4 A/L-2/1, 6-Arg-4-Leu-4 A/L-1/1) was evaluated according to a reported protocol with minor modifications. The hemolysis rate of the branched PEI, (Mn 1800 g/mol) which is a water-soluble cationic polymer widely studied as a nonviral gene delivery carrier, was tested for comparison. Phosphate buffers (PB) in the pH range of 5.9 to 7.4 were prepared to be isosmotic. Briefly, red blood cells (RBCs) were isolated from whole bovine blood by centrifugation and then diluted by PB (RBC:PB=1:49) into four pH solutions (pH 5.9, 6.2, 6.8, and 7.4). Ten µL of sterilized Arg-Leu PEUU NPs suspended in a buffer or PEI in buffer solution were added to 190 µL of diluted RBC suspension at systematically varied concentrations (40 µg/mL, 5 µg/mL and 1 µg/mL in the suspension with diluted RBCs) and then incubated at 37° C. for 1 h. Ten µL of PB or 10 µL of 20 wt % Triton X-100 were added to 190 µL of the diluted RBC suspension and used as negative and positive controls, respectively. Then RBCs were centrifuged at 500 RCF for 5 min and 100 µL of the supernatant were transferred to new 96-well plates and measured with a spectrophotometer (Spectramax plus 384, Molecular Devices, USA) at 405 nm. The hemolysis ratio (HR) of the Arg-Leu PEUU NPs was calculated using the following formula:

$$\text{hemolysis}(\%) = \frac{OD\,(\text{sample}) - OD\,(\text{negative control})}{OD\,(\text{positive control}) - OD\,(\text{negative control})} \times 100$$

where OD (sample), OD (negative control), and OD (positive control) were denoted as the absorbance of samples and the negative and positive controls, respectively. All hemolysis experiments were carried out in quadruplicates.

Cellular Uptake of Arg-Leu PEUU NPs (HeLa Cells). HeLa cells were maintained in DMEM with 10% FBS and 1% penicillin-streptomycin and seeded on circular glass coverslips in 24-well plates at a density of $2 \times 10^4$ cells/well and incubated for 24 h at 37° C. For the cellular internalization study, HeLa cells were incubated along with the FITC-labeled 6-Arg-4-Leu-4 A/L-1/4 NPs, the DOX loaded 6-Arg-4-Leu-4 A/L-1/4 NPs at an equivalent DOX concentration of 5 μg/mL in DMEM, or the free DOX. After incubation for 4 h at 37° C., cells were washed twice with ice cold PBS and fixed with fresh 4% paraformaldehyde in PBS for 30 min at room temperature. The coverslips were then mounted onto glass microscope slides with a drop of antifading mounting agent containing DAPI. Samples were kept in the dark at 4° C. overnight before imaging. The cellular uptake of the Arg-Leu PEUU NPs and their DOX-loaded NP was visualized with confocal laser scanning microscopy (Carl Zeiss LSM 710, Germany). Flow cytometry (BD FACS Aria Fusion flow cytometry) was employed for quantitative cell uptake analysis. HeLa cells were seeded on 6-well plates at $5 \times 10^5$ cells/well. After incubation for 24 h, the cells were treated with various FITC-labeled Arg-Leu PEUU copolymer NPs (300 μg/mL in DMEM media containing 10% FBS) at 37° C. for 4 h. After incubation, the medium was removed and cells were washed with PBS. The harvested cells were collected by centrifugation (200 rcf, for 5 min) followed by flow cytometric analysis (using a Brilliant Violet 605 filter) immediately. The mean fluorescence intensity of $2 \times 10^4$ cells was recorded for each sample.

In Vitro Release of DOX from Arg-Leu PEUU NPs. The in vitro release of DOX from Arg-Leu PEUU NPs was investigated using dialysis bags (MWCO: 10,000 g/mol) at 37° C. Briefly, 5 mg of DOX-loaded Arg-Leu PEUU NPs (6-Arg-4-Leu-4 A/L-2/1 or 6-Arg-4-Leu-4 A/G-1/4 with 20 wt % DOX initial loading) were suspended in 5 mL of DI water and poured into a dialysis bag. The dialysis bags were immersed in 50 mL of 0.1 M Tris buffer (pH of 5.5 or pH of 7.4) in capped glass bottles, which were placed in a shaking incubator at 37° C. (Julabo, water bath). At predetermined time internals, three 1 mL solution samples were taken from the release medium, and 3 mL of fresh buffer was added to maintain a constant volume. The concentration of DOX released into the buffers was measured using a UV-vis spectrophotometer at 480 nm as described above.

Cytotoxicity Assay of DOX-Loaded Arg-Leu PEUU NPs. The cytotoxicity of DOX-loaded Arg-Leu PEUU NPs on HeLa cells was evaluated by the MTT assay. The HeLa cells were seeded onto 96-well plates at $7 \times 10^3$ cells/well and incubated for 24 h. Free DOX was prepared by using TEA to remove the counter $Cl^-$ ion of DOX in DMSO, purified by dialysis against DI water, and then freeze-dried. Free DOX in 150 μL of cell culture media at four concentrations (5 μg/mL, 2 μg/mL, 0.5 μg/mL and 0.1 μg/mL) or sterilized 6-Arg-4-Leu-4 A/L-1/4, 6-Arg-4-Leu-4 A/L-2/1 NPs suspended in cell culture media with the equivalent amount of DOX loaded were incubated with the HeLa cells for 1, 4, or 24 h at 37° C. The media was then removed, and the cells were washed twice with PBS. Fresh media was added and the HeLa cells were further incubated with fresh media for an additional 48 h at 37° C. Afterwards, the cells were incubated with 150 μL of media containing 15 μL of 5 mg/mL MTT per well for 4 h at 37° C. Then the supernatant was removed, and 150 μL per well of DMSO was added. The cell viability (%) was measured and calculated using the MTT assay protocol described above. Statistical Analysis. All data are presented as mean values with standard deviations (SD). Statistical analysis was performed with oneway ANOVA test, and $p<0.05$ was considered statistically significant.

TABLE 6

Molecular Weight, Glass Transition Temperature, and Static Water Contact Angle Characterization of Arg-Leu PEUU Series Synthesized from Different Feed Ratios of the Four Building Blocks: Di-Hydrochloride Acid Salt of Bis (L-Arg) Butane Diester, Bis (L-Leu) Butane Diester, Glycerol α-Monoallyl Ether, and 1,6 Hexamethylene Diisocyanate[b].

| Arg-Leu PEUU abbreviations | reactants | molar feed ratio (Arg-4-Cl: Leu-4: GAE: HDI) | $M_n$ (g/mol) | $M_w$ (g/mol)[b] | PDI | $T_g$ (° C.) | water contact angle (deg) |
|---|---|---|---|---|---|---|---|
| 6-Leu-4 | Leu-4, GAE, HDI | 0:4:1:5 | N/A | N/A | N/A | −4.8 | 66.2 ± 1.9 |
| 6-Arg-4-Leu-4A/L-1/4 | Arg-4-Cl, Leu-4, GAE, HDI | 4:16:5:25 | 11628 | 16802 | 1.45 | −4.6 | 59.3 ± 5.2 |
| 6-Arg-4-Leu-4 A/L-1/2 | Arg-4-Cl, Leu-4, GAE, HDI | 4:8:3:15 | N/A | N/A | N/A | −4.1 | 53.1 ± 3.9 |
| 6-Arg-4-Leu-4 A/L-1/1 | Arg-4-Cl, Leu-4, GAE, HDI | 2:2:1:5 | 9681 | 14336 | 1.48 | −3.7 | 47.4 ± 2.0 |
| 6-Arg-4-Leu-4 A/L-2/1 | Arg-4-Cl, Leu-4, GAE, HDI | 8:4:3:15 | 9770 | 13420 | 1.37 | −3.4 | 39.7 ± 4.7 |
| 6-Arg-4 | Arg-4-Cl, GAE, HDI | 4:0:1:5 | N/A | N/A | N/A | −2.9 | 33.5 ± 4.1 |

[a]The sample labels for the Arg-Leu PEUU polymers are ascribed as 6-Arg-4-Leu-4 A/L-m/n, where 6 is the number of methylene groups in the hexamethylene diisocyanate (HDI), 4 is the number of methylene groups in the amino acid alkylene diester, A/L-m/n is the molar ratio of Arg-4-Cl (A) to Leu-4 monomer (L).
[b]Molecular weight tested by GPC with DMF/LiBr solvent.

Results and Discussion.

Figure 13:
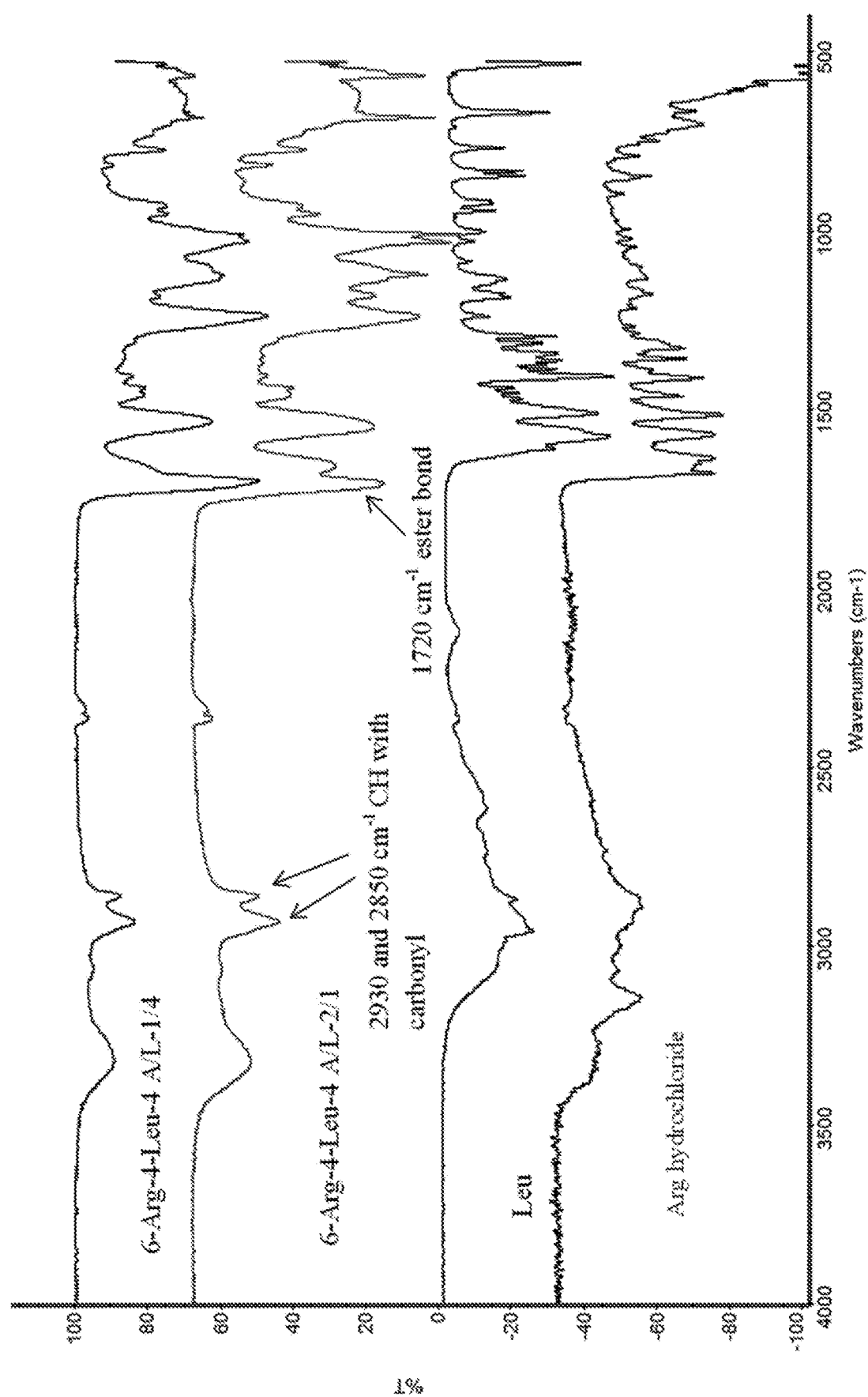
FIG. 13 shows FTIR spectra of representatives Arg-Leu PEUU, 6-Arg-4-Leu-4 A/L-1/4, 6-Arg-4-Leu-4 A/L-2/1, and Leu and Arg hydrochloride.

Synthesis and Characterization of Arg-Leu PEUU Block Copolymers. FTIR and H NMR spectra were obtained to verify the chemical composition of Arg-Leu PEUUs. For FTIR, the bands 3290 $cm^{-1}$ (NH vibration) and 1720 $cm^{-1}$ (ester) and the two bands 2930 and 2850 $cm^{-1}$ (symmetric and nonsymmetric stretching of the C—H with carbonyl)

were seen on all Arg-Leu PEUU spectra, as shown in FIG. 13. The absorbance at 1675 cm$^{-1}$ has been ascribed to the C—N vibration, and the absorbance at 1635 cm$^{-1}$ is in a frequency range characteristic of C=N bonds as shown on the spectra of Arg and 6-Arg-4-Leu-4 A/L-2/1. The absorbance of the same C—N of 6-Arg-4-Leu-4 A/L-2/1 is weaker due to its lower Arg content.

Figure 23:
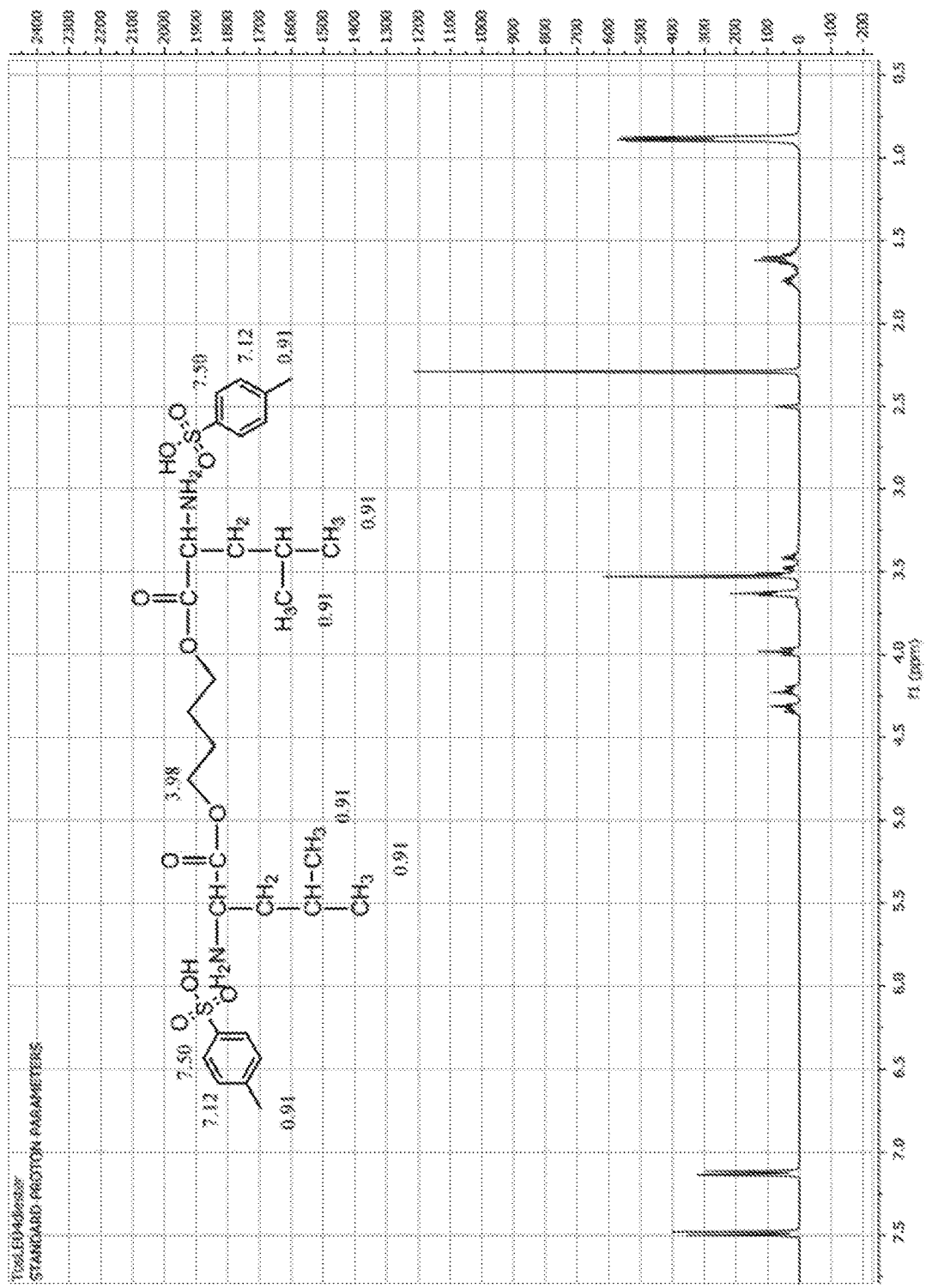
FIG. 23 shows $^1$H-NMR spectroscopy of (A) di-p-toluene sulfonic acid salt of bis (L-Leu) butane diesters (Leu-4) and (B) 6-Arg-4-Leu-4 PEUU A/L-1/4.
Figure 23:
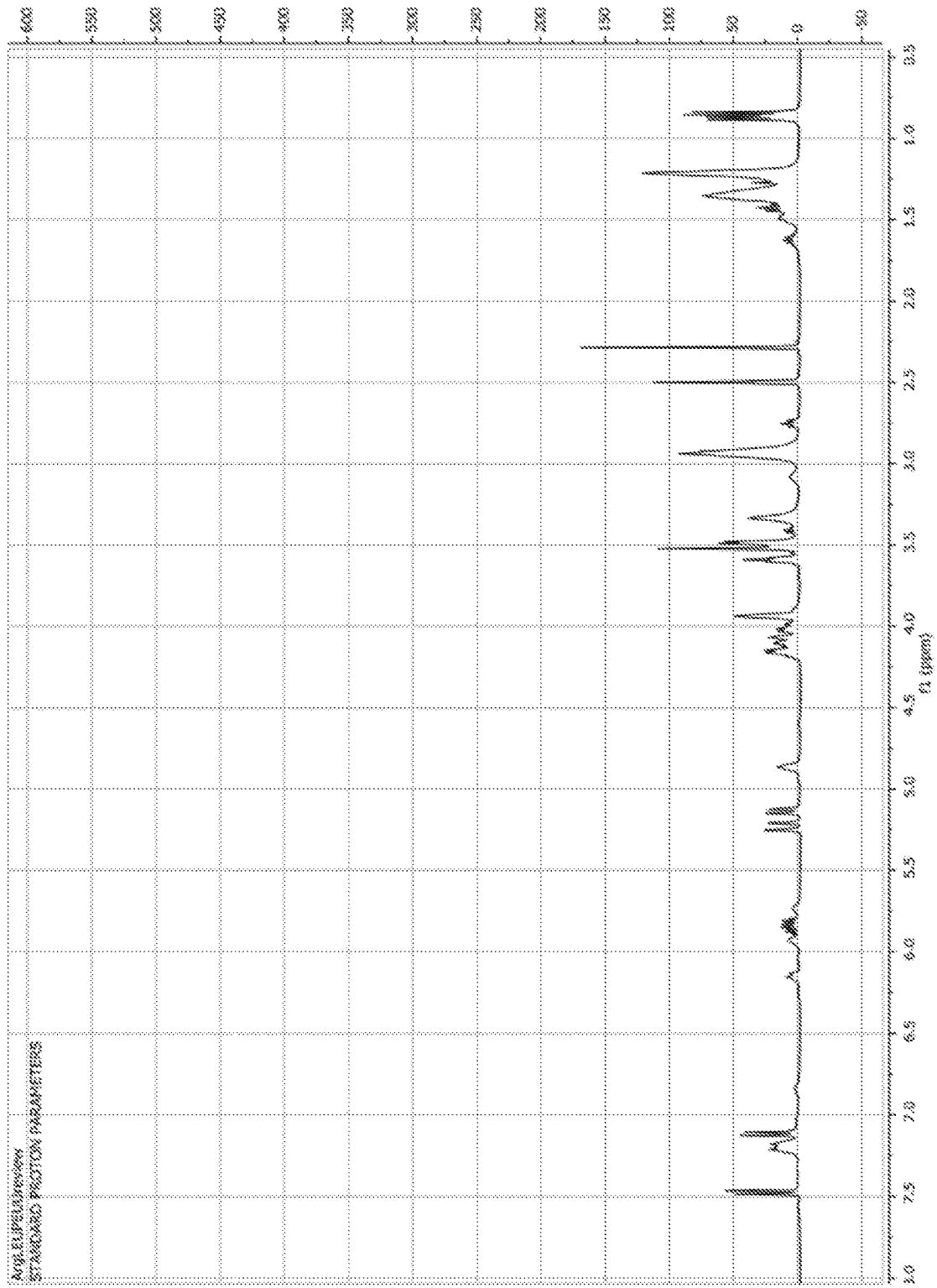

$^1$H NMR (FIG. 23) was also recorded. For example, the $^1$H NMR of 6-Arg-4-Leu-4 A/L-1/4 PEUU (DMSO-d$_6$, ppm, δ) is 1.50 [—CH$_2$—CH$_2$—CH$_2$—NH—], 4.14 [—(O)C—O—CH$_2$—CH$_2$—], 1.63 [—OC(O)—CH(NH$^{3+}$)—CH$_2$—CH$_2$—CH$_2$—NH—], 2.73 [—(CH$_2$)$_2$—CH$_2$—NH—], 4.08 [—(O)C—O—CH$_2$—CH$_2$—], 1.49 [CH$_2$CH(CH$_3$)$_2$], 0.91 [CH$_2$CH—(CH$_3$)$_2$].

The number-average molecular weight (Mn) of Arg-Leu PEUUs ranged from 9681 g/mol to 11,628 g/mol (Table 1), which is lower than Arg-PEUU Mn (33,000-44,600 g/mol), most likely because the four reactants in the system introduced a larger stoichiometry variation in the reaction, which may lead to a decreased molecular weight in polymerization.

As shown in Table 6, Arg-Leu PEUUs with different Arg to Leu ratios have water contact angles ranging from 59.3±5.2° to 39.7±4.7°, and hence the hydrophilicity or hydrophobicity of Arg-Leu PEUU could be easily adjusted by the feed ratio of Arg-4-Cl to Leu-4 building blocks. Arg-Leu PEUU with higher Arg-4-Cl contents (i.e., less Leu-4) produced a more hydrophilic copolymer with a lower contact angle.

The dependence of the water contact angle on the feed ratio of the hydrophilic to hydrophobic components as observed in the current Arg-Leu PEUUs copolymer system is also reported by other published studies using different polymer systems. For example, both hydrophobic and hydrophilic building blocks were previously used to develop a new copolymer system composed of oleyl 2-acetamido-2-deoxy-α-D-glucopyranoside methacrylate and vinylpyrrolidone building blocks with a distinct hydrophilicity difference. By tuning the feed ratio of the building blocks, it was previously reported that the resulting copolymer had a water contact angle ranging from 34.1 to 81.4° and could also be self-assembled into NPs (ranging from 144 to 395 nm in diameter), as we also found in our current Arg-Leu PEUU copolymer. Similarly, it was reported that the water contact angle of the Arg-Phe PEA amphiphilic copolymers also depended on the Arg to Phe contents. The 6-Leu-4 PEUU control in the current study has a contact angle 17% lower than the 8-Phe-4 PEA control in the previous report, i.e., 66.2° vs 79.6°. Even the contact angles of the hydrophobic Arg-Leu PEUU samples in the current study (average value of 59.3°) are significantly lower than the contact angles from the commercially available absorbable poly-ε-caprolactone (PCL) biomaterials (90.9°).

Although the T$_g$ of Arg-Leu PEUU (Table 6) is within a tight range of −3.4 to −4.8° C., a higher Arg content in the Arg-Leu PEUU contributed to a slightly higher T$_g$ due to the more bulky pendant guanidino groups and hydrogen bond interactions in the Arg-diester block. All of the T$_g$ values of Arg-Leu PEUUs are lower than 0° C., indicating the mobility of the segments of Arg-Leu PEUUs in a microscopic scale at room temperature. The flexible and amphiphilic nature of the Arg-Leu PEUU polymer chain building blocks enables the Arg-Leu PEUU to self-assemble into nanoscale spherical particles in an aqueous medium at room temperature without using mechanical stirring or an emulsifier, as is required for other polymer systems.

Figure 25:
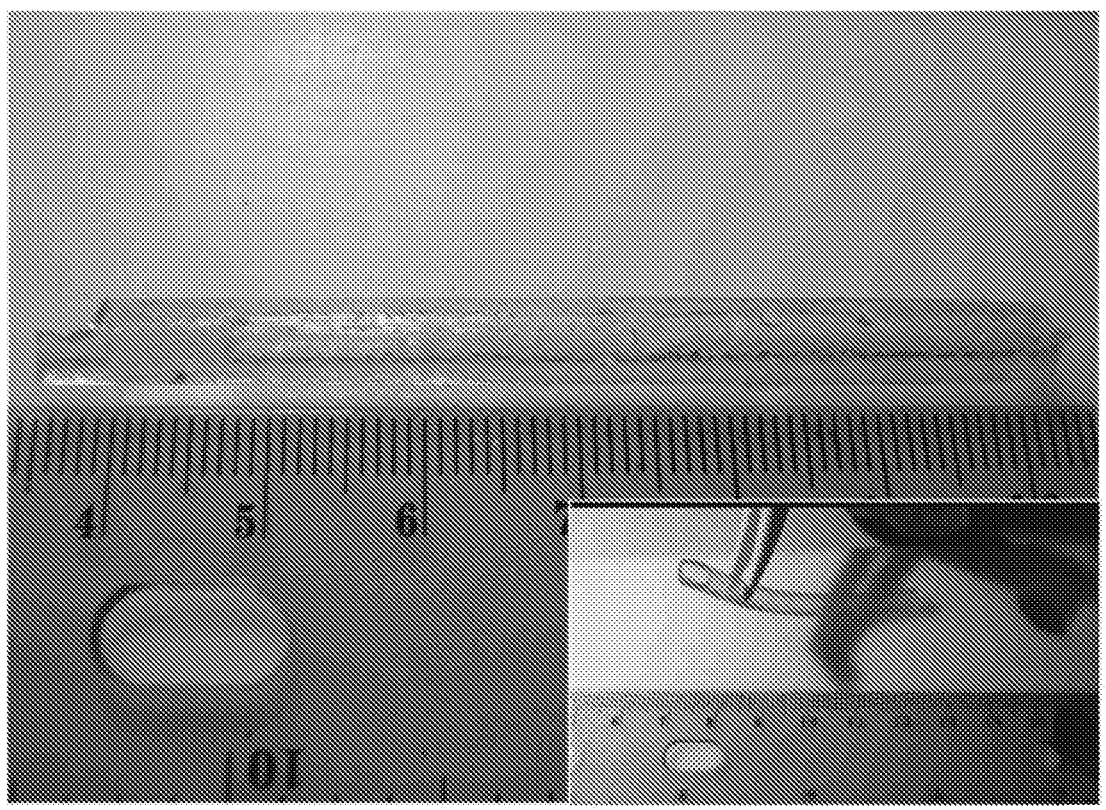
FIG. 25 shows Arg-Leu PEUU (6-Arg-Leu PEUU A/L-1/4) elastomer tube fabricated by 20 min UV crosslinking (365 nm, 0.5 wt % Irgacure 2959) in its ethanol solution (70 wt %). The good cell adhesion and quick processing and shaping make Arg-Leu PEUUs ideal biomaterials for biomedical applications by 3D printing.

FIG. 24 shows the solubility of the newly synthesized Arg-Leu PEUU. One of the notable benefits of incorporating Leu-4 building block into Arg-PEUU is that the resulting Arg-Leu PEUUs become highly soluble (>60 wt %) in ethanol and methanol, while Arg-PEUU does not. Due to the incorporation of Leu building blocks, the concentrated Arg-Leu PEUU solution in ethanol can be photo-cross linked (365 nm UV, Irgacure 2959), and then will quickly solidify after the ethanol evaporates. This technique could be used to fabricate biomedical devices with complex shapes, such as a flexible tubular structure of 2-3 mm inner diameters (FIG. 25).

To study the relationship between polymer structures and properties, 6-Leu-4 and 6-Arg-4 PEUU (as control samples), and 4 types of Arg-Leu PEUU samples with different Arg-4-Cl to Leu-4 diester feed ratios, were synthesized and their composition details are listed in Table 6. A representative chemical structure of the repeating unit of Arg-Leu PEUU is shown in FIG. 12. Arg-4-Cl and Leu-4 (x=4) were chosen as the monomers to synthesize Arg-Leu PEUUs for two purposes: to avoid the cytotoxicity of ethylene glycol (x=2), which might be present in the final degradation product of Arg-Leu PEUU, and to reduce the size of Arg-Leu PEUU NPs. This was accomplished through the use of a less hydrophobic diester building block like an amino acid butane diester (x=4), whereas the use of the amino acid hexane diester (x=6) which led to larger Arg-Leu PEUU NP size.

Characterization of Arg-Leu PEUU NPs and DOX Loading. The combination of a light scattering technique (zetasizer) and an imaging method (TEM) was used to characterize the resulting Arg-Leu PEUU NP morphology. The number-average of particle diameters of Arg-Leu PEUUs ranged from 187 to 272 nm, depending on the Arg-4-Cl to Leu-4 diester feed ratio (Table 7).

TABLE 7

Characterizations of Arg-Leu PEUU Self-Assembled NPs and Their DOX-Loaded Nanoparticles As a Function of Arg (A) to Leu (L) Diester Feed Ratio.

| self-assembled nanoparticles | number-average diameter (nm) at 25° C. | polydispersity | zeta potential (mV) |
|---|---|---|---|
| 6-Leu-4 PEUU | 352.2 ± 5.4 | 0.33 | +1.6 ± 2.1 |
| 6-Arg-4-Leu-4 A/L-1/4 | 247.3 ± 3.5 | 0.34 | +31.2 ± 0.7 |
| 6-Arg-4-Leu-4 A/L-1/2 | 243.1 ± 6.6 | 0.36 | +32.9 ± 1.5 |
| 6-Arg-4-Leu-4 A/L-1/1 | 191.3 ± 8.6 | 0.33 | +35.4 ± 1.6 |
| 6-Arg-4-Leu-4 A/L-2/1 | 187.6 ± 2.8 | 0.40 | +40.9 ± 1.5 |
| 6-Arg-4-Leu-4 A/L-1/4 with 20 wt % DOX initially loaded | 272.3 ± 7.4 | 0.39 | +34.7 ± 1.1 |
| 6-Arg-4-Leu-4 A/L-2/1 with 20 wt % DOX initially loaded | 204.0 ± 4.6 | 0.42 | +40.3 ± 1.7 |

Figure 14:
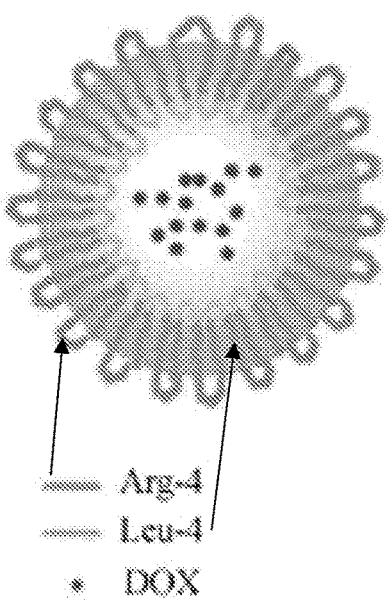
FIG. 14 shows (A) a schematic illustration of DOX loaded Arg-Leu PEUU NP, (B) representative TEM image of self-assembled Arg-Leu PEUU NPs in deionized water, (C) representative TEM image of 14.2 wt % DOX loaded 6-Arg-4-Leu-4 A/L-1/4 NP.
Figure 14:
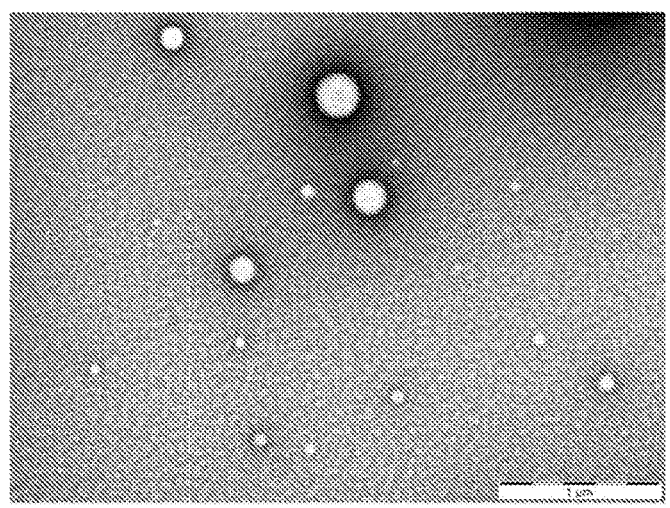
Figure 14:
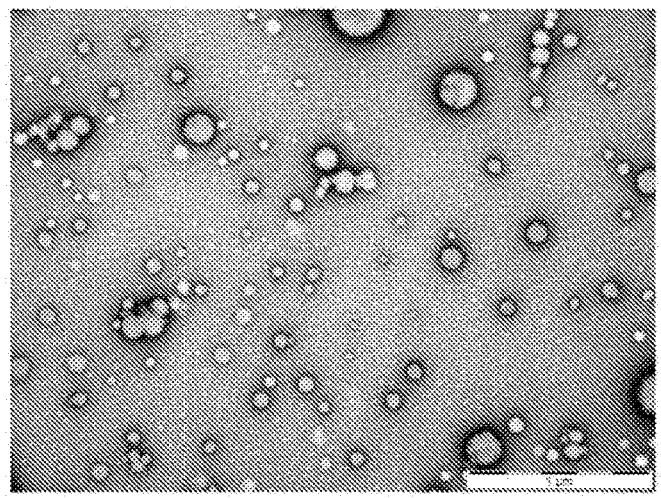

Increasing the hydrophilic Arg-4-Cl diester content in the Arg-Leu PEUUs led to a smaller particle size, possibly because the NPs are able to be stabilized with a smaller hydrophobic core. The zeta potential of the Arg-Leu PEUU NPs ranged from +31.2 to +40.9 mV, indicating that these NPs were positively charged in an aqueous environment due to the ionization of the guanidino group on the Arg located on the exterior surface of the Arg-Leu PEUU NPs. Increasing the A/L, ratio led to NPs with a higher positive zeta potential. The schematic illustration of Arg-Leu PEUU self-assembled NPs is presented in FIG. 14A. Compared to the previously reported Arg-Phe PEAs NPs, which have an average particle size of 110 nm and a zeta potential of +28.9 mV, the current Arg-Leu PEUU NPs are larger and more cationic. To prepare the DOX loaded Arg-Leu PEUU NPs, DOX hydrochloride (along with excess TEA) and Arg-Leu PEUUs were dissolved in DMSO and dialyzed against DI water. In this simple process, the alkaline condition due to the presence of TEA in the dialysis bag rendered DOX hydrochloride to be unprotonated (i.e., becoming more hydrophobic), thereby facilitating the incorporation of unprotonated DOX into the hydrophobic core in the Arg-Leu PEUU NPs. Using such a strategy, a final 13.2-14.2 wt % DOX could physically be incorporated into the Arg-Leu PEUU NPs (Table 8). This DOX loading efficiency in the Arg-Leu PEUU NPs is similar to the previously reported polymersome carriers. The TEM images of the self-assembled 6-Arg-4-Leu-4 A/L-1/4 NPs and their DOX-loaded self-assemblies showed a spherical morphology with a diameter ranging from 100 to 300 nm (FIG. 14B). At higher DOX loading amounts (i.e., 20 wt %) in the 6-Arg-4-Leu-4 A/L-1/4 NPs, there was slight NP aggregation (FIG. 14C). After DOX loading, the size of the Arg-Leu PEUU NPs was increased by about 10%, and the zeta potential did not present a distinct difference when compared to the unloaded NPs (Table 7). Using a dialysis method to prepare DOX-loaded Arg-Leu PEUU NPs at 30 wt % DOX or higher usually led to a solid aggregation that precipitated out during the dialysis process (Table 8). Hence, only the 20 wt % DOX loading case was used for subsequent biological studies.

TABLE 8

DOX Loading Content and Loading Efficiency in Arg-Leu PEUU NPs.

| feed weight ratio (%) | 6-Arg-4-Leu-4 A/L-1/4 | | 6-Arg-4-Leu-4 A/L-2/1 | |
|---|---|---|---|---|
| | loading content (%) | loading efficiency (%) | loading content (%) | loading efficiency (%) |
| 10 | 7.6 | 76 ± 4 | 7.0 | 70 ± 4 |
| 20 | 14.2 | 71 ± 5 | 13.2 | 66 ± 3 |
| 30 | aggregation | | aggregation | |

Figure 15:
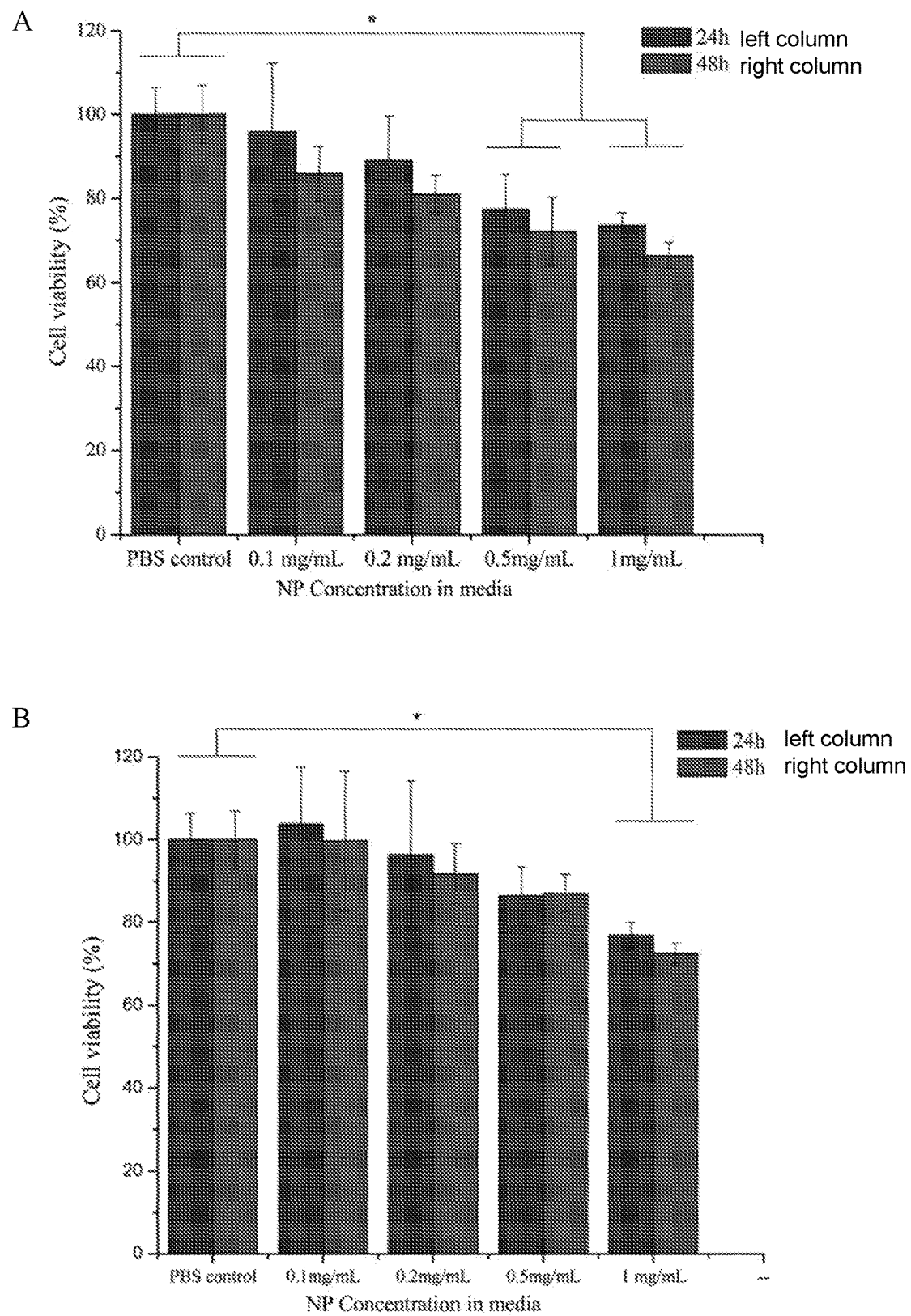
FIG. 15 shows 3T3 cell viability after incubation with blank Arg-Leu PEUU NPs at different concentrations for 24 and 48 h, using (A) 6-Arg-4Leu-4 A/L-1/4; (B) 6-Arg-4-Leu-4 A/L-2/1. * $p<0.05$ for Arg-Leu PEUU NP groups vs PBS control groups.

Biocompatibility of Arg-Leu PEUU NPs. Cytotoxicity of blank Arg-Leu PEUU NPs toward normal mammalian cells (3T3 fibroblasts) was evaluated as shown in FIG. 15. The Arg-Leu PEUU NPs show reasonable cell viability (75% and above), except at the highest 1 mg/mL concentration incubated for 48 h, which shows 68% viability using 6-Arg-4-Leu-4 A/L-1/4 NPs and 73% viability using 6-Arg-4-Leu-4 A/L-2/1 NPs. An increase in the Arg to Leu feed ratio led to a higher cell viability over the whole concentration and incubation periods, e.g., 6-Arg-4-Leu-4 A/L-2/1 versus 6-Arg-4-Leu-4 A/L-1/4. It should be noted that the concentration of the Arg-Leu PEUU NPs used as the DOX nanocarriers in the subsequent studies was not higher than 50 μg/mL, and therefore, the blank Arg-Leu PEUU NPs at this concentration would not impose cytotoxicity to cells.

Figure 16:
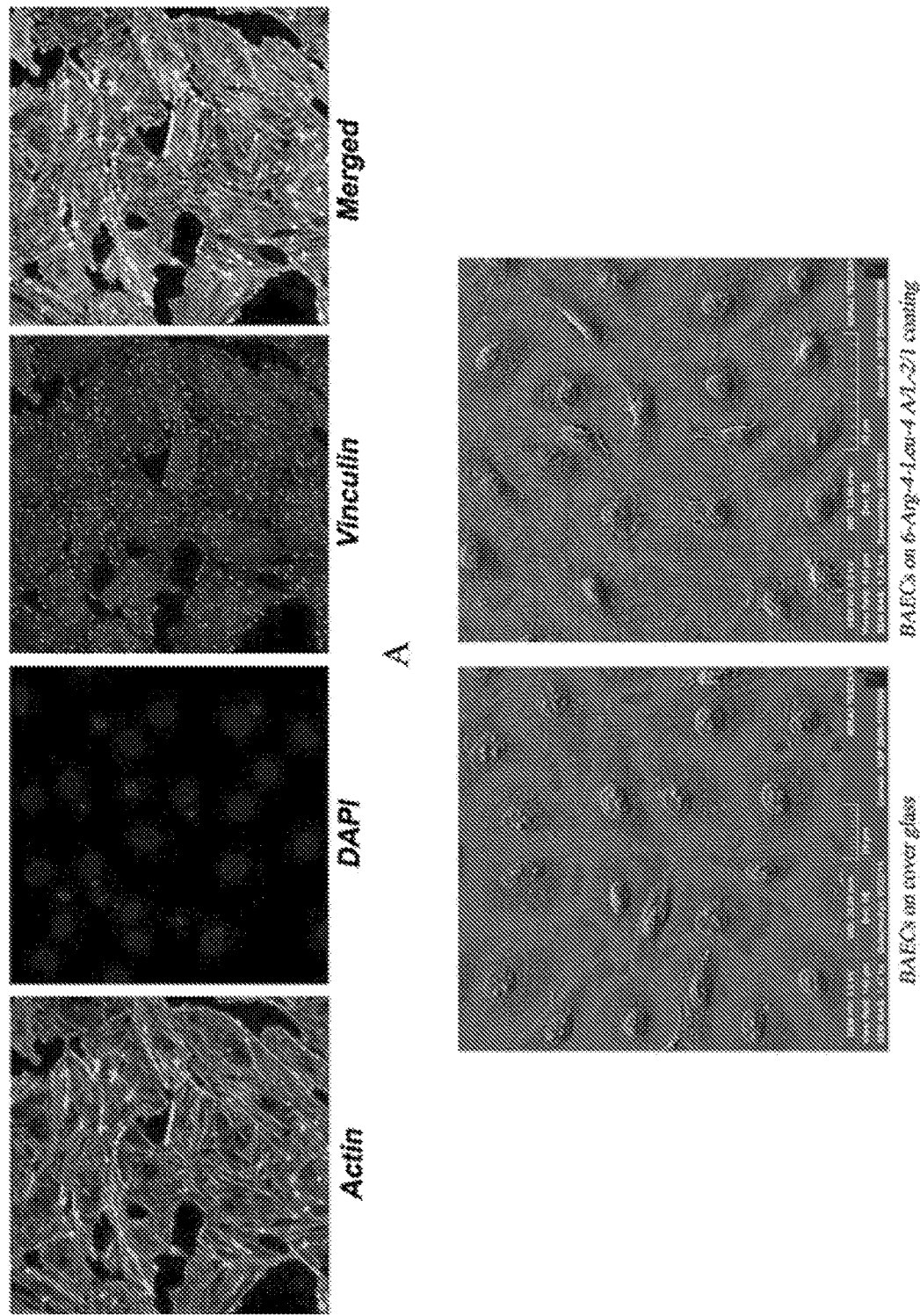
FIG. 16 shows BAECs are adhered onto the Arg-Leu PEUU biomaterial after culture for 3 days. (A) fluorescent images of BAECs adhered onto the 6-Arg4-Leu-4 A/L-2/1 coated layer, stained for actin (first frame from left), DAPI (second frame from left), and vinculin (third frame from left); (B) SEM images, left: cells on cover glass; right: cells on the 6-Arg-4-Leu-4 A/L-2/1 coating.

BAEC Attachment and Adhesion on Arg-Leu PEUU. BAECs were seeded onto both glass coverslips and 6-Arg-4-Leu-4 A/L-2/1 coated coverslips for 3 days, and cellular attachment was analyzed using fluorescence for actin and vinculin, and morphology by SEM imaging (FIG. 16). Cells on the Arg-Leu PEUU biomaterial exhibit a cobblestone morphology (FIG. 16B) similar to those on the glass substrates, and cell-matrix attachments on the Arg-Leu PEUU are clearly evident in the actin/vinculin merged image (FIG. 16A). These image data indicate that the Arg-Leu PEUU biomaterial allows for endothelial cell viability and adhesion.

Figure 17:
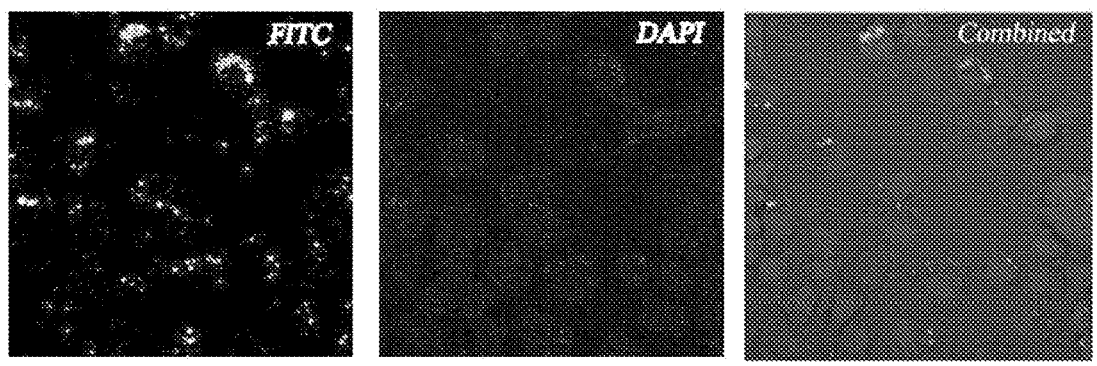
FIG. 17 shows confocal laser scanning microscopy images of the uptake of Arg-Leu PEUU NPs with and without loaded DOX by HeLa cells after 4 h of incubation at 37° C.
Figure 17:
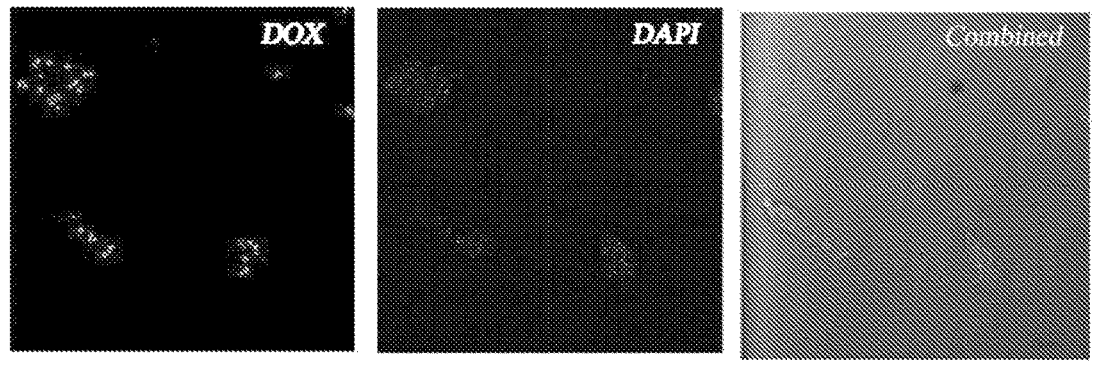
Figure 17:
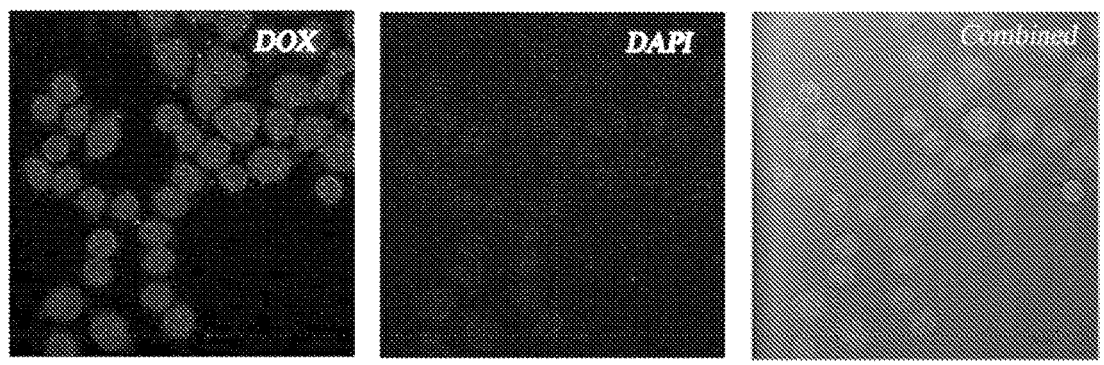
Figure 17:
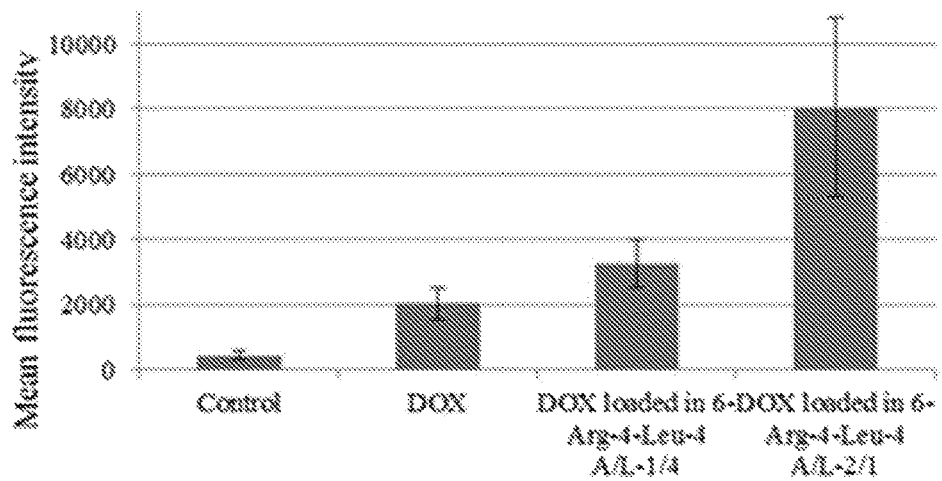

Arg-Leu PEUU NP Cellular Uptake. To investigate the cellular internalization of the Arg-Leu PEUU and DOX-loaded NPs, the free DOX, FITC-labeled, and DOX-loaded Arg-Leu PEUU NPs were incubated with HeLa cells for 4 h at 37° C. The cells were then observed by using confocal laser scanning microscopy (FIG. 17). The merged fluorescent images of DAPI and FITC channels provide clear visual evidence (green fluorescence) of the blank Arg-Leu PEUU NPs engulfed by HeLa cells (FIG. 17A). The red fluorescence of the DOX-loaded Arg-Leu PEUU NPs (FIG. 17B) showed a similar distribution inside the HeLa cells. The free DOX-treated HeLa cells (FIG. 17C) demonstrate increased red fluorescence concentrated around the cell nuclei.

The quantified DOX fluorescence intensity inside of the HeLa cells (FIG. 17D) shows that the DOX-loaded Arg-Leu PEUU NPs have a higher DOX fluorescence intensity than the free DOX. The Arg-Leu PEUU NPs with higher Arg contents (i.e., 6-Arg-4-Leu-4 A/L-2/1 NP carriers) exhibited the highest DOX fluorescence intensity, indicating that at higher Arg contents the Arg-Leu PEUU NPs would have a higher DOX delivery efficiency, which is probably related to its stronger cationic charge and better hydrophilic and hydrophobic balance. These quantified DOX fluorescence intensity data are also consistent with the observed quantitative HeLa cell cytotoxicity study, which will be described in FIG. 21B later.

The higher DOX fluorescence signal in the HeLa cells from the DOX-loaded Arg-Leu PEUU NPs can be attributed to the cationic nature of the Arg moiety in the Arg-Leu PEUU NP carriers that may promote an interaction between the cationic carrier and the anionic charged cell membrane, particularly cancer cells. Similarly, an 8.8-fold improved HeLa cell internalization of DOX delivered by cationic poly N-(2-hydroxypropyl) methacrylamide-co-N-3-aminopropylmethacrylamide hydrochloride (poly-HPMA-co-APMA) NPs when compared to the neutral poly(HPMA) NP carrier was reported, which could be largely attributed to the enhanced electrostatic interaction between the cationic carrier and negatively charged cell membrane.

The versatility of the chemical design in Arg-Leu PEUU copolymers includes the option of an additional capability to functionalize the available pendant double bonds in the copolymer backbone, e.g., converting to amine, hydroxyl, or carboxyl groups via thiol-ene reaction, as demonstrated in previous studies. The additional capability of functionalizing this new family of cationic Arg-Leu PEUU biomaterials could open new options, such as coupling the functionalized cationic Arg-Leu PEUU biomaterials with a wide range of targeting molecules such as folic acid and peptides. It is expected that this technique can be used to target cancer cells and further enhance specific targeting for cancer therapy through the functionalized Arg-Leu PEUU NP system.

Figure 18:
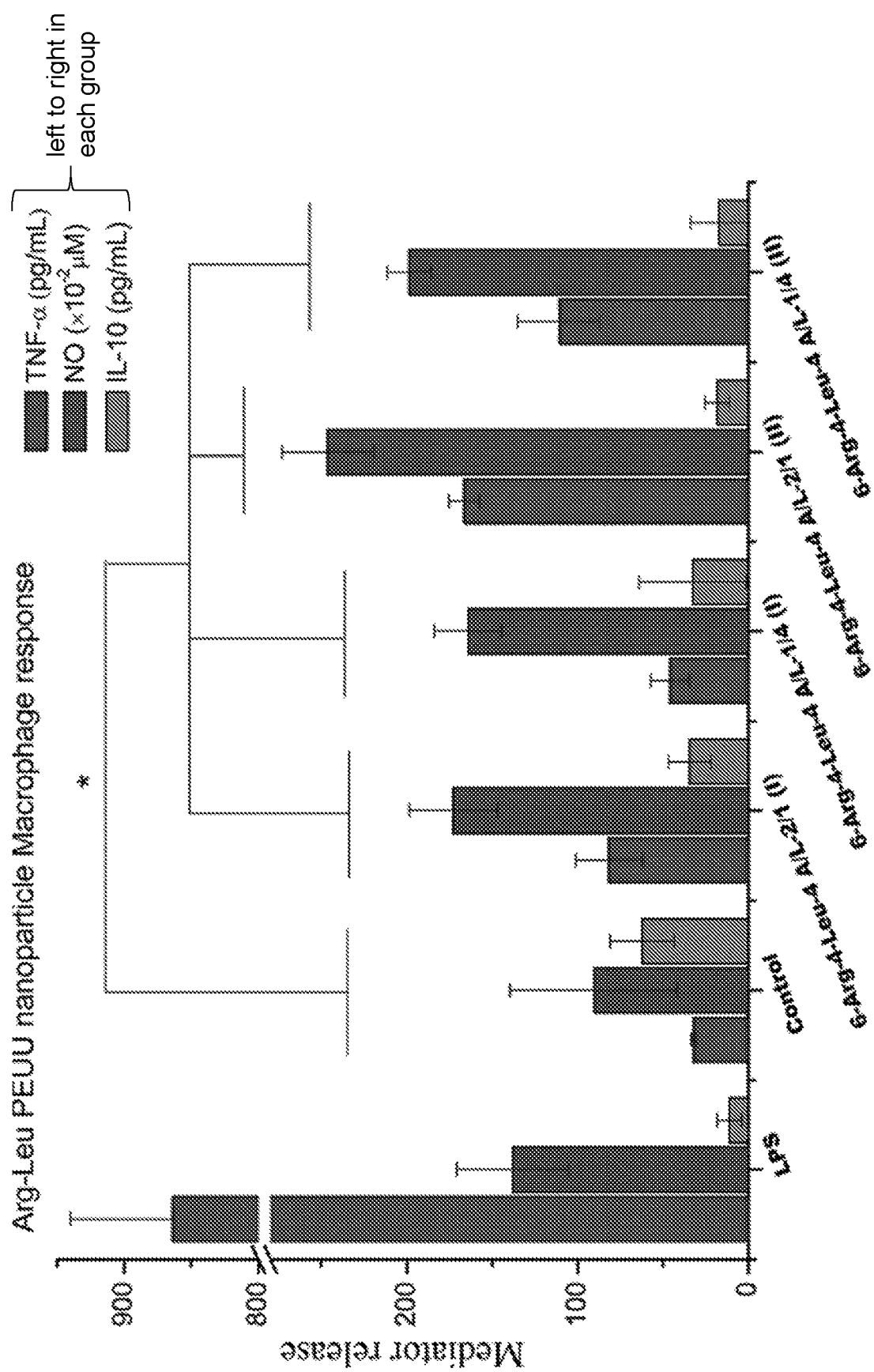
FIG. 18 shows TNF-α secretion, NO production and IL-10 secretion by RAW 264.7 macrophages ($1\times10^5$) after 24 h of incubation with 100 µL of blank Arg-Leu PEUU NPs. 6-Arg-4-Leu-4 A/L-2/1 (I): 1 mg/mL 6-Arg-4-Leu-4 A/L-2/1 NP; 6-Arg-4-Leu-4 A/L-2/1 (II): 2 mg/mL 6-Arg-4-Leu-4 A/L2/1 NP; 6-Arg-4-Leu-4 A/L-1/4 (I): 1 mg/mL 6-Arg-4-Leu-4 A/L-1/4 NP; 6-Arg-4-Leu-4 A/L-1/4 (II): 2 mg/mL 6-Arg-4-Leu-4 A/L-1/4 NP. * $p<0.05$ for NP groups versus control groups.

Inflammatory Response of Arg-Leu PEUU NPs. Macrophages of the mononuclear phagocyte system are able to engulf nanoparticle carriers, which may activate macrophages to induce a foreign-body inflammatory response. The foreign nanoparticles-induced inflammatory response by macrophages has an important influence on cancer cells in many aspects. In this study, the inflammatory response of RAW 264.7 macrophage cells after 24 h of incubation with 6-Arg-4-Leu-4 A/L-2/1 and 6-Arg-4-Leu-4 A/L-1/4 NPs at two concentrations (1 and 2 mg/mL) was investigated and is shown in FIG. 18 in terms of the production of TNF-α, NO and IL-10. Because Arg-containing PEUU materials are also biodegradable and Arg metabolism is tightly related to the macrophage activation types, the Arg-Leu PEUU NP carriers are expected to have a potential role in the interaction between macrophages and cancer cells.

FIG. 18 data show that RAW 264.7 macrophage cells treated with 6-Arg-4-Leu-4 A/L-2/1 and 6-Arg-4-Leu-4 A/L-1/4 NPs exhibited elevated and concentration-dependent TNF-α and NO production when compared to the blank control group, while the production of IL-10 from RAW 264.7 cells after treating with Arg-Leu PEUU NPs was slightly decreased. Most notably though, the two samples that stimulated the highest TNF-α production (demonstrating an inflammatory response) (100 µL 2 mg/mL 6-Arg-4-Leu-4 2/1 and 6-Arg-4-Leu-4 1/4) had the lowest IL-10 production, indicating that the Arg-Leu PEUU NPs triggered an M-1 type inflammatory macrophage stimulation. RAW 264.7 macrophage cells treated with Arg-Leu PEUU NPs with higher Arg contents (i.e., 6-Arg-4-Leu-4 2/1 NPs) produced more TNF-α and NO than the 6-Arg-4-Leu-4 2/1 NP treated case, particularly at the higher Arg-Leu PEUU NP concentration (II in FIG. 18).

The immune response to cancer is closely related to the inflammatory response of many immune cells, among which macrophages are the key players, particularly in the presence of foreign body-like drug carriers. Activated macrophages are the main source of the production of TNF-α, NO, and many other growth factors and cytokines. Macrophages and cancer cells have a complex relationship: macrophages affect many processes, ranging from tumor initiation to the acceleration of tumor progression and metastasis. Macrophages can be classically activated by IFN-γ/TNF, thereby consuming Arg to produce NO through the iNOS pathway (M-1 macrophage, destructive). Alternatively, macrophages can be activated by IL-4/IL-13, leading to the induction of arginase in these cells (M-2 macrophages, constructive), increasing the polyamine, ornithine, and proline production from Arg through the arginase pathway.

Tumor inhibition or growth is associated with local upregulation of the NO synthase or arginase pathway. Classically activated macrophages produce more TNF-α and NO, while IL-10 is a signature cytokine produced by alternatively activated macrophages. High dose local TNF-α can destroy tumor blood vessels, and even a systemic low dose of TNF-α can enhance the antitumor activity of liposomal delivered doxorubicin. NO generated from classically activated macrophages inhibits cell proliferation and has a cytotoxic effect on tumor cells.

The activation of macrophages by NP phagocytosis plays an important role in the tumoricidal activity. The activation of macrophages by Arg-rich biomaterials has been reported to lead to high TNF-α and NO production. Similarly, the current Arg-Leu PEUU NPs can classically activate macrophages, which may enhance their tumoricidal activity (FIG. 18). IL-10 and TGF-β play important roles in down-regulating macrophage inflammatory activation. IL-10 increases the total level of arginase in macrophages in many ways and may promote tumor growth. Arg-Leu PEUU NPs taken up by macrophages showed increased Arg metabolism through the iNOS pathway (as expressed by higher NO production) without the enhancement in the IL-10 production from macrophages. Hence there are synergistic effects between activated type M1 macrophages from the Arg-Leu PEUU NP carriers and the cytotoxicity of their loaded DOX drug, which may augment the tumorcidial effects of the DOX-loaded Arg-Leu PEUU nanocarrier system.

Figure 19:
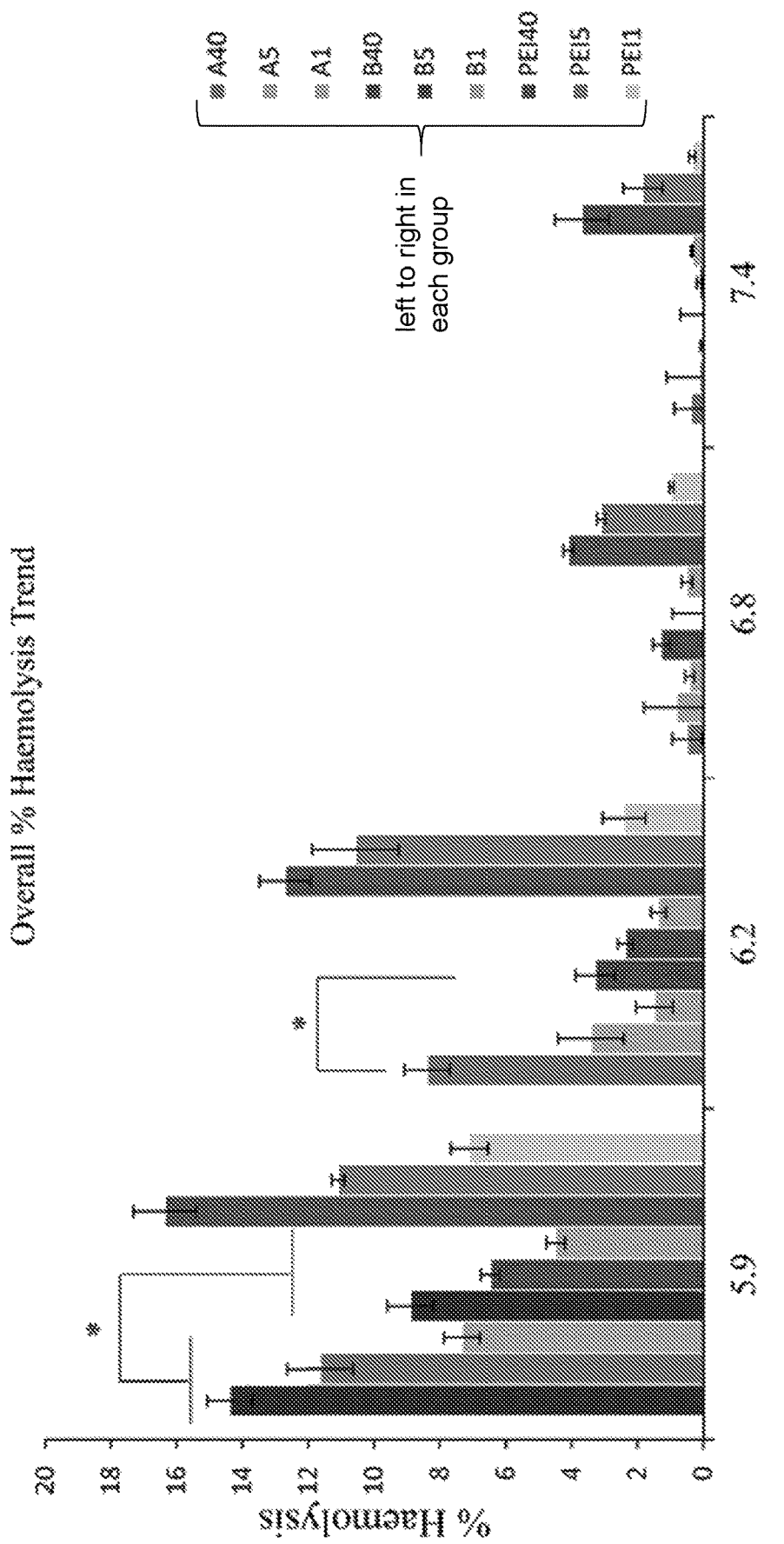
FIG. 19 shows hemolysis of bovine erythrocytes as a function of Arg-Leu PEUU NP concentration and pH (from 5.9 to 7.4). A group: 6-Arg-4-Leu-4 A/L-2/1 NP, A40:40 µg/mL; A5:5 µg/mL; A1:1 µg/mL. B group: 6-Arg-4-Leu-4 A/L-1/4 NP, B40:40 µg/mL; B5:5 µg/mL; B1:1 µg/mL; PEI group: PEI40:40 µg/mL; PEI5:5 µg/mL; PEI1:1 µg/mL. * $p<0.05$.

Hemolysis. For the hemolysis assay, bovine RBCs are considered a simple cellular model to study drug carrier-membrane interactions. The hemolytic activity of 6-Arg-4-Leu-4 A/L-2/1 and 6-Arg-4-Leu-4 A/L-1/4 PEUU NPs at pH values of 5.9, 6.2, 6.8, and 7.4 is shown in FIG. 19. Branched PEI ($pK_a$ of 10-11) at the same concentrations was also tested for comparison. In FIG. 19, both Arg-Leu PEUU NPs and PEI displayed pH and concentration-dependent hemolysis rates, e.g., higher hemolysis rates at an acidic pH. The concentration effect was most evident in an acidic pH. At 40 µg/mL, the Arg-Leu PEUU NPs with more Arg (i.e., 6-Arg-4-Leu-4 A/L-2/1) showed a more significant pH-dependent hemolysis rate than the Arg-Leu PEUU NPs with lower Arg contents (i.e., 6-Arg-4-Leu-4 A/L-1/4) in a more acidic pH environment. This Arg content effect is insignificant in a physiological pH (7.4) and near a neutral pH (6.8). The branched PEI showed consistently high pH and concentration effects over the whole range of pH values.

At the pH values closer to physiological conditions (pH values of 6.8 and 7.4), both 6-Arg-4-Leu-4 A/L-2/1 and 6-Arg-4-Leu-4 A/L-1/4 NPs showed little membrane disruptive effects (<1.5% hemolysis rate) over the whole concentration range studied, while the branched PEI showed a much higher hemolysis rate (3.7%-4.1%). At an acidic condition (pH of 5.9) as found in endosomes, 40 µg/mL 6-Arg-4-Leu-4 A/L-2/1 NPs showed a significantly higher hemolysis rate (14.4%) than the 6-Arg-4-Leu-4 A/L-1/4 NPs showed (8.9%), whereas the PEI at the same concentration had the highest hemolysis rate (16.4%). 6-Arg-4-Leu-4 A/L-2/1 with higher Arg contents demonstrated stronger membrane-disruptive activity than 6-Arg-4-Leu-4 A/L-1/4, probably due to their stronger cationic charge on the Arg-Leu PEUU NP surface (+40.9±1.46 mV of 6-Arg-4-Leu-4 A/L-2/1 vs +31.2±0.70 mV of 6-Arg-4-Leu-4 A/L-1/4) at all pH values.

Cationic polymers have been reported to enhance membrane lysis at low pH values via electrostatic interactions between protonated positively charged groups and negatively charged membranes. Cells usually take up drug carriers via endocytosis which confines the internalized carriers and their payloads to vesicles (such as endosomes). The payloads must be able to escape from the endosomes into the cytosol for them to perform their intended biological function. Early endosomes have a pH from 6.5 to 6.8, late endosomes have a lower pH of about 5.5, and the pH of lysosomes range from 4.6 to 5.0. Therefore, for an efficient intracellular delivery of therapeutic compounds, polymeric drug carriers have been designed to facilitate cargo release into the cytosol by destabilizing endosomal membranes under mildly acidic conditions. For example, a cationic lysine-based oligomer was reported to have pH-responsive hemolytic activity, and achieved a maximum membrane lytic activity in the late endosome. The major mechanism of the cationic NPs causing an endosomal membrane disruptive effect is known as the proton sponge effect (or pH buffering effect). The low pH in an endosomal environment leads to the protonation of the entrapped cationic carrier via ATPase proton pumps that cause a passive inflow of the counteranion $Cl^-$, leading to a higher ionic concentration gradient and water flow into the endosome. This results in osmotic swelling and eventual endosome rupture and release of its contents into the cytosol. Other cationic amino-acid-based drug carriers (e.g., histidine, lysine based) also display similar endosomal membrane disruption capability via their proton sponge effect. However, too much endosome disruption may also cause increased cytotoxicity like PEI. The current cationic Arg-Leu PEUU NPs appear to achieve a better balance between a relatively mild endosomal membrane disruptive capability and good cellular biocompatibility, and hence they have the potential to be a new family for biodegradable nanodrug delivery.

Figure 20:
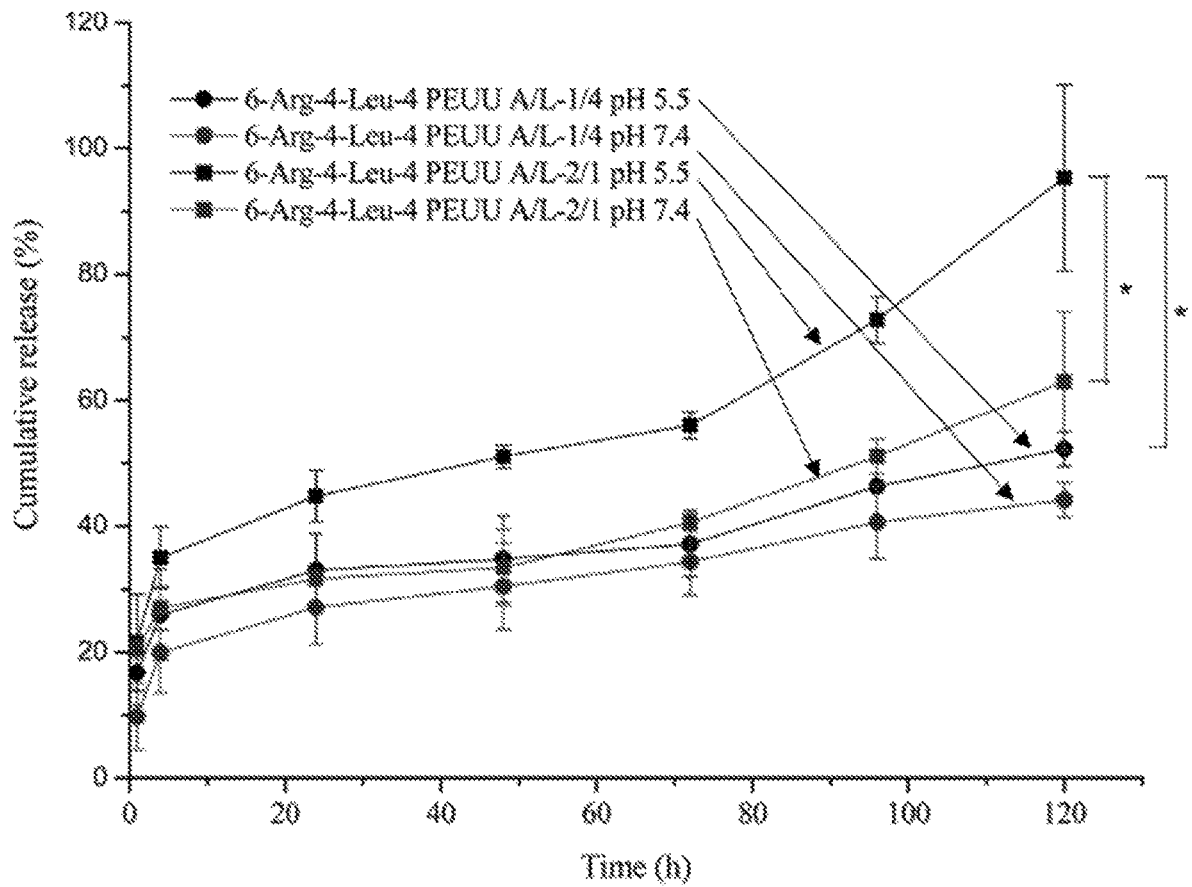
FIG. 20 shows cumulative release of doxorubicin (DOX) (initial loading content 20%) from 6-Arg-4-Leu-4 1/4 and 6-Arg-4-Leu-4 2/1 NP carriers at pH values of 5.5 and 7.4, in a PBS buffer of ionic strength 0.1 M, and at 37° C. * $p<0.05$.

In Vitro Release of DOX from the Arg-Leu PEUU NPs. The in vitro release of DOX from 6-Arg-4-Leu-4 A/L-2/1 and 6-Arg-4-Leu-4 A/L-1/4 NPs with a 20 wt % DOX initial loading was examined at pH values of 5.5 and 7.4 and at 37° C. The DOX release data in FIG. 20 show that both Arg-Leu PEUU NPs exhibited faster DOX release profiles at endolysosomal pH (5.5) than at a physiological pH (7.4). For example, 72.8% of DOX was released from the 6-Arg-4-Leu-4 2/1 NPs within 96 h at pH 5.5 versus 51.0% from the same drug carrier at a pH of 7.4. Similar pH effects were also observed from the 6-Arg-4-Leu-4 1/4 but at a smaller magnitude, i.e., 46.3% in pH 5.5 vs 40.6% in pH 7.4. The 6-Arg-4-Leu-4 1/4 NPs showed a slower DOX release than the release from 6-Arg-4-Leu-4 2/1 NPs, and can be attributed to a stronger hydrophobic interaction between the hydrophobic DOX and the more hydrophobic types of Arg-Leu PEUU NP carriers like 6-Arg-4-Leu-4-1/4 NPs.

The accelerated DOX release from the Arg-Leu PEUU NPs in an acidic environment was attributed to the ionization of DOX, which increased its solubility and ionization of the Arg moiety of the self-assembled polymeric Arg-Leu PEUU NPs. In this study, the observed faster DOX release in a more acidic medium is consistent with other reported studies of cationic DOX carriers, such as Poly(HPMA-co-APMA). Compared to many recently reported DOX nano-sized carriers, the Arg-Leu PEUU NPs showed slightly more sustained DOX release profiles with a lower burst release in vitro (<22%) in the first hour. The relative stability of the Arg-Leu PEUU NPs at a pH of 7.4 and their accelerated DOX release in an acidic environment could be advantageous in reducing the premature release of DOX extracellularly. After DOX was delivered into the cancerous cells, the Arg-Leu PEUU NPs showed faster DOX release, which was triggered by a more acidic pH due to higher hemolysis rates (FIG. 19).

Figure 21:
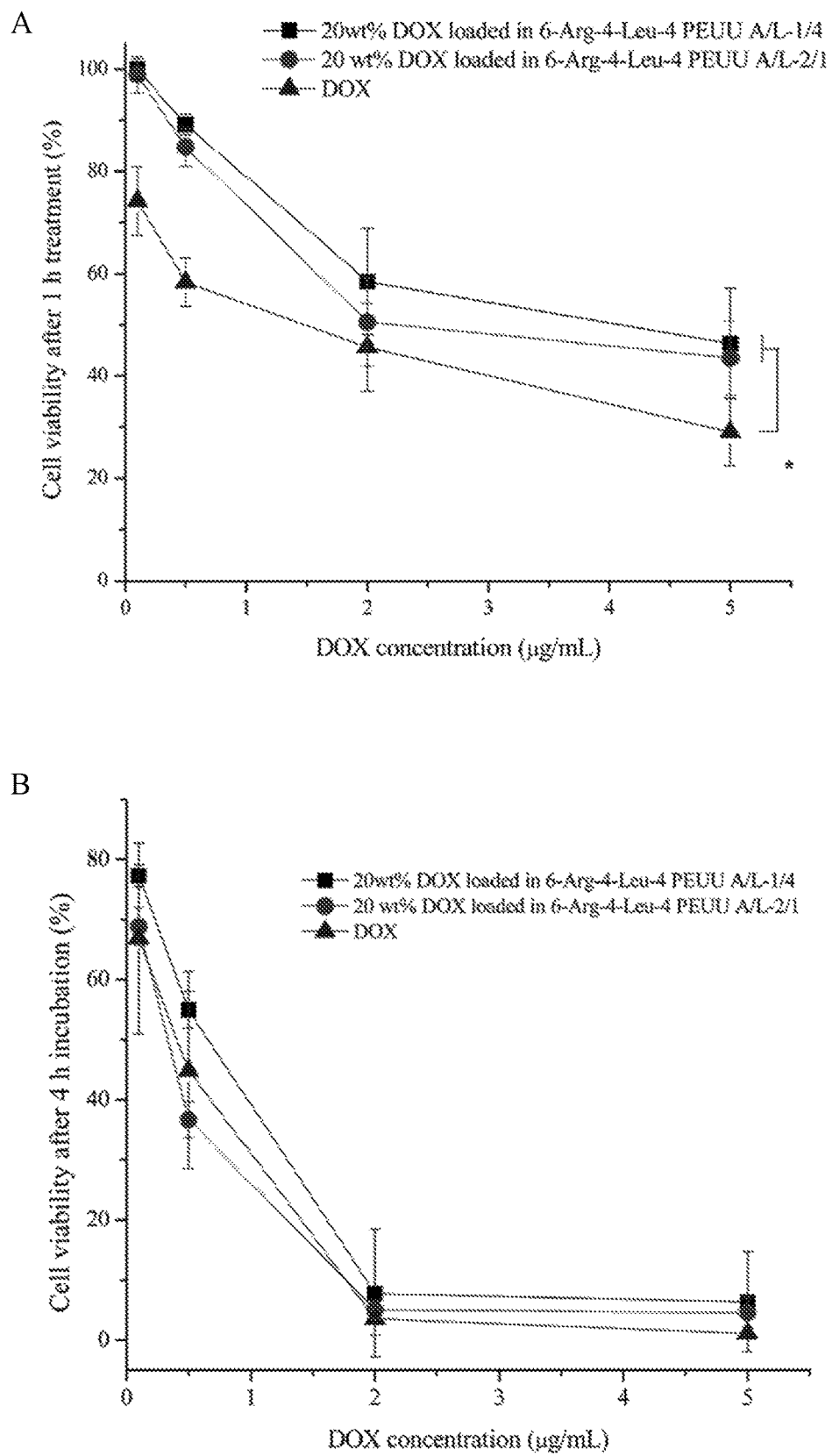
FIG. 21 shows time-dependent cytotoxic effects of 20 wt % initially loaded DOX in 2 types of Arg-Leu PEUU NPs and free DOX against HeLa cells. (A) 1 h treatment; (B) 4 h treatment; (C) 24 h treatment. * $p<0.05$.
Figure 21:
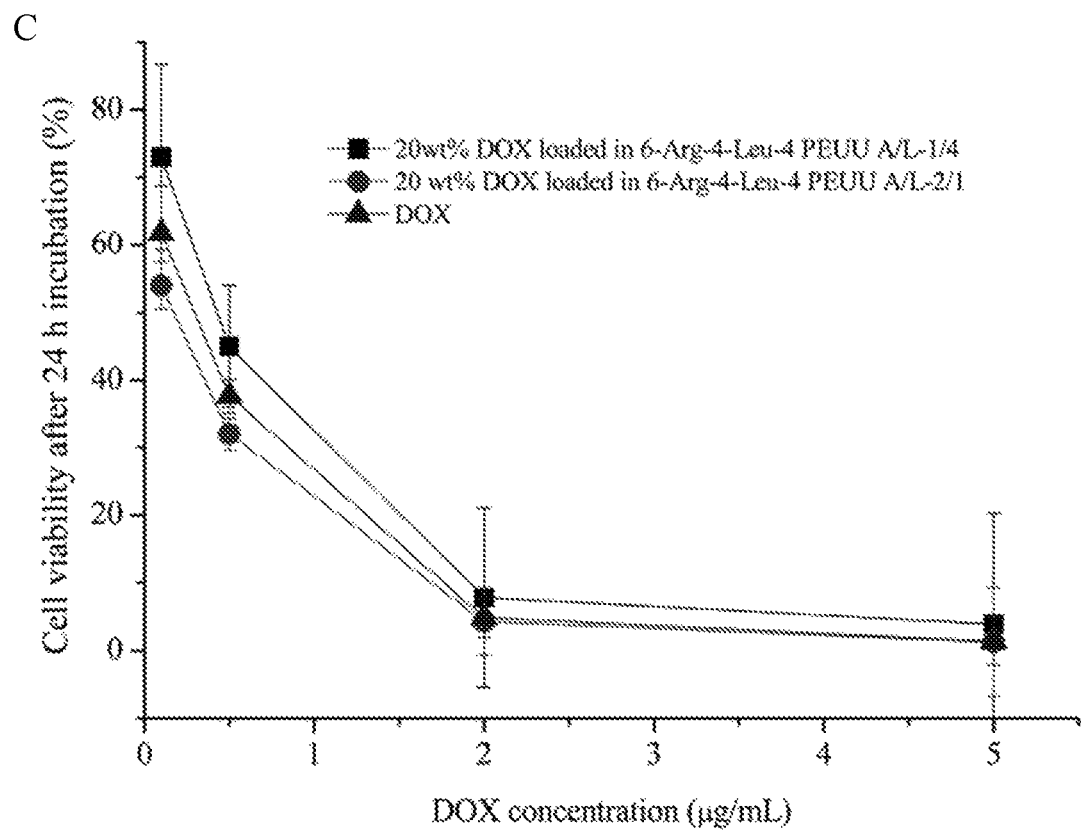
Figure 22:
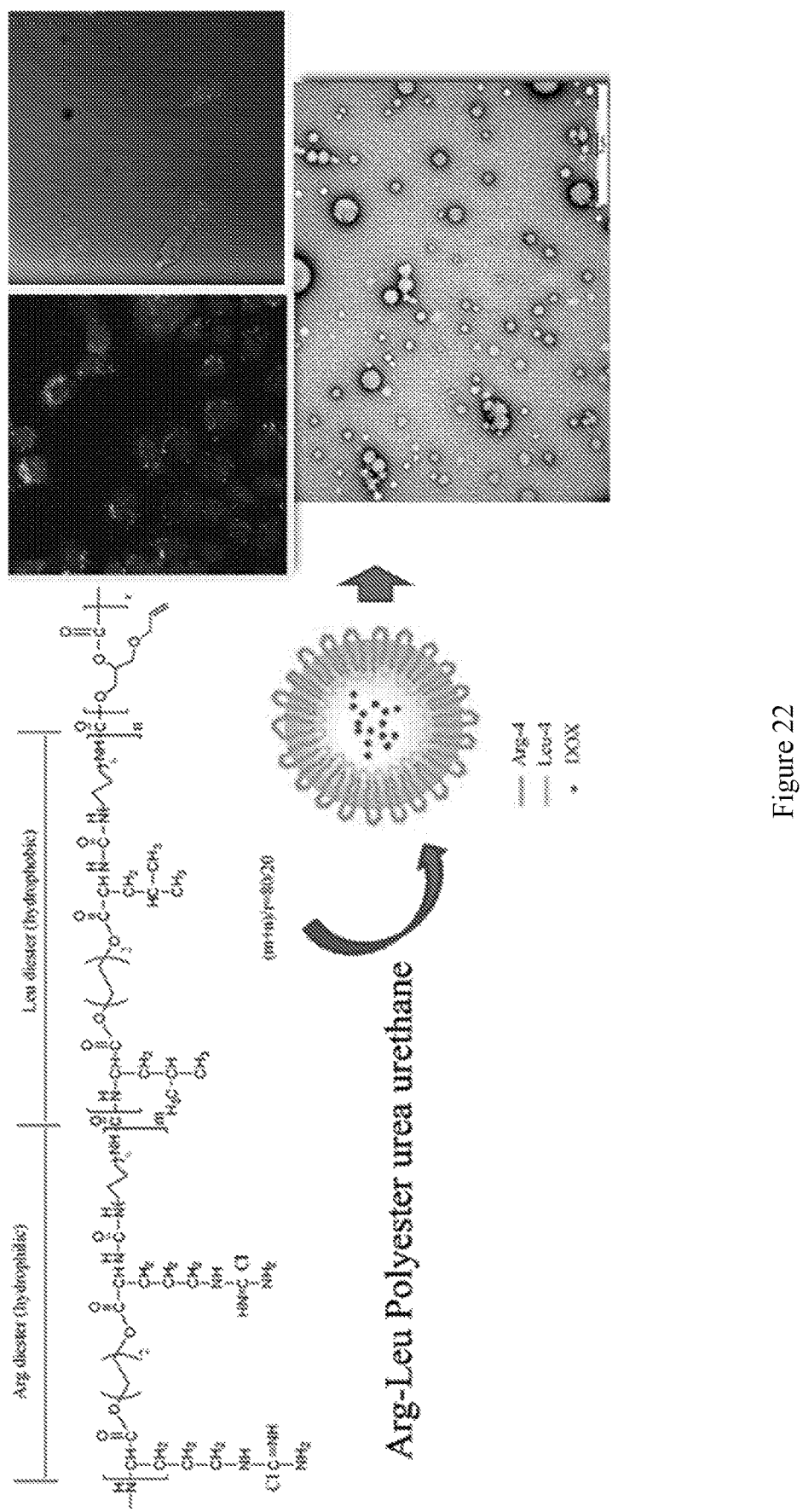
FIG. 22 shows a schematic of an Arg-Leu PEUU, a NP assembled from Arg-Leu PEUU loaded with DOX, confocal laser scanning microscopy images of the same after being loaded with DOX and being taken up by HeLa cells, and a TEM micrograph of the DOX-loaded Arg-Leu PEUU.

In Vitro Cytotoxicity of DOX-Loaded Arg-Leu PEUU NPs. HeLa cell efficacy with DOX-loaded 6-Arg-4-Leu-4 A/L-1/4 and 6-Arg-4-Leu-4 A/L-2/1 NPs is shown in FIG. 21. The data illustrate that free DOX has the highest cytotoxic potency at the shortest duration of treatment (i.e., 1 h, FIG. 21A), but the DOX-loaded Arg-Leu PEUU NPs achieved the same potency as the free DOX at a longer duration of treatment (4 and 24 h, FIG. 21B,C). The $IC_{50}$ of free DOX is about 0.4 to 0.5 µg/mL, whereas the $IC_{50}$ of the DOX-loaded 6-Arg-4-Leu-4 A/L-2/1 NPs was lower than 0.4 µg/mL, and therefore more potent. In addition, the Arg-Leu PEUU NPs with higher Arg contents (i.e., 6-Arg-4-Leu-4 A/L-2/1) always exhibited higher cytotoxicity than the Arg-Leu PEUU NPs with lower Arg contents (such as 6-Arg-4-Leu-4 A/L-1/4) over all treatment durations. From the in vitro DOX release profiles (FIG. 20), more DOX was released from 6-Arg-4-Leu-4 A/L-2/1 NPs which have relatively better hydrophilicity (Table 6) and smaller average size (Table 7) when compared to the 6-Arg-4-Leu-4 A/L-1/4 NPs in an aqueous medium. Consequently, 6-Arg-4-Leu-4 A/L-2/1 NPs (with more Arg content) showed higher toxicity toward the HeLa cells. Also, the 6-Arg-4-Leu-4 A/L-2/1 NPs have a higher capacity to disturb the endosomal membrane after internalization (FIG. 19), which could be another contributing factor leading to higher potency than the DOX-loaded 6-Arg-4-Leu-4 A/L-1/4 NPs.

A slower drug cytotoxicity effect observed in the Arg-Leu PEUU NPs at 1 hr incubation period can be attributed to two factors: (1) cellular uptake of any NPs can take several hours to internalize and hence would lead to a prolonged treatment time for exhibiting the cytotoxic DOX effect, and (2) DOX would not be instantly released from the Arg-Leu PEUU NP carriers into cytosol as free DOX would allow. At the 4 and 24 h treatment durations, the DOX-loaded 6-Arg-4-Leu-4 A/L-2/1 NPs showed higher cytotoxicity than the free DOX, possibly because the DOX-loaded cationic 6-Arg-4-Leu-4 A/L-2/1 NPs were taken up by the HeLa cells, resulting in a higher intracellular DOX-loaded NP concentration. The higher cytotoxicity of the DOX-loaded Arg-Leu PEUU NPs compared to free DOX at the 4 and 24 h treatment is consistent with the uptake data from either free DOX or DOX-loaded Arg-Leu PEUU NPs by HeLa cells, as measured by live cell density (FIG. 17B vs 17C) and mean DOX fluorescence signal intensity (FIG. 17D). The DOX-loaded Arg-Leu PEUU NPs induced a slightly slower rate of cancer cell cytotoxicity, which agreed well with the in vitro drug release and endosomal escape mechanism. This slightly delayed cytotoxicity of the DOX-load Arg-Leu PEUU NPs may also be used to control the instant toxicity of free DOX toward healthy cells before the carrier particles enter targeted cancer cells. When comparing the 6-Arg-4-Leu-4 A/L-2/1 NPs to the equivalent amount of loaded DOX in the 6-Arg-4-Leu-4 A/L-1/4 NPs, the latter showed a decreased cytotoxicity and required a longer treatment time to fully exert the DOX efficacy. These effects are possibly due to their higher hydrophobicity (from higher Leu contents in the Arg-Leu PEUU NPs), allowing for these particles to retain DOX for a longer time through a hydrophobic interaction. This reduced cytotoxicity toward HeLa cells via a hydrophobic interaction is consistent with the slower in vitro DOX release rate of the more hydrophobic Arg-4-Leu-4 A/L-1/4 NPs shown in FIG. 20. This feature could also be utilized as another parameter to achieve a desired controlled drug efficacy. In fact, for in vivo applications, free DOX intravenous administration at a high concentration is not optimal due to its instant toxicity to healthy tissue. The DOX-loaded Arg-Leu PEUU NPs could achieve a slow and controllable extracellular release to minimize cytotoxicity to normal tissue, followed by a faster release triggered by an intracellular acidic condition. If carried out, this passive accumulation at tumor tissue via enhanced permeability and the retention effect could make this new polymeric biomaterial family a viable therapeutic anticancer drug delivery vehicle.

In this example, a new family of cationic Arg-Leu PEUU biomaterials and their self-assembled nanoparticles (NPs) were developed as an advanced nanocarrier for doxorubicin. The chemical, physical, and biological properties of Arg-Leu PEUU can be tuned by controlling the feed ratio of the 4 building blocks (amino acids, diols, glycerol α-monoallyl ether, and 1,6 hexamethylene diisocyanate), particularly the feed ratio of hydrophilic Arg to hydrophobic Leu amino-acid-based monomers. This new family of Arg-Leu PEUU copolymers has a $M_w$ from 13.4 to 16.8 kDa, a glass-transition temperature from −3.4 to −4.6° C., and dissolves in common organic solvents such as ethanol, methanol, DMSO, and DMF. Arg-Leu PEUUs are biocompatible with 3T3 cells and promote the viability and adhesion of BAECs. The Arg-Leu PEUU biomaterials showed high macrophage-induced inflammatory cytokine production of TNF-α and NO but low IL-10, indicating a leaning toward the M-1 macrophage inflammatory response. An M-1 macrophage inflammatory response of the newly developed Arg-Leu PEUU biomaterials as nanodrug carriers could provide a synergistic cytotoxicity effect toward cancer cells from both the loaded anticancer drug toxicity and the enhanced macrophage tumoricidal activity from the nanocarrier material. Arg-Leu PEUU NPs, prepared by a relatively simple dialysis method, have diameters ranging from 187 to 272 nm, and due to their cationic feature, the Arg-Leu PEUU NPs were easily taken up by HeLa cells within 4 h, and showed a pH-responsive release of DOX in vitro. The in vitro hemolysis assay data of the Arg-Leu PEUU NPs showed an endosomal escape potential after cellular uptake. By adjusting the chemical composition of the Arg to Leu feed ratio in the Arg-Leu PEUU NP system, the DOX release profile could be altered, thereby producing either an enhanced or reduced DOX cytotoxicity on the cancer cells. Coupled with the capability of having pendant functional groups built into Arg-Leu PEUU biomaterials for the potential attachment of target molecules for enhanced efficacy, this new family of Arg-Leu PEUU biomaterials and its NPs could add a new dimension to enhanced nanocarrier-based delivery systems. This new biomaterial family may allow for a larger variety of chemotherapeutic drugs and a better nanobased therapeutic efficacy.

Example 3

This example provides a description of the use of nanoparticles of the present disclosure.

Nanoparticle-Drug Nanoparticles used in the animal trial. Gambogic acid (GA), a Chinese medicine, loaded branched FA-PEG3400-6-Arg-2 PEUU NP (~11 wt % drug).

In vivo xenograft Protocols Used. Female BALB/c nude mice, 8-weeks old, were obtained from the Laboratory Animal Services Centre, The Chinese University of Hong Kong. Mice were kept at room temperature 23±2° C. with an alternating 12-h light-dark cycle, and were allowed access to food and water ad libitum. All of the experimental protocols were carried out with the approval of the Committee on Use of Human and Animal Subjects in Teaching and Research of Hong Kong Baptist University and according to the Regulations of the Department of Health, Hong Kong SAR, China.

Before inoculation, 10 mg/kg Estradiol benzoate was given into mice through intraperitoneal (IP) injection with 2-day intervals. MCF-7 cells ($4 \times 10^6$ cells per mouse) were suspended in PBS and inoculated subcutaneously into the left flank of each mouse, and tumor growth was monitored regularly. Once tumors were palpable (~100 mm³), mice were randomly divided into three groups (n=5 for each group) to receive intravenous injection of normal saline (Saline group), gambogic acid (Free-GA) solution (8 mg GA/kg), GA loaded FA-Arg PEUU NP suspension (8 mg/kg GA in 50 mg/kg FA-Arg PEUU NP carrier, linear and branched Arg PEUU). Equal volumes of saline were used as solvent for the free drug groups.

The therapy was continued six times at 2-day intervals through tail vein injection. Estradiol benzoate was also IP injected into mice at 2-day intervals during administration. The antitumor activity of the tested formulations was estimated by recording the changes in tumor mass. Tumor volumes were monitored by recording the tumor length and width with a caliper then calculated using the equation, $V=0.5 \times a \times b^2$, where V is tumor volume (mm), a is tumor length (mm), and b is tumor width (mm). Mice were sacrificed on the 12th day after administration, and the tumors were weighed. Furthermore, in vivo tumor cell apoptosis was investigated using the terminal deoxynucleotidyl transferase dUTP nick end labeling (TUNEL) assay and hematoxylin and eosin staining assay. TUNEL staining was conducted according to the manufacturer's recommendations, and nuclear staining was performed using 4',6-diamino-2-phenylindole mounting medium.

Figure 26:
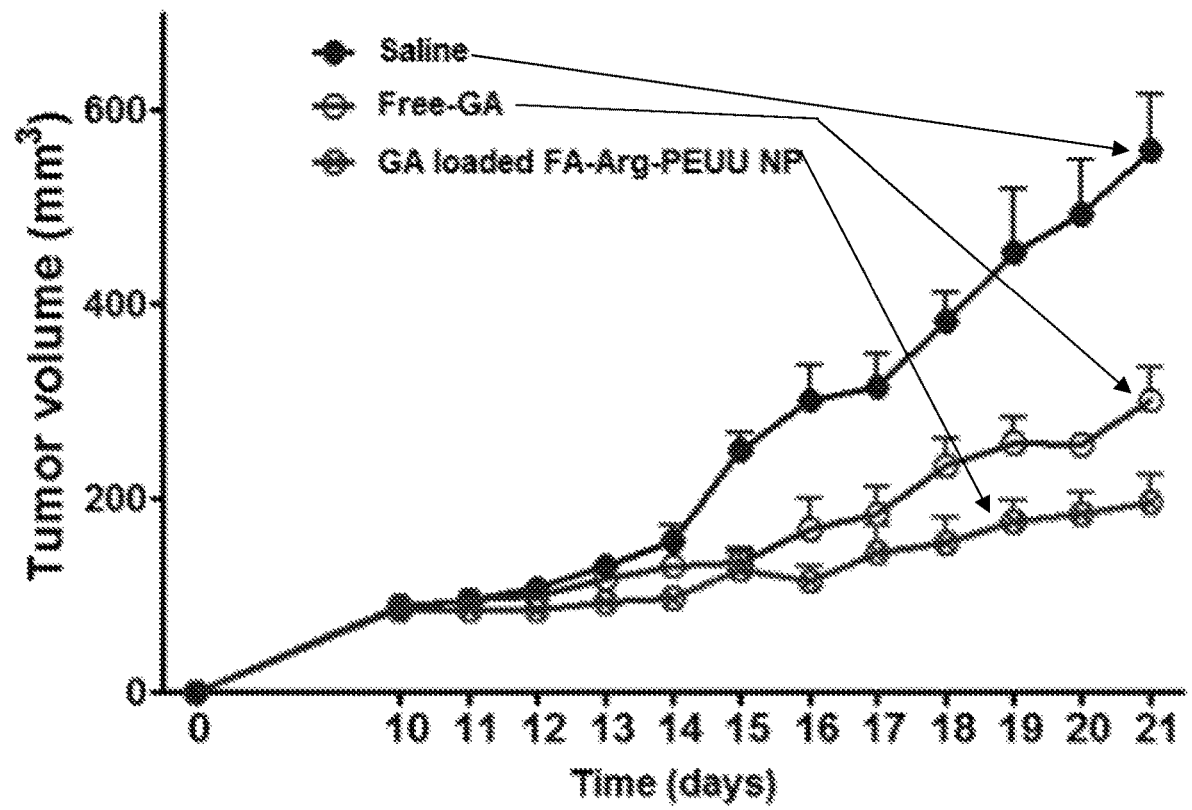
FIG. 26 shows 8-week old female nude mice were engrafted with MCF-7 cells and randomly divided into 3 groups: Saline group, Free-GA group, GA loaded FA-Arg PEUU NP group (n=5). Tumor volumes were measured and calculated by the length and width every day.
Figure 27:
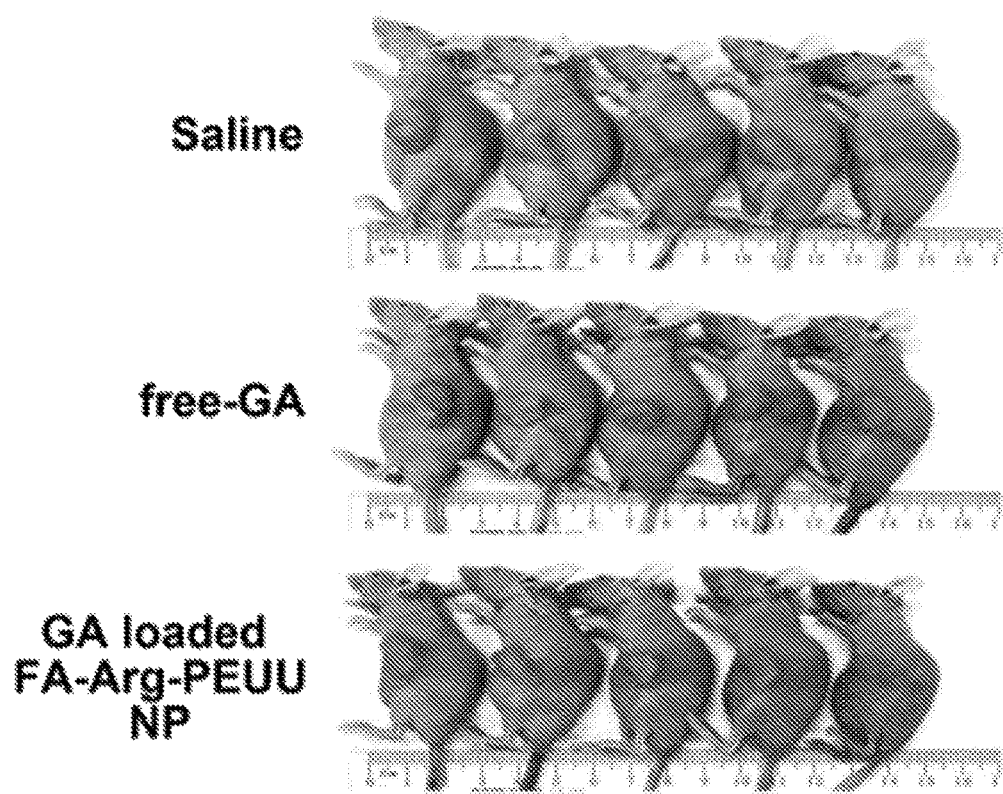
FIG. 27 shows photo images of all treated mice at the end of 21 days.

Animal Trial Data. The nude mice were injected with human breast cancer cells (MCF-7) and then treated by the GA-loaded FA-Arg PEUU NP with both the free-GA (no NP carrier) and saline treatments as the controls for comparison. As shown in FIGS. 26 and 27, the tumor volumes and masses were increased dramatically in the control group treated with Saline. In mice exposed to the GA-loaded FA-Arg PEUU NP, the tumor volumes and masses were significantly smaller than those in mice injected with free-GA.

As shown in FIG. 26, 8-week old female nude mice were engrafted with MCF-7 cells and randomly divided into 3 groups: Saline group, Free-GA group, GA loaded FA-Arg PEUU NP group (n=5). Tumor volumes were measured and calculated by the length and width every day.

FIG. 27 shows the actual images of the MCF-7 human breast cancer cell infected actual mice that were treated by the GA loaded FA-Arg PEUU NP testing group with saline and free GA treatments as the controls.

Figure 28:
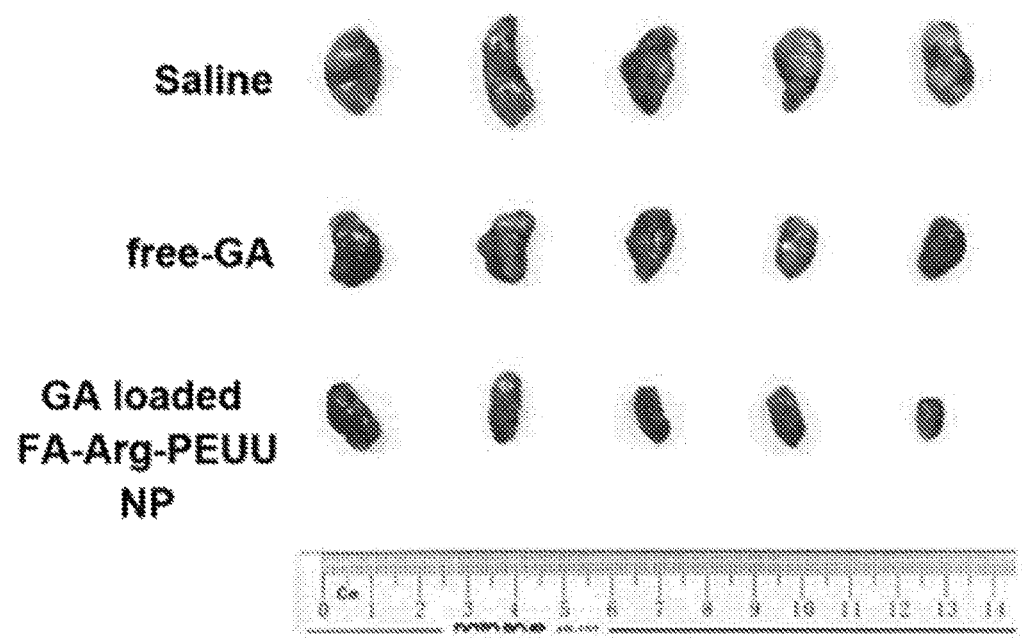
FIG. 28 shows photo images of the dissected xenograft tumors from mice at the end of 21 days study period.

The dissected xenograft tumors were and measured and the images of the dissected tumors are shown in FIG. 28.

Figure 29:
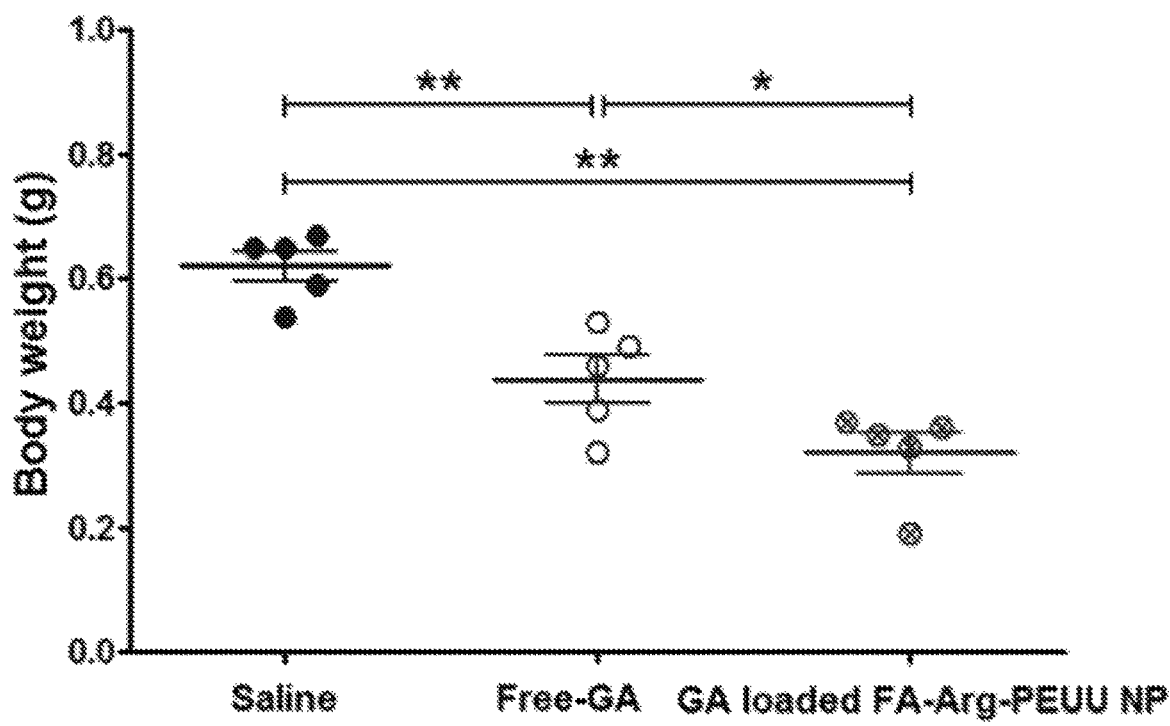
FIG. 29 shows tumor weight of 3 groups of mice was measured after mice were scarified. *P<0.05,**P<0.01.

Although the GA loaded FA-Arg PEUU NP had a higher suppression on tumor growth, the body weight of mice (FIG. 29) was unaffected as compared with free-GA group, in which body weight was declined with the extended treatment. The average body weight of the 3 groups are: 0.62 gram for the saline control, 0.44 gram for the free GA control, and 0.32 gram for the GA-loaded FA-Arg PEUU NP. These body weight data coupled with the tumor size and volume data in FIGS. 26-28 suggest that the GA-loaded FA-Arg PEUU NP treatment group had the smallest side effect of the GA drug, i.e., achieving the highest potential toward MCF-7 breast tumor at the lowest drug side effect.

Figure 30:
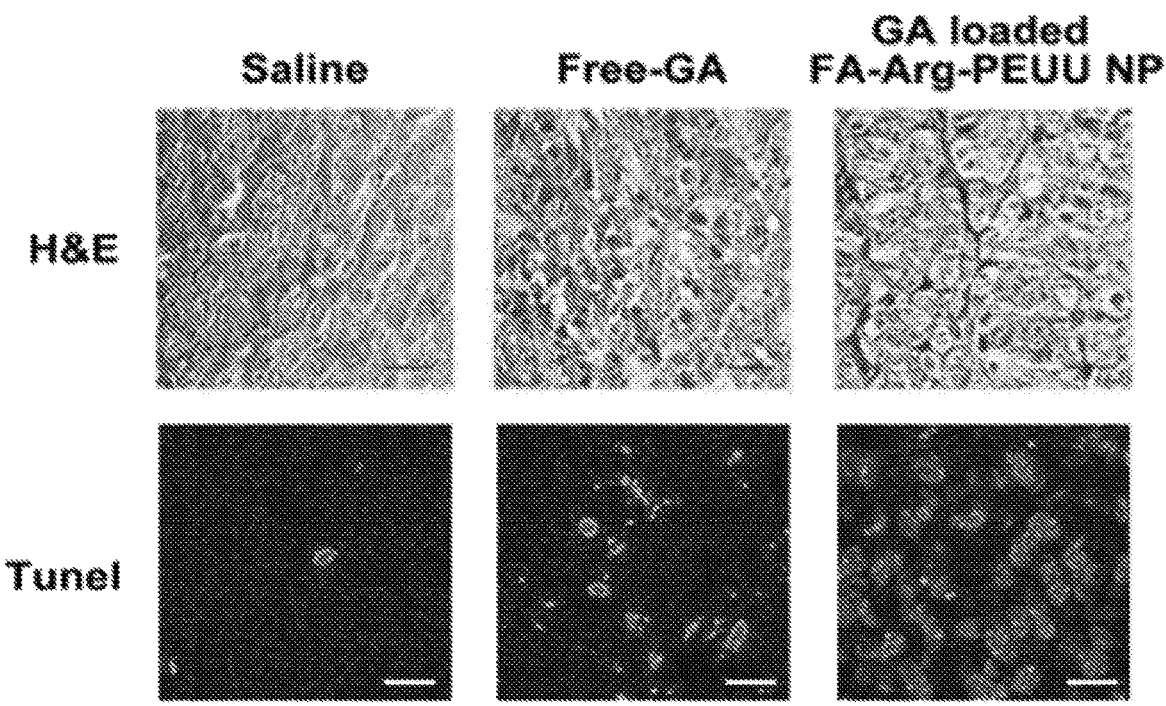
FIG. 30 shows H&E staining and Tunel staining for xenograft tumor in 3 groups. Scale bar=50 μm.
Figure 31:
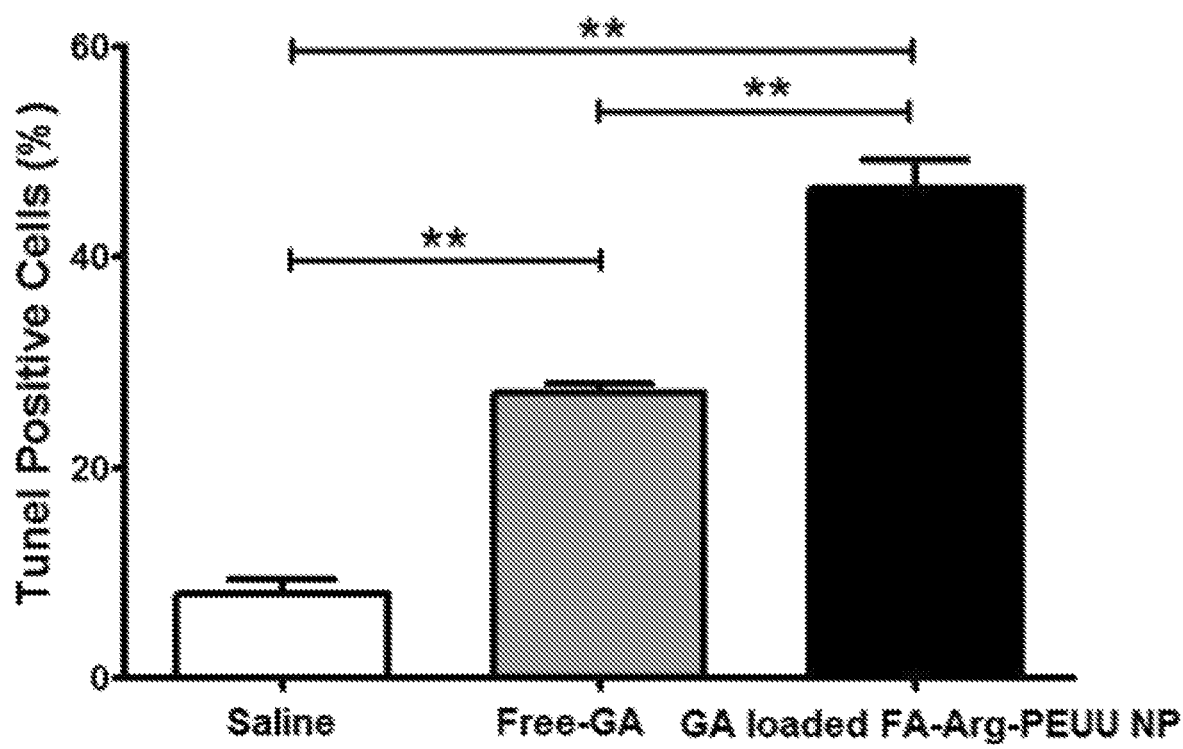
FIG. 31 shows quantitative data extracted from the staining in FIG. 30 Tunel staining images.

The results of H&E staining (FIG. 30) showed much more vacuoles in the tumor tissue from the GA-loaded FA-Arg PEUU NP group, but fewer vacuoles were found in mice treated with free-GA, suggesting the potential of the GA-loaded FA-Arg PEUU NP treatment toward MCF-7 human breast cancer tissue. In addition, the image data of the Tunel staining for examining the mechanism of cancer cell death (FIGS. 30 and 31) suggest that the GA-loaded FA-Arg PEUU NP treatment induced far more significant apoptosis in tumors than free-GA, as showed by the stronger red fluorescence labeled anti-Brdu antibody. FIG. 31 data are the quantitative expression of the Tunel staining image data.

Although the present disclosure has been described with respect to one or more particular embodiments and/or examples, it will be understood that other embodiments and/or examples of the present disclosure may be made without departing from the scope of the present disclosure.

The invention claimed is:

1. A polymer comprising:
   three or four polymeric groups, each polymeric group comprising:
   a poly(ester urea) segment comprising one or more ester urea repeat unit with two pendant alkyl guanidinium groups;
   a poly(urethane) segment comprising one or more urethane repeat unit with a pendant cross-linkable group;
   a poly(ethylene glycol) segment comprising one or more ethylene glycol units;
   a folate group; and
   a branching moiety,
   wherein in each polymeric group
   the poly(ester urea) segment is covalently bonded to the poly(urethane) segment,
   the poly(urethane) segment is covalently bonded to the poly(ethylene glycol) segment, the folate group is covalently bonded a terminus of the poly(ethylene glycol) segment, and wherein each polymeric group is covalently bonded to the branching moiety.

2. The polymer of claim 1, wherein the poly(ester urea) segment has the following structure:

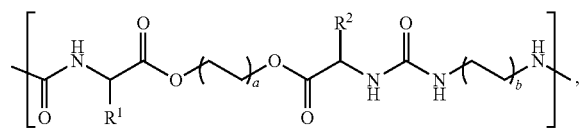

wherein
$R^1$ is independently, at each occurrence in the polymer, a hydrophilic group;
$R^2$ is, independently, at each occurrence in the polymer, a hydrophilic group;
a is independently, at each occurrence in the polymer, 1, 2, or 3; and
b is 2 or 3.

3. The polymer of claim 1, wherein the poly(urethane) segment has the following structure:

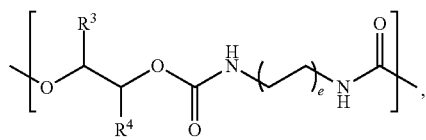

wherein
$R^3$ and $R^4$ are independently, at each occurrence in the polymer, a side-chain comprising a cross-linkable group or hydrogen; and e is independently, at each occurrence in the polymer, 2 or 3.

4. The polymer of claim 1, wherein the poly(ester urea) segment has a molecular weight of 200 to 23,000 g/mol or the poly(urethane) segment has a molecular weight of 0 to 2,500 g/mol or the poly(ethylene glycol) segment has a molecular weight of 1,000 to 5,000 g/mol.

5. The polymer of claim 1, wherein the branching moiety has the following structure:

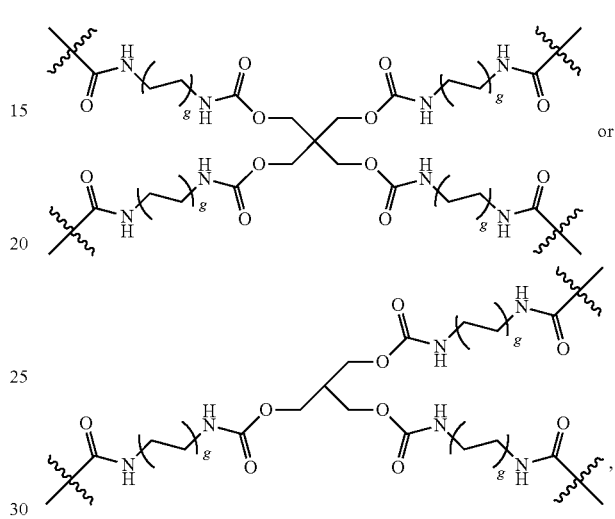

wherein,
g is independently, at each occurrence in the polymer, 2 or 3.

6. The polymer of claim 1, wherein the polymer has the following structure:

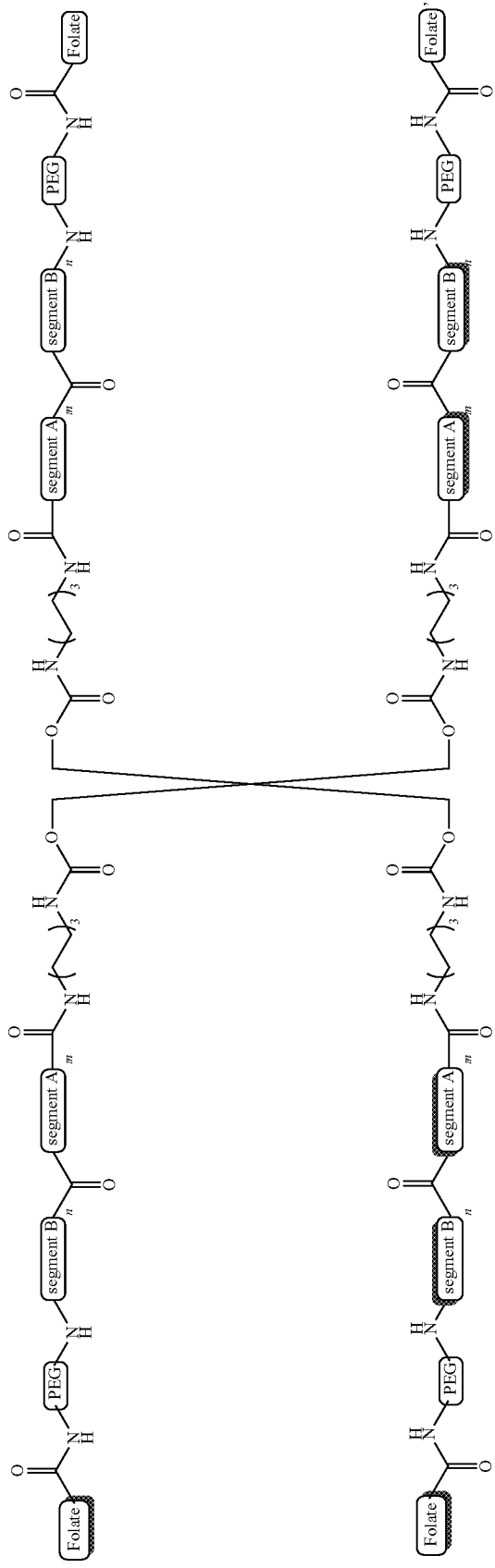

wherein
segment A is

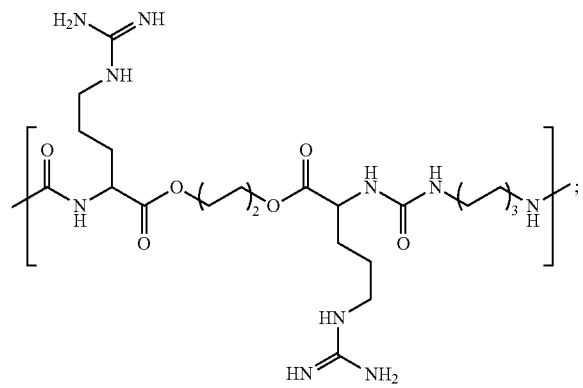

segment B is

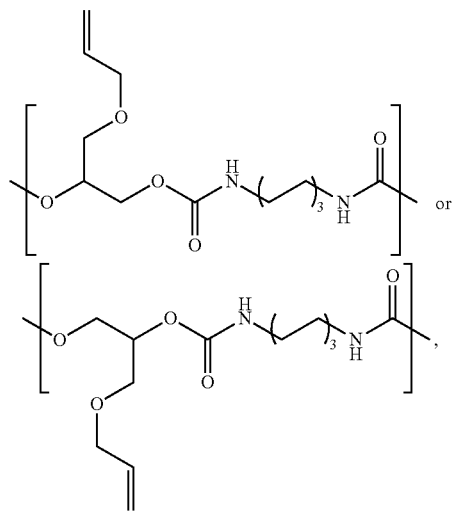

PEG is a poly(ethylene glycol) segment having a molecular weight of 1,000 to 5,000 g/mol;
folate is

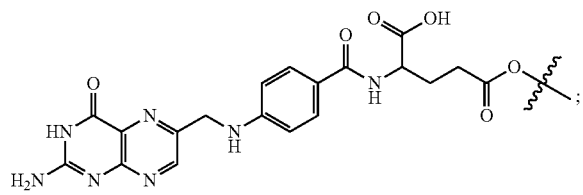 [SMILES: *OC(=O)CCC(NC(=O)c1ccc(NCc2cnc3nc(N)[nH]c(=O)c3n2)cc1)C(=O)O]

m is 1 to 30; and
n is 0 to 6.

7. A polymer comprising:
a hydrophilic poly(ester urea) segment comprising one or more ester urea repeat unit having two pendant alkyl guanidinium groups;
a poly(urethane) segment comprising one or more urethane repeat unit having a pendant cross-linkable group, wherein the poly(urethane) segment has the following structure:

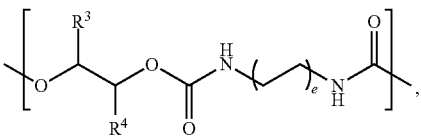

wherein
$R^3$ and $R^4$ are independently, at each occurrence in the polymer, a side-chain comprising a cross-linkable group or hydrogen, with the proviso that a plurality of $R^3$ or $R^4$ are a crosslinkable group; and
e is independently, at each occurrence in the polymer, 2 or 3, wherein the poly(ester urea) segment covalently bound to the poly(urethane) segment;
a first poly(ethylene glycol) segment and a second poly(ethylene glycol) segment, each segment comprising one or more ethylene glycol units; and
a first folate group and a second folate group,
wherein the first poly(ethylene glycol) segment is covalently bound to the poly(urethane) segment and the second poly(ethylene glycol) segment is covalently bound to the hydrophilic poly(ester urea) segment, and the first folate group is segment is covalently bonded to a terminus of the hydrophilic poly(ester urea) segment and the second folate group segment is covalently bonded to a terminus of the poly(urethane) segment.

8. The polymer of claim 7, wherein the poly(ester urea) segment has the following structure:

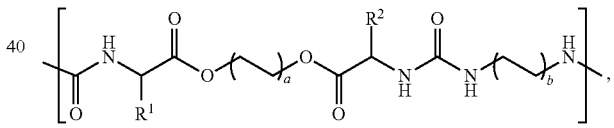

wherein
each $R^1$ and each $R^2$ is a side chain of an arginine residue;
a is independently, at each occurrence in the polymer, 1, 2, or 3; and
b is independently, at each occurrence in the polymer, 2 or 3.

9. The polymer of claim 7, wherein the poly(ester urea) segment has a molecular weight of 200 to 75,000 g/mol or the poly(urethane) segment has a molecular weight of 0 to 7,500 g/mol or the poly(ethylene glycol) segment has a molecular weight of 1,000 to 5,000 g/mol.

10. The polymer of claim 7, wherein the poly(ester urea) segment is 80 to 100% of the total moles of poly(ester urea) segment and poly(urethane) segment and/or the poly(urethane) segment is 0 to 20% of the total moles of poly(ester urea) segment and poly(urethane) segment.

11. The polymer of claim 7, wherein the polymer has the following structure:

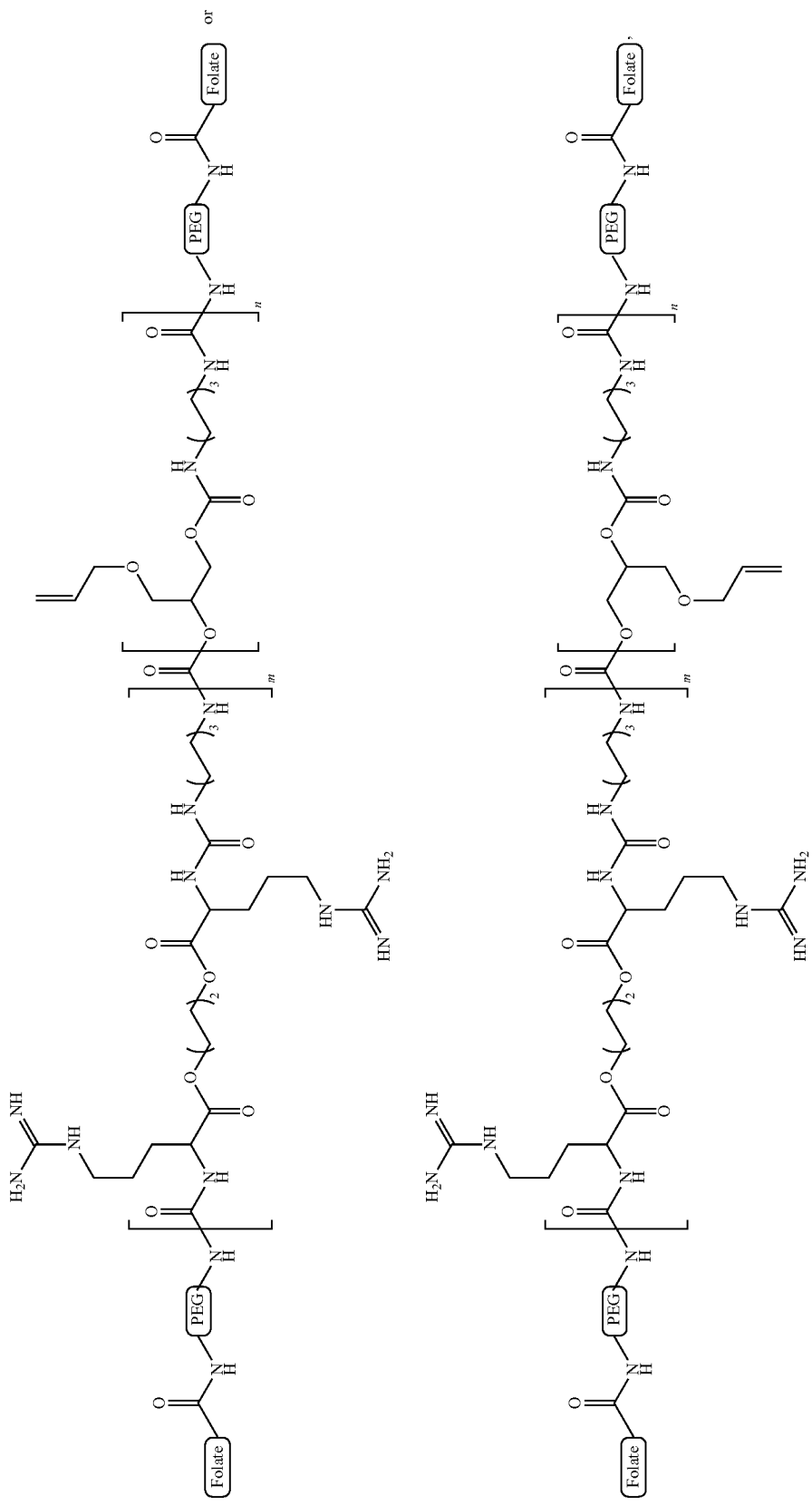

wherein
PEG is a poly(ethylene glycol) segment having a molecular weight of 1,000 to 5,000 g/mol;
folate is

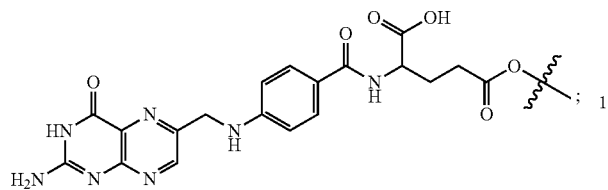

m is 1 to 70; and
n is 0 to 14.

12. A polymer comprising:
one or more hydrophilic poly(ester urea) segment, wherein the hydrophilic poly(ester urea) segment comprises the following structure:

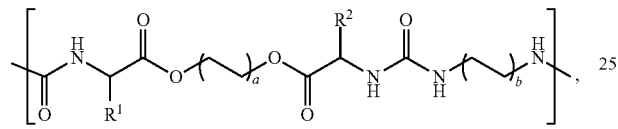

wherein
each $R^1$ and $R^2$ are each independently, at each occurrence in the polymer, a hydrophilic group;
a is independently, at each occurrence in the polymer, 1, 2, or 3; and
b is independently, at each occurrence in the polymer, 2 or 3;
a hydrophobic poly(ester urea) segment; and
a diol segment comprising one or more diol repeat units having a pendant cross-linkable group or hydrogen, wherein the poly(ester urea) segments and diol segments are covalently bonded,
wherein the hydrophilic poly(ester urea) segment and hydrophobic poly(ester urea) segment are 80 to 100% of the total moles of the hydrophilic poly(ester urea) segment, hydrophobic (ester urea) segment, and diol segment.

13. The polymer of claim 12, wherein the hydrophilic group is a side chain of an arginine residue.

14. The polymer of claim 12, wherein the hydrophobic poly(ester urea) segment has the following structure:

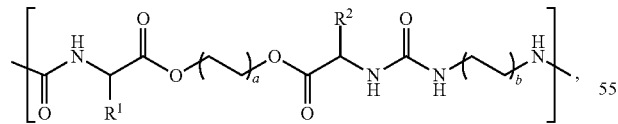

wherein
each $R^1$ and $R^2$ are each independently, at each occurrence in the polymer, a hydrophobic group;
a is independently, at each occurrence in the polymer, 1, 2, or 3; and
b is independently, at each occurrence in the polymer, 2 or 3.

15. The polymer of claim 14, wherein the hydrophobic group is a side chain of a leucine residue.

16. The polymer of claim 12, wherein the diol segment has the following structure:

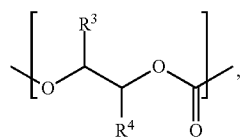

wherein
$R^3$ and $R^4$ are independently, at each occurrence in the polymer, a side-chain comprising a reactive group or a hydrogen.

17. The polymer of claim 16, wherein the reactive group comprises a terminal carbon-carbon double bond.

18. The polymer of claim 12, wherein the hydrophilic poly(ester urea) segment has a molecular weight of 150 to 75,000 g/mol or the hydrophobic poly(ester urea) segment has a molecular weight of 0 to 7,500 g/mol or the diol segment has a molecular weight of 50 to 5,000 g/mol.

19. The polymer of claim 12, wherein the hydrophilic poly(ester urea) segment and hydrophobic poly(ester urea) segment are 80 to 100% of the total moles of the hydrophilic poly(ester urea) segment, hydrophobic (ester urea) segment, and diol segment, and the diol segment is 0 to 20% of the total moles of the hydrophilic poly(ester urea) segment, hydrophobic (ester urea) segment, and diol segment, with the proviso that at least one diol segment is present.

20. The polymer of claim 12, wherein the polymer has the following structure:

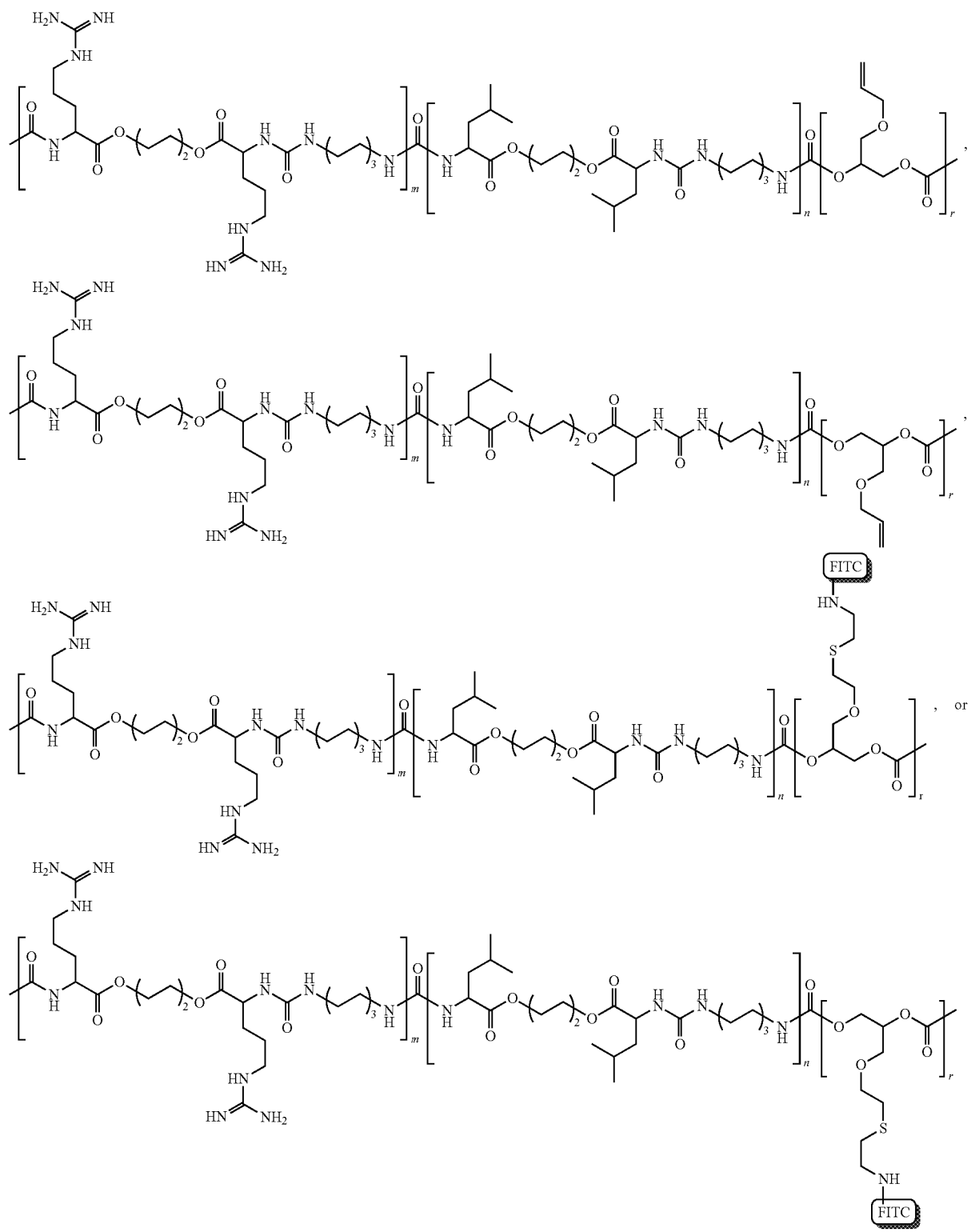
wherein
FITC is

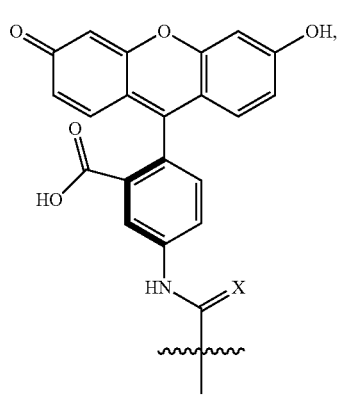

wherein X is sulfur or oxygen;

m is 1 to 70;
n is 0 to 14; and
r is 0 to 20.

21. A method of administering a drug to an individual comprising:
  administering to an individual a nanoparticle formed from a polymer of claim 1, wherein the nanoparticle comprises a drug sequestered in the nanoparticle.

22. The method of claim 21, wherein the drug is a hydrophobic drug.

23. The method of claim 22, wherein the drug is gambogic acid, doxorubicin, camptothecin, or paclitaxel.

24. The method of claim 21, wherein the loading efficiency is 8 to 17 wt %.

25. The method of claim 21, wherein the individual has been diagnosed with or suspected of having cancer.

* * * * *